(12) United States Patent
Mills

(10) Patent No.: US 7,188,033 B2
(45) Date of Patent: Mar. 6, 2007

(54) METHOD AND SYSTEM OF COMPUTING AND RENDERING THE NATURE OF THE CHEMICAL BOND OF HYDROGEN-TYPE MOLECULES AND MOLECULAR IONS

(75) Inventor: Randell L. Mills, Cranbury, NJ (US)

(73) Assignee: Blacklight Power Incorporated, Cranbury, NJ (US)

( * ) Notice: Subject to any disclaimer, the term of this patent is extended or adjusted under 35 U.S.C. 154(b) by 0 days.

(21) Appl. No.: 10/893,280

(22) Filed: Jul. 19, 2004

(65) Prior Publication Data

US 2005/0209788 A1    Sep. 22, 2005

Related U.S. Application Data

(60) Provisional application No. 60/488,622, filed on Jul. 21, 2003, provisional application No. 60/491,963, filed on Aug. 4, 2003, provisional application No. 60/534,112, filed on Jan. 5, 2004, provisional application No. 60/542,278, filed on Feb. 9, 2004, provisional application No. 60/571,667, filed on May 17, 2004.

(51) Int. Cl.
    *G01N 31/00* (2006.01)
(52) U.S. Cl. ............ 702/22; 702/23; 702/19; 372/69; 372/19; 436/173
(58) Field of Classification Search ........ 702/22, 702/27, 188, 23, 19; 372/19, 69; 436/173
    See application file for complete search history.

(56) References Cited

U.S. PATENT DOCUMENTS 1,001,589 A    8/1911    Hatfield
2,708,656 A    5/1955    Fermi
3,253,884 A    5/1966    Jung et al.
3,297,484 A    1/1967    Niedrach
3,300,345 A    1/1967    Lyons
3,359,422 A    12/1967   Pollock
3,377,265 A    4/1968    Caeser
3,448,035 A    6/1969    Serfass (Continued)

FOREIGN PATENT DOCUMENTS

EP    0 392 325 A3    10/1990

(Continued)

OTHER PUBLICATIONS

Abdallah, et. al. "The Behavior of Nitrogen Excited in an Inductively Coupled Argon Plasma." *J. Appl. Phys.*, vol. 88, No. 1, Jul. 2000, pp. 20-33.

(Continued)

*Primary Examiner*—Carol S. W. Tsai
(74) *Attorney, Agent, or Firm*—Jeffrey S. Melcher; Manelli Denison & Selter, PLLC

(57) ABSTRACT

Provided is a system of computing and rendering a nature of a chemical bond based on physical, Maxwellian solutions of charge, mass, and current density functions of hydrogen-type molecules and molecular ions. The system includes a processor for processing Maxwellian equations representing charge, mass, and current density functions of hydrogen-type molecules and molecular ions and an output device in communication with the processor for displaying the nature of the chemical bond.

53 Claims, 1 Drawing Sheet

U.S. PATENT DOCUMENTS

Figure 1A:
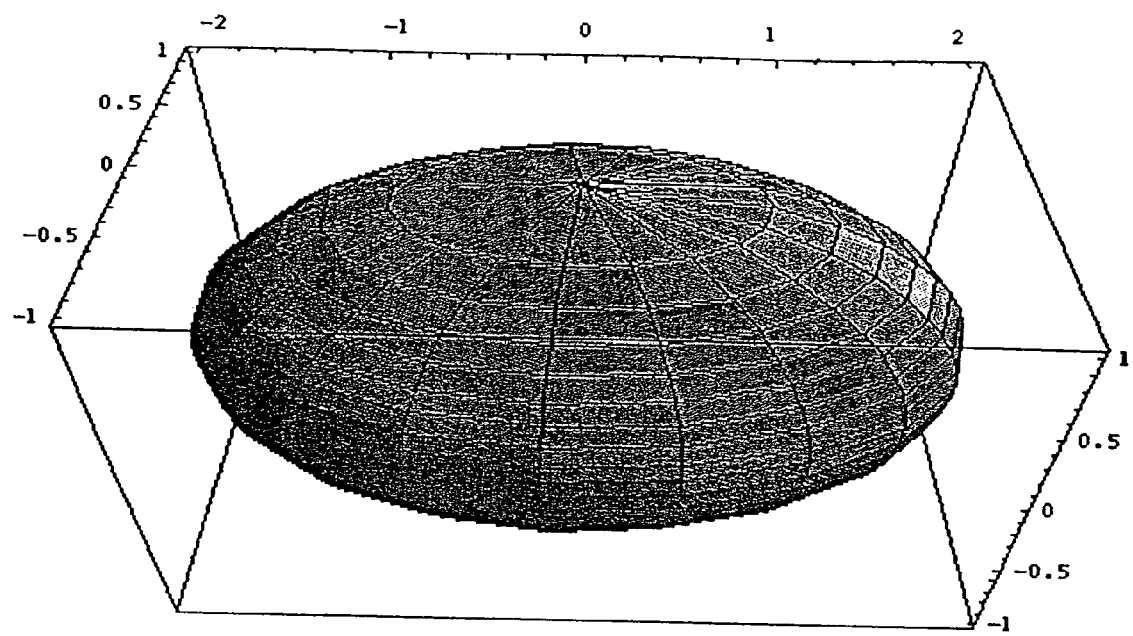

| | | | |
|---|---|---|---|
| 3,669,745 A | | 6/1972 | Beccu |
| 3,701,632 A | | 10/1972 | Lovelock |
| 3,755,128 A | | 8/1973 | Herwig |
| 3,816,192 A | | 6/1974 | Brower |
| 3,835,019 A | | 9/1974 | Lovelock |
| 3,917,520 A | | 11/1975 | Katz |
| 4,000,036 A | * | 12/1976 | Ensley .................... 376/123 |
| 4,149,931 A | * | 4/1979 | Christensen ............... 376/134 |
| 4,155,712 A | | 5/1979 | Taschek |
| 4,265,720 A | | 5/1981 | Winstel |
| 4,274,938 A | | 6/1981 | Schulten |
| 4,327,071 A | | 4/1982 | Chiu et al. |
| 4,337,126 A | | 6/1982 | Gilligan, III et al. |
| 4,353,871 A | | 10/1982 | Bartilt et al. |
| 4,487,670 A | | 12/1984 | Bellanger |
| 4,512,966 A | | 4/1985 | Nelson |
| 4,568,568 A | | 2/1986 | Asano |
| 4,664,904 A | | 5/1987 | Wolfrum |
| 4,702,894 A | | 10/1987 | Cornish |
| 4,737,249 A | | 4/1988 | Shepard, Jr. |
| 4,774,065 A | | 9/1988 | Penzorn |
| 4,792,725 A | * | 12/1988 | Levy et al. .................. 315/39 |
| 4,808,286 A | | 2/1989 | Angelo, II |
| 4,923,770 A | | 5/1990 | Grasselli |
| 4,957,727 A | | 9/1990 | Bogdanovic |
| 4,968,395 A | | 11/1990 | Pavelle |
| 4,986,887 A | | 1/1991 | Gupta |
| 5,215,729 A | | 6/1993 | Buxbaum |
| 5,273,635 A | | 12/1993 | Gernert |
| 5,318,675 A | | 6/1994 | Patterson |
| 5,372,688 A | | 12/1994 | Patterson |
| 5,449,434 A | * | 9/1995 | Hooke et al. ................ 216/70 |
| 5,577,090 A | * | 11/1996 | Moses ........................ 378/64 |
| 5,593,640 A | | 1/1997 | Long et al. |
| 5,669,975 A | * | 9/1997 | Ashtiani ................ 118/723 I |
| 5,761,481 A | * | 6/1998 | Kadoch et al. ............... 703/2 |
| 5,789,744 A | | 8/1998 | Spence et al. |
| 5,801,971 A | * | 9/1998 | Ohta ........................... 703/12 |
| 5,819,073 A | * | 10/1998 | Nakamura ................... 716/20 |
| 5,838,760 A | * | 11/1998 | Moses ........................ 378/119 |
| 5,864,322 A | * | 1/1999 | Pollon et al. ............... 343/909 |
| 5,883,005 A | * | 3/1999 | Minton et al. ............. 438/707 |
| 5,888,414 A | * | 3/1999 | Collins et al. ................ 216/68 |
| 5,969,470 A | * | 10/1999 | Druz et al. ............. 313/359.1 |
| 6,024,935 A | * | 2/2000 | Mills et al. ............. 423/648.1 |
| 6,064,154 A | * | 5/2000 | Crouch et al. ......... 315/39.57 |
| 6,150,755 A | * | 11/2000 | Druz et al. ............. 313/359.1 |
| 6,151,532 A | * | 11/2000 | Barone et al. ............. 700/121 |
| 6,444,137 B1 | * | 9/2002 | Collins et al. ................ 216/79 |
| 6,690,705 B2 | * | 2/2004 | Maksimov et al. .......... 372/69 |
| 2002/0133326 A1 | * | 9/2002 | Chung et al. ................. 703/18 |

FOREIGN PATENT DOCUMENTS

| | | |
|---|---|---|
| EP | 0 395 066 A2 | 10/1990 |
| GB | 2 343 291 | 5/2000 |
| JP | 53-134792 | 11/1978 |
| JP | 56-136644 | 3/1980 |
| JP | 2002008892 A * | 1/2002 |
| WO | WO 90/10935 A1 | 9/1990 |
| WO | WO 90/13126 A1 | 11/1990 |
| WO | WO 90/14668 A2 | 11/1990 |
| WO | WO 91/01036 A1 | 1/1991 |
| WO | WO 91/08573 A1 | 6/1991 |
| WO | WO 92/10838 A1 | 6/1992 |
| WO | WO 93/17437 A1 | 9/1993 |
| WO | WO 94/10688 A1 | 5/1994 |
| WO | WO 94/14163 A1 | 6/1994 |
| WO | WO 94/15342 A1 | 7/1994 |
| WO | WO 94/29873 A2 | 12/1994 |
| WO | WO 95/20816 A1 | 8/1995 |
| WO | WO 96/42085 A2 | 12/1996 |
| WO | WO 99/05735 A1 | 3/1999 |
| WO | WO 99/26078 A1 | 5/1999 |
| WO | WO 99/34322 A1 | 7/1999 |
| WO | WO 99/35698 A3 | 7/1999 |
| WO | WO 00/07931 A1 | 2/2000 |
| WO | WO 00/07932 A2 | 2/2000 |
| WO | WO 00/25320 A1 | 5/2000 |
| WO | WO 01/18948 A1 | 3/2001 |
| WO | WO 01/21300 A2 | 3/2001 |
| WO | WO 01/22472 A2 | 3/2001 |
| WO | WO 01/70627 A3 | 8/2001 |
| WO | WO 01/095944 A2 | 12/2001 |
| WO | WO 02/08787 A2 | 1/2002 |
| WO | WO 02/16956 A1 | 2/2002 |
| WO | WO 02/087291 A2 | 10/2002 |
| WO | WO 02/088020 A2 | 11/2002 |
| WO | WO 03/066516 A2 | 8/2003 |
| WO | WO 03/093173 A2 | 11/2003 |
| WO | WO 04/092058 A2 | 10/2004 |
| WO | WO 05/067678 A2 | 7/2005 |
| WO | WO 05/041368 A2 | 10/2005 |

OTHER PUBLICATIONS

Abelès, Ed. Chapter 9, "Structure of Trapped Electron and Trapped Hole Centers in Alkali Halides 'Color Centers'." *Optical Properties of Solids*, 1972, pp. 718-754.

Abramova, et. al. "Tornado-type closed magnetic trap for an electron cyclotron resonance ion source." *Review of Scientific Instruments*, vol. 71, No. 2, Feb. 2000, pp. 921-923.

Albagli, et. al. "Measurement and Analysis of Neutron and Gamma-Ray Emission Rates, Other Fusion Products, and Power in Electrochemical Cells Having Pd Cathodes." *Journal of Fusion Energy*, vol. 9, No. 2, Jun. 1990, pp. 133-148.

Alber, et. al. "Search for Neutrons from Cold Nuclear Fusion." *Z. Phys. A.—Atomic Nuclei*, vol. 333, 1989, pp. 319-320.

Alessandrello, et. al. "Search for Cold Fusion Induced by Electrolysis in Palladium." *Il Nuovo Cimento*, vol. 103A, No. 11, Nov. 1990, pp. 1617-1638.

Alger et al. "F Centers in Pure and Hydride-Containing Alkali Halide crystals." *Physical Review*, vol. 97, Jan. 15, 1955, pp. 277-287.

Arfken. "Mathematical Methods for Physicists." *Academic Press*, 1970, pp. 413-415.

Associated Press. "Panel Opposes Cold Fusion Efforts." *The Washington Post*, Jul. 13, 1989, p. A14.

Associated Press. "Pennsylvania Company . . . Cold Fusion Mystery." *Lexis Nexis* Reprint, 1991.

Associated Press. "Physicist: Utah Cold-Fusion Gear Doesn't Work." *The Washington Post*, Mar. 29, 1990, p. A3.

"Atomic Physics Progress Report 1995-1996" (internet page) atompc2.fysik.lth.se/AFDOCS/Progrep956/contents.asp (author and date unknown).

"Atomic Spectroscopy" (internet page) physics.nist.gov/Pubs/AtSpec/node20.html (author and date unknown).

Baard, Erik. "The Empire Strikes Back." *The Village Voice*, Apr. 26-May 2, 2000.

Baard, Erik. "Quantum Leap." *The Village Voice*, Dec. 22-28, 1999.

Baard, Erik. "Researcher Claims Power Tech That Defies Quantum Theory." *Dow Jones Newswires*, Oct. 6, 1999.

Baard, Erik, "Hydrino Theorist Gets Nod From NASA-Funded Investigation Eureka?", *The Village Voice*, Dec. 6, 2002.

Balke, et. al. "Limits on Neutron Emission From 'Cold Fusion' in Metal Hydrides.", *Physical Review C*, vol. 42, No. 1, Jul. 1990, pp. 30-37.

Barmann et. al. "Spatially and Temporally Resolved Studies of the Electron Density in Liquid Streamers by Emission Spectroscopy" (Internet page) atompc2.fysic.lth.se/AFDOCS/Progrep956/5al.htm (Atomic Physics Progress Report).

Barth, "Bigger Than Fire?", Gale Group Magazine DB, The Gale Group, 2003.

Barton, et al, "Investigating Radio Frequency Plasmas Used for the modification of Polymer Surfaces." *J. Phys. Chem. B*, vol. 103, 1999, pp. 4423-4430.

Bäuerle et al. "Infared Vinrational Absorption by U-Centers in NaI." *Phys. Stat. Sol.*, vol. 24, 1967, pp. 207-215.

Beiser, A. *Concepts of Modern Physics*, Fourth Edition, McGraw-Hill Book Company, New York, 1978, p. 407.

Benetskii, et. al. "An Attempt to Observe Cold Thermonuclear Fusion in a Condensed Medium." *Nuclear Research Institute*, AS USSR, May 1989, pp. 75-78.

Besenbacher, et. al. "Search for Cold Fusion in Plasma-Charged Pd-D and Ti-D Systems." *Journal of Fusion Energy*, vol. 9, No. 3, Sep. 1990, pp. 315-317.

Best, Ben. "The Copenhagen Interpretation of Quantum Mechanics." (internet page) www.benbest.com/science/quantum.html. (no date litsed).

Bethe, et. al. "Quantum Mechanics of One and Two-Electron Atoms." *Cornell University*, 1977, pp. 2, 9-12, 47, 83-84, 92, 107.

Bishop. "It ain't over til it's over . . . Cold Fusion." *Popular Science*, Aug. 1993, pp. 47-51.

Bishop. "More Labs Report Cold Fusion Results." *Wall Street Journal*, Oct. 19, 1992.

Bjorken et al., "Relativistische Quantenmechanik", *Die Dirac-Gleichung*, pp. 22-25, 1964.

"Blacklight Power—do they have something significant?" (internet page) www.phact.org/e/blp.htm (author and date unknown).

Blochinzew, *Grundlagen Der Quantenmechanik*, Veb Deutscher Verlag Der Wissenschaften, 1967.

Bleu. "Cold Fusion Lies." *Deja News on the Internet*, Apr. 13, 1997.

Blue. "Randell Mills' Sells Pot Shards." *Deja News on the Internet*, Apr. 30, 1997.

Bogaerts, et al. "Effects of adding hydrogen to an argon glow discharge: overview of relevant processes and some qualitative explanations." *Journal of Analytical Atomic Spectrometry*, Mar. 2000.

Boniface, et. al. "Calorimetry for Ni/$K_2CO_3$ Cell." AECL Research, Jun. 1994.

Bosch, et. al. "Electrochemical Cold Fusion Trials at IPP Garching." *Journal of Fusion Energy*, vol. 9, No. 2, Jun. 1990, pp. 165-186.

*Boston Globe.*, "Successful nuclear fusion experiment by the Italians." Wednesday, Apr. 19, 1989.

Braaten. "Ridiculously Easy Test Yields Claim of Energy Triumph." *The Washington Times*, Mar. 24, 1989, p. A5.

Bradford. "A Calorimetric Investigation of the Reaction of Hydrogen with Sample PSU #1." A Confidential Report submitted to Hydrocatalysis Power Corporation, Sep. 1994.

Briars. "Critique of New Energy, New Physics." 7 segments, *Deja News on the Internet*, Mar. 9, 1989.

Brewer, Shelby T. Book review of "The grand Unified Theory of Classical Quantum Mechanics (Hardcover) by Randell L., Dr. Mills." (internet page) http://www.amazon.com/go/product/product-.

Broad. "2 Teams Put New Life in Cold Fusion Theory." *New York Times*, Apr. 26, 1991, p. A18.

Broad. "Cold-Fusion Claim is Faulted on Ethics as Well as Science." *The New York Times*, Mar. 17, 1991, p. 1.

Browne. "Fusion Claims is Greeted With Scorn by Physicists." *The New York Times*, May 3, 1989, pp. A1 and A22.

Browne. "Physicists Put Atom in 2 Places at Once." *The New York Times*.

Bush. "A Light Water Excess Heat Reaction Suggests That 'Cold Fusion' May Be 'Alkali-Hydrogen Fusion'." *Fusion Technology*, vol. 22, Sep. 1992, pp. 301-322.

Bush, et. al. "Helium Production During the Electrolysis . . . Experiments." *J. Electroanal Chem.*, vol. 304, 1991, pp. 271-278.

Bush, et. al. "Helium Production During the Electrolysis . . . Experiments." *Preliminary Note, Univ. of Texas*, pp. 1-12.

Bush, et. al. "Power in a Jar: the Debate Heats Up." *Science & Technology*, Oct. 26, 1992.

Carolina, et al. "Effect of Dielectric Constant, Cavities in Series and Cavities in Parallel on the Product Distribution of the Oligomerization of Methane via Microwave Plasmas." *J. Phys. Chem.*, vol. 100, 1996, pp. 17866-17872.

Catlett, et. al. "Hydrogen transport in lithium hydride as a function of pressure." *The Journal of Chemical Physics*, vol. 58, No. 8, Apr. 1978, pp. 3432-3438.

Chapline. "Cold Confusion." *UCRL-101583*, Jul. 1989, pp. 1-9.

Chien, et. al. "On an Electrode . . . Tritium and Helium." *J. Electroanal Chem.*, 1992, pp. 189-212.

Clark, et. al. "Excess Energy Cell Final Report." Apr. 1995.

Close. "Too Hot to Handle-The Race for Cold Fusion." *Princeton University Press*, 1989.

Condon, et. al. "The Theory of Atomic Spectra." MacMillan Company: New York. 1935. pp. 44-78, 112-146.

Conrads, et. al. "Emission in the Deep Vacuum Ultraviolet from an Incandescently Drive Plasma in a Potassium Carbonate Cell", *Plasma Sources Science and Technology*, submitted.

Cooke. "ORNL/FTR-3341." Jul. 31, 1989, pp. 2-15.

Cribier, et. al. "Conventional Sources of Fast Neutrons in Cold Fusion Experiments." *Physics Letters B*, vol. 228, No. 1, Sep. 7, 1989, pp. 163-166.

Criddle. "The Roles of Solution . . . Excess Heating." *Electrochemical Science & Technology Centre*, Univ. of Ottawa.

Cvetanovic et. al. "Excessive Balmer line broadening in a plane cathode abnormal glow discharge in hydrogen." *Journal of Applied Physics 97*. Jan. 18, 2005.

Datz, et. al. "Molecular Association in Alkali Halide Vapors." Journal of Chemical Physics, vol. 34, No. 5, Feb. 1961, pp. 558-564.

Dagani. "Cold Fusion believer turns skeptic crusades for more rigorous research." *C&EN Washington*, Jun. 5, 1995, pp. 34-45, 38 and 40.

Dagani "Cold Fusion-Utah Pressures Pons, Fleischmann." *C&EN*, Jan. 14, 1991, pp. 4-5.

Dagani. "Latest Cold Fusion Results Fail to Win Over Skeptics." *C&EN*, Jun. 14, 1993, pp. 38-40.

Dagani. "New Evidence Claimed for Nuclear Process in 'Cold Fusion'." *C&EN Washington*, Apr. 1991, pp. 31-33.

Delbecq et al. "Pragmatic Resonance Investigation of Irradiated KCl Crystals Containing U-Centers." *Phys. Rev.*, vol. 104, Nov. 1, 1956, pp. 599-604.

Dennis "Hidden Variables and Relativistic Tachyons" (internet page) www.objectivescience.com/articles/ed_tachy.htm (Date unknown).

Dery et. al. "Effect of Dielectric constant, Cavities in Series, and Cavities in Parallel on the Product Description of the Oligomerization of Methane via Microwave Plasmas." *Journal of Physical Chemistry 1996*, vol. 100. Jul. 8, 1996. pp. 17866-.

Dötsch et al. "Localized Vibrations of H and D ions in NaF and LiF." *Solid States Communications*, vol. 3, 1965, pp. 297-298.

Dufour, et. al. "Interaction of Palladium/Hydrogen and Palladium. Deuterium to Measure the Excess Energy Per Atom for Each Isotope." *Fusion Technology*, vol. 32, Mar. 1997, pp. 198-209.

Durr, et. al. "Origin of quantum-mechanical complementarity probed by a 'which-way' experiment in an atom interferometer." *Nature*, vol. 395, Sep. 3, 1998, pp. 33-37.

"Earth Tech's Campaign to Replicate one of BlackLight Power Excess Heat Results." Dec. 20, 1997 available at www.eden.com/~little/blp/prelim.html, pp. 1-41.

Evans, et. al. "Time-of-Flight Secondary Ion Mass Spectroscopy (TOF-SIMS) Surface Analysis Report." CE & A No. 40150, Mar. 1994.

Evans, et. al. "XPS/ESCA Results." CE & A No. 44545, Nov. 1994.

Evans Analytical Group. Product Descriptions: Time-of-Flight Secondary Mass Spectrometry (TOF-SIMS) and X-Ray Photoelectron Spectroscopy (XPS) Electron Spectroscopy for Chemical Anaylsis (ESCA). (no date or author listed).

Ewing, et. al. "A sensitive multi-detector neutron counter used to monitory cold fusion experiments in an underground laboratory; negative results and positive artifacts." *IEE Transactions on nuclear science*, vol. 37, No. 3, Jun. 1990, pp. 1165-1170.

"Experimental Verification by Idaho National Engineering Laboratory." pp. 13-25.

Faller, et. al. "Investigation of Cold Fusion in Heavy Water." *J. Radioanal. Nucl. Chem. Letter*, vol. 137, No. 1, Aug. 21, 1989, pp. 9-16.

Fan et al., "X-ray photoelectron spectroscopy studies of CVD diamond films", *Surface and Interface Analysis*, 34:703-707, 2002.

Feynman, et al. "The Feynman Lectures of Physics: Quantum Mechanics." 1965.

Fine, Arthur. "The Shaky Game: Einstein Realism and the Quantum Theory." *The University of Chicago Press*, 1986, pp. 64-85.

Fischer. "Die optische Absorption der $U_2$-Zentren in Alkalihalogenidkristallen", *Zeitschrift für Physik*, vol. 131, 1952, pp. 488-504.

Fischer et al. "$Sh^-$, $S^-$ Und $S^-$Zentren in KC1-Kristallen." *Physics Letters*, vol. 13, Oct. 27, 1964, pp. 113-114.

J. Flemming, et. al. "Calorimetric Studies of Electrochemical Incorporation of Hydrogen Isotopes into Palladium.".

Fozza, et. al. "Vacuum ultraviolet to visible emission from hydrogen plasma: Effect of excitation frequency." *Journal of Applied Physics*, vol. 88, No. 1, Jul. 2000, pp. 20-33.

Fried et al. "Solution for the Two-Electron Correlation Function in a Plasma." *The Physical Review*, vol. 122, Apr. 1, 1961, pp. 1-8.

Fritz. "Anionlücken und Zwischengitterionen in Alkalihalogenid-Alkalihydrid-Mischkristallen." *J. Phys. Chem. Solids*, vol. 23, 1962, pp. 375-394.

Fuchs and Peres. "Quantum Theory Needs No 'Interpretation'." *Physics Today*, Mar. 2000, p. 70.

Fujimoto, et. al. "Ratio of Balmer line intensities resulting from dissociative excitation of molecular hydrogen in an ionizing plasma." *J. Appl. Phys.*, vol. 66, No. 6, Sep. 1989, pp. 2315-2319.

Gernert, et. al. "Anomalous Heat From Atomic Hydrogen in Contact with Potassium Carbonate." Thermacore, Inc.

Gottfried, "Quantum electrodynamics: Matter all in the mind", (internet page) www.nature.com/cgi-taf/DynaPage.t . . . e/journal/v419/n6903/full/419117a_r.html, 2002.

Gulyaev "Gigantic Atoms in Space" (internet page) www.astronomy.org.nz/events/months . . . reviews/2001/gigantic_atoms_in_space.htm (date unknown).

Hadfield. "Lukewarm reception for Japanese cold fusion." *New Scientist*, Oct. 31, 1992. p. 10.

Hajdas, et. al. "Search for Cold-Fusion Events." *Solid State Communications*, vol. 72, No. 4, 1989, pp. 309-313.

Hansen, et. al. "A response to hydrogen +oxygen recombination and related heat generation in undivided electrolysis cells." *J. of Electroanalytical Chemistry*, vol. 447, 1998, pp. 225-226.

Hardy, et. al. "The Volatility of Nitrates and Nitrites of the Alkali Metals." *Journal of the Chemical Society*, 1963, pp. 5130-5134.

Haus. "On the radiation from point charges." *American Journal of Physics*, vol. 54, No. 12, Dec. 1986, pp. 1126-1129.

Hayashi, Shigenobu. "Accurate determination of $^1H$ Knight shifts in $Mg_2NiH_x$ and $MgH_x$ by means of high-speed magic angle spinning." *Journal of Alloys and Compounds*, vol. 248, 1997, pp. 66-69.

Hayashi, et. al. "$^1H$ NMR and magnetization measurements of a nanostructured composite material of the $Mg_2Ni$-H system synthesized by reactive mechanical grinding." *Journal of Alloys and Compounds*, vol. 256, 1997, pp. 159-165.

Hayashi, et. al. "Local structures and hydrogen dynamics in amorphous and nanostructured Mg-Ni-H systems as studied by $^1H$ and $^2H$ nuclear magnetic resonance.".

Heisenberg, W. "Über den anschaulichen Inhalt der quantentheoretischen Kinematik und Mechanik." *Zeitschrift für Physik*, vol. 43, 1927, pp. 172-198.

Heitler, W. "The Quantum Theory of Radiation." *University of Zürich*, 1984, pp. 104.

Henderson, et. at. "More Searches for Cold Fusion." *Journal of Fusion Energy*, vol. 9, No. 4, 1990.

Hilsch. "Eine neue Lichtabsorption in Alkalihalogenidkristalle." *Fachgruppe II*, pp. 322-328.

Hilsch. "Über die Diffusion und Reaktion von Wassestoff in KBr-Kristallen." *Annalen der Physik*, vol. 40, 1037, pp. 407-720.

Hilts. "Significant Errors Reported in Utah Fusion Experts." *The Washington Post*, May 2, 1989, pp. A1 and A7.

Hines, "Scientific Mistakes: N-rays and Polywater", *Pseudoscience and the Paranormal*, Prometheus Books, 1988, pp. 8-13.

Hodoroaba, et. al."Investigations of the effect of hydrogen in an argon glow discharge." *J. of Analytical Atomic Spectrometry*, www.rsc.org/ej/ja/2000/B0023671/ (1 of 14), Aug. 2000.

Hollander, et. al. "Vacuum ultraviolet emission from microwave plasmas of hydrogen and its mixtures with helium and oxygen." *J. Vac. Sci. Technol.*, A12 (3), May/Jun. 1994, pp. 879-882.

Horanyi. "Some Basic Electrochemistry and the Cold Nuclear Fusion of Deuterium." *J. Radioanal. Nucl. Chem. Letters*, vol. 137, No. 1, Aug. 21, 1989, pp. 23-28.

Huizenga. "Abstract from 'New developments in the cold fusion saga'." *Abstracts of papers of the American Chemical Society*, vol. 207, Mar. 13, 1994, p. 6.

Huizeng. "Cold Fusion." *C & EN*, vol. 70, Jul. 20, 1992, p. 3.

Huizenga. "Cold Fusion Labeled Fiasco of the Century." *Forum for Applied Research and Public Policy*, vol. 7, No. 4, pp. 78-83.

Huizenga. "Cold Fusion—The Scientific Fiasco of the Century." *Oxford University Press*, 1993.

Jackson, John David. "Classical Electrodynamics." *University of California*, Berkley, 1975, Ch. 14.

Jacox, et. al. "INEL XPS Report." Idaho National Engineering Laboratory, EG &G Idaho, Inc., Nov. 1993.

Jansson. "Hydrocatalysis:: A New Energy Paradigm for the $21^{st}$ Century." A Thesis, Master of Science in Engineering Degree in the Graduate Division of Rowan University, May 1997.

Jeffreys, et al. "Methods of Mathematical Physics." *Cambridge*, 1950, pp. 618.

Johansson, et. al. "A Model for the origin of the anomalous and very bright UV lines of FE II in gaseous condensations of the star η Carinae" *Astronomy & Astrophysics*. vol. 378 (2001) pp. 266-278.

Jones. "Current Issues in Cold Fusion . . . Particles." *Surface and Coatings Technology*, vol. 51, 1992, pp. 283-289.

Jones, et. al. "Examination of Claims of Miles . . . Experiments." *J. Phys. Chem.*, 1995, pp. 6966-6972.

Jones, et. al. "Faradaic Efficiencies . . . Cells." *J. Phys. Chem.*, 1995, pp. 6973-6979.

Jones, et. al. "Serious Flaws in Patterson (SOFE '95)Demo on Cold Fusion." available at http//x7.dejanews.com, Oct. 1995.

Joyce, et. al. "Ion Distribution functions in an Ar-Cl ECR Discharge." *Plasma Sources Sci. Technol.*, vol. 9,2000, pp. 429-436.

Judge, "SHE-2 Latest Solar EUV Measurements"(internet page) www.usc.edu/dept/space_science/seh2data.htm, Aug. 18, 1997.

Ivanco, et. al. "Calorimetry For a $Ni/K_2CO_3$ Cell." *AECL Research*, Jun. 1994.

Kahn. "Confusion in a Jar." *Nova*, 1991.

Karabut, et. al. "Nuclear Product . . . Deuterium." *Physics Letters A170*, 1992, pp. 265-272.

Karplus and Porter. *Atoms and Molecules: An Introduction for Students of Physical Chemistry*, The Benjamin/Cummings Publishing Company, Menlo Park, California, 1970, p. 3, 118-123.

Karplus and Porter. *Atoms and Molecules: An Introduction for Students of Physical Chemistry*, The Benjamin/Cummings Publishing Company, Menlo Park, California, 1970, p. 567.

Kawai, et. al. "Electron temperature, density, and metastable-atom density of argon electron-cyclotron-resonance plasma discharged by 7.0, 8.0, and 9.4 Ghz microwaves." *J. Vac. Sci. Technol. A*, vol. 18, No. 5, Sep./Oct. 2000, pp. 2207-2212.

Keefer, Ph.D., "Interim Report on BlackLight Power Technology: Its Apparent Scientific Basis, State of Development and Suitability for Commercialization by Liebert Corporation.".

Kerkhoff. "Zum photochemischen Verhalten sauerstoffhaltiger Komplexe in Alkalihalogenidkristalle." *Zeitschrift für Physik*, vol. 158, 1960, pp. 595-606.

Kerkhoff et al. "Electronenpsin-Resonanz und Photochemie des $U_2$-Zentrums in Alkalihalogenid-Kristallen." *Zeitschrift für Physik*, vol. 173, 1963, pp. 184-202.

Klein. "Attachments to Report of Cold Fusion Testing." *Cold Fusion*, No. 9, pp. 16-19.

Kleinschrod. "Photochemische Zersetzung von KH und KD in KBr-Kristallen." *Ausgegeban*, Jan. 5, 1939, pp. 143-148.

Kleppner, et. al. "One Hundred Years of Quantum Physics." *SCIENCE*, vol. 289, Aug. 2000, pp. 893-898.

Kline-Anderson, Inc. "Review of Schedule and Resource Requirements to Develop a Hydrocatalysis Functional Prototype Unit." Final Report for Technology Insights, Oct. 1996.

Kolos, et. al. "Accurate Adiabatic Treatment of the Ground State of the Hydrogen Molecule*." *Journal of Chemical Physics*, vol. 41, No. 12, Dec. 1964, pp. 3663-3673.

Kolos, et. al. "Accurate Electronic Wave Functions for the $H_2$ Molecule*." *Reviews of Modern Physics*, vol. 32, No. 2, Apr. 1960, pp. 219-232.

Kolos, et. al. "Improved Theoretical Ground-State Energy of the Hydrogen Molecule*." *Journal of Chemical Physics*, vol. 49, No. 1, Jul. 1968, pp. 404-410.

Kovacevic et. al. "The Dynamic Response of the Plasma on the Dust Formation in $Ar/C_2H_2$ RF Discharges." *International Conference on Phenomena in Ionized Gases*. (no date listed).

Kreig "Hydrinos: A state below the ground state" (internet page) www.phact.org/e/x/hydrino.htm (date unknown).

Kreysa, et. al. "A Critical Anaylsis of Electrochemical Nuclear Fusion Experiments." *J. Electroanal. Chem.*, vol. 266, 1989, pp. 437-450.

Khun, H.G."Atomic Spectra." Academic Press: New York. 1962. pp. 114-117.

Kuraica, et. al."Line Shapes of Atomic Hydrogen in a Plane-Cathode abnormal glow discharge." *Physical Review A*, Vo. 46, No. 7, Oct. 1992, pp. 4429-4432.

Kurunczi, et. al. "Excimer formation in high-pressure micro hollow cathode discharge plasmas in helium initiated by low-energy collision." *International Journal of Mass Spectrometry*, vol. 205, 2001, pp. 277-283.

Kurunczi, et. al. "Hydrogen Lyman$\alpha$ and Lyman$\beta$ emissions from high-pressure micro hollow cathode discharges in . . . " *J. Phys. B: At. Mol. Opt. Phy.*, vol. 32, 1999, pp. L651-L658.

Kurtz, et. al. "Report on Calometric Investigations of Gas-Phase Catalyzed Hydrino Formation." Hydrocatalysis Power Corp. Report, Dec. 1996.

Labov. "Spectral Observations . . . Background." *The Astrophysical Journal*, vol. 371, Apr. 20, 1991, pp. 810-819.

Leggett, et. al. "Exact Upper Bound . . . 'Cold Fusion'." *Physical Review Letters*, vol. 63, No. 2, Jul. 1989, pp. 190-194.

"Lehigh X-Ray Photoelectron Spectroscopy Report." Dec. 8, 1993.

Lewis, et. al., "Searches for Low-Temperature Nuclear Fusion of Deuterium in Palladium." *Nature*, vol. 340, Aug. 17, 1989, pp. 525-530.

Luggenholscher et al., "Investigations on Electric Field Distributions in a Microwave Discharge in Hyrdogen", (date unknown).

Lüpke. "Über Sensibilisierung der photochemischen Wirkung in Alkalihalogenidkristallen." *Annalen der Physik*, vol. 21, 1934, pp. 1-14.

Luque et. al. "Experimental research into the influence of ion dynamics when measuring the electron density from the Stark broadening of the H$\alpha$ and G$\beta$ lines." *Journal of Physics B: Atomic, Molecular, and Optical Physics*, vol. 36. 2003.

Lüty. "Über Die Natur Der $V_3$-Zentren In Strahlungsverfäbtem KCCl." *J. Phys. Chem. Solids*, vol. 23, 1962, pp. 677-681.

Maly, et. al. "Electron Transitions on Deep Dirac Levels I." *ANS Reprint, Fusion Technology*, vol. 24, Nov. 1993, pp. 307-318.

Marchese et. al. "The BlackLight Rocket Engine." Rowan University: Glassboror, NJ. Nov. 30, 2002.

Margenau, et. al. "The Mathematics of Physics and Chemistry." *Yale University*, 1943, pp. 77-79.

Martienssen. "Photochemische Vorgänge in Alkalihalogenidkristallen." *Zeitschrift für Physik*, vol. 131, 1952, pp. 488-504.

Mayo, et. al. "On the Potential of Direct and MHD Conversion of Power from a Novel Plasma Source to Electricity for Micro distributed Power Applications", *IEEE Transactions on Plasma Science*, submitted.

McNally. "On the Possibility of a Nuclear Mass-Energy Resonance in D+D Reactions at Low Energy." *Fusion Technology*, vol. 16, No. 2, Sep. 1989, pp. 237-239.

McQuarrie. "Quantum Chemistry" University Science Books: Sausalito, CA. 1983 Sections 4-3, 6-4-6-9, 8-5-8-6.

McQuarrie. "Quantum Chemistry" University Science Books: Sausalito, CA. 1983. pp. 221-222.

Merriaman. "An attempted replication of the CETI Cold Fusion Experiment." published on the Internet, May 1, 1997, available at www.math.ucla.edu/~barry/CF/CETIX.html.

Merzbacher, Eugen. "Quantum Mechanics." 1961, p. 198.

Messiah, Albert. "Quantum Mechanics." *Rutgers—The State University*, vol. 1, 1958, p. 130.

Meulenbroeks, et. al. "The argon-hydrogen expanding plasma: model and experiments." *Plasma Sources Sci Technol.*, vol. 4, 1995, pp. 74-85.

Meulenbroeks, et. al. "Influence of molecular processes on the hydrogen atomic system in an expanding argon-hydrogen plasma." *Phys. Plasmas*, vol. 2, No. 3, Mar. 1995pp. 1002-1008.

Miles et. al. "Correlation of Excess . . . Palladium Cathodes." *J. Electronl. Chem.*, 1993, pp. 99-117.

Miles et. al. "Electrochemical . . . Palladium Deuterium System." *J. Electroanal Chem.*, 1990, pp. 241-254.

Miles et. al. "Heat and Helium . . . Experiments." *Conference Proceedings*, vol. 33, 1991, pp. 363-372.

Miles, et. al. "Search for Anomalous Effects . . . Palladium Cathodes." *Naval Air Warfare Center Weapons Division, Proceedings of the $3^{rd}$ Int. Conf. on Cold Fusion*, Nagoya, Japan, Oct. 1992, pp. 21-25.

Miller. "Memo from Bennett Miller to Dr. Robert W. Bass." Oct. 9, 1997, pp. 1-10.

Miskelly, et. al. "Analysis of the Published Calorimetric Evidence for Electrochemical Fusion of Deuterium in Palladium." *Science*, vol. 246, No. 4931, Nov. 10, 1989, pp. 793-796.

Monroe, et. al. "A Schrodinger Cat Superposition State of an Atom." *Science*, vol. 272, May 24, 1996, pp. 1131-1101.

Morrison. "Cold Fusion Update No. 12, IGGPG." Jan. 1997, available online at "www.skypoint.com".

Morrison. "Comments of claims of excess enthalpy by Fleischmann and Pons using simple cells made to boil." *Physics Letter A*, vol. 185, Feb. 28, 1994, pp. 498-502.

Morrison. "Review of Progress in Cold Fusion." *Transactions of Fusion Technology*, vol. 26, Dec. 1994, pp. 48-55.

Morse, et. al. "Methods of Theoretical Physics." *Massachusetts Institute of Technology*, Part 1: Chapter 1-8, 1953, pp. 808-903.

Myers, et. al. "Search for Cold Fusion at D/Pd > 1 Using Ion Implantation." *Journal of Fusion Energy*, vol. 9, No. 3, pp. 30-37, 1990.

Nakhmanson. "The Ghostly Solution of the Quantum Paradoxes and its Experimental Verification." *Frontiers of Fundamental Physics*. Plenum Press: New York. 1994. pp. 591-596.

Neynaber, et. al. "Formation of HeH$^{30}$ from Low-Energy Collisions of Metastable Helium and Molecular Hydrogen." *Journal of Chemical Physics*, vol. 57, No. 12, 1972, pp. 5128-5137.

Niedra. "Replication of the Apparent Excess Heat Effect in Light Water . . . Cell." *NASA Technical Memorandum 107167*, Feb. 1996.

Nieminen. "Hydrogen atoms band together." *Nature*, vol. 356, Mar. 26, 1992, pp. 289-291.

Noninski. "Excess Heat During the Electrolysis of a Light Water . . . Nickel Cathode." *Fusion Technology*, vol. 21, Mar. 1992, pp. 163-167.

Noninsky, et. al. "Determination . . . Heavy Water." *Fusion Technology*, vol. 19, 1990, pp. 365-367.

Notoya. "Cold Fusion . . . Nickel Electrode." *Fusion Technology*, vol. 24, 1993, pp. 202-204.

Notoya. "Tritium Generation . . . Nickel Electrodes." *Fusion Technology*, vol. 26,1994, pp. 179-183.

Notoya, et. al. "Excess Heat Production in Electrolysis . . . Electrodes." *Proceedings of the Int. Conf. on Cold Fusion*, Oct. 21-25, 1992, Tokyo, Japan.

Odenthal et al., "The Zeeman Splitting of the 5876 Helium Line Studied by Means of a Turnable Dye Laster",*Physica*, pp. 203-216, 1982.

Ohashi, et. al. "Decoding of Thermal Data in Fleischmann & Pons Paper." *J. of Nucl. Sci.. & Tech.*, vol. 26, No. 7, Jul. 1989, pp. 729-732.

Ohmori, et. al. "Excess Heat Evolution . . . Tin Cathodes." *Fusion Technology*, vol. 24, 1993, pp. 293-295.

Oka, et. al. "D₂O-fueled fusion power reactor using electromagnetically induced D-D$_n$, D-D$_p$, and Deuterium-tritium reactions-preliminary design of a reactor system." *Fusion Technology*, vol. 16, No. 2, Sep. 1989, pp. 263-267.

Park, Robert L. "Perpetual Motion: Still Going Around." *Washington Post*, Jan. 12, 2000, p. H03.

Pauling, et. al. "Introduction to Quantum Mechanics with Applications to Chemistry." *Harvard University*, 1985, pp. 121-140.

Peterson. "Evaluation of Heat Production from Light Water Electrolysis Cell of Hydrocatalysis Power Corporation." Draft, *Westinghouse STC*, Feb. 1994.

Phillips, et. al. "Additional Calorimetric Examples of Anomalous Heat From Physical Mixture of K/Carbon and PD/Carbon." Consulting Report, Jan. 1996.

Plasmaphysics.org. Conversion Table: cgc/Sl- units. (internet page) www.plasmaphysics.org/uk/convers.htm. (no author or date listed).

Platt, Charles. "Testing the Current." *Washington Post*. Jun. 25, 2000, p. X05.

Popov. "Electrochemical Characterization of BlackLight Power, Inc. MH as Electrodes for Li-ion Batteries." Department of Chemical Engineering University of South Carolina, Feb. 2000.

Powell et al. *Quantum Mechanics*, Addison-Weskey Publishing Co., Inc., pp. 205-229 and 478-482, 1961.

Price, et. al. "Search for Energetic-Charged Particle Emission ffrom Deuterated Ti and Pd Foils." *Physical Review Letters*, vol. 63, No. 18, Oct. 30, 1989, pp. 1926-1929.

Radavanov, et. al. "Ion Kinetic-Energy Distributions and Balmer-α Excitation in Ar-H$^2$ Radio-Frequency Discharges." *J. Appl. Phys.*, vol. 78, No. 2, Jul. 1995, pp. 746-756.

Rathke. "A critical analysis of the hydrino model." *New Journal of Physics*, vol. 7, 127. 2005.

Rauch et .al. "Some F-Band Optical Oscillator Strengths in Additively Colored Alkali Halides." *Physical Review*, Feb. 1, 1957, vol. 105, pp. 914-920.

Rees. "Cold Fusion . . . What Do We Think?" *Journal of Fusion Energy*, vol. 10, No. 1, 1991, pp. 110-116.

Djurovic, et al. "Hydrogen Balmer alpha line shapes for hydrogen-argon mixtures in a low-pressure rf discharge." J. Appl. Phys., vol. 74, No. 11, Dec. 1993.

Rogers. "Cold Fusion Reaction Products and Their Measurement." *Journal of Fusion Technology*, vol. 9, No. 4, 1990.

Rogers. "Isotopic hydrogen fusion in metals." *Fusion Technology*, vol. 16, No. 2, Sep. 1989, pp. 2254-2259.

Rosenblum. "Celebrating Y2K Could Prevent Panic, Ease Transition." *Re: (ise-l) Institute for Social Ecology Newsletter*, Dec. 22, 1998.

Rosenblum. "Four Interviews With Dr. Randell Mills on New Energy, New Physics." *Re: (ise-l) Institute for Social Ecology Newsletter*, Feb. 2, 1998.

Rothwell. "Italy-Cold Fusion & Judge's Verdict." *NEN*, vol. 4, No. 1, Mar. 26, 1996, available at www.padrak.com/ine/CFLIBEL.html, pp. 9-11.

Rousseau. "Case Studies in Pathological Science." *American Scientist*, vol. 80, 1992, pp. 54-63.

Rout, et. al. "Phenomenon of Low Energy Emissions from Hydrogen/Deuterium Loaded Palladium." *3$^{rd}$ Annual Conference on Cold Fusion*, Oct. 21-25, 1992.

Rudd, et. al. "Backward Peak in the Electron Spectrum from Collisions of 70-keV Protons with a Target from a Hydrogen-Atom Source." *Physical Review Letters*, vol. 68, No. 10, Mar. 1992, pp. 1504-1506.

Salamon, et. al. "Limits . . . Electrolytic Cells." *Nature*, vol. 344, Mar. 29, 1990, pp. 401-405.

Schaefer. "Das Ultrarote Spektrum Des U-Zentrums," *Phys. Chem. Solids*, 1960, 12, pp. 233-244, Pergamon Press, Great Britain.

Schearer et al. "Microwave Saturation of Paraelectri-Resonance Transition of OH$^-$ Ions in Kcl:." *Solid State Communications*, vol. 4, 1966, pp. 639-642.

Schiff, Leonard I. "Quantum Mechanics." *Stanford University*, 1968, pp. 1, 7-8, 10-12, 21, 54-57, 60-61, 82-82. 101, 527.

Schrieder, et. al. "Search for Colid Nuclear Fusion in Palladium-Deuterium." *Z. Phys. B-Condensed Matter*, vol. 76, No. 2, 1989, pp. 141-142.

Service. "Cold Fusion: Still Going." *Newsweek Focus*, Jul. 19, 1993.

Shani, et. al. "Evidence for a Background Neutron Enhanced Fusion in Deuterium Absorbed Palladium." *Solid State Communications*, vol. 72, No. 1, 1989, pp. 53-57.

Shaubach, et. al. "Anomalous Heat . . . Carbonate." *Thermacore, Inc.*, pp. 1-10.

Shelton, et. al. "An assessment of claims of 'excess heat' in 'cold fusion' calorimetry." *Elsevier Science B.V., Thermomechanics Acta 297*, 1997, pp. 7-15.

Shermer, "Baloney Detection", *Scientific American*, Nov. 2001.

Shkedi, et. al. "Calorimetry, Excess Heat, and Faraday Efficiency in Ni-H$_2$O Electrolytic Cells." *Fusion Technology*, vol. 28, Nov. 1995, pp. 1720-1731.

Shook. "A Pragmatically Realistic Philosophy of Science." *Pragmatic Naturalism and Realism*. Prometheus Books: Amherst, NY. 2003.

Silvera, et. al. "Deuterated palladium at temperatures from 4.3 to 400K and pressures to 105 kbar; Search for cold fusion." *The American Physical Society*, vol. 42, No. 14, Nov. 15, 1990, pp. 9143-9146.

Souw et al., "Calculation of the Combined Zeeman and translational Stark Effect on the Hα-Multiplet", *Physica*, pp. 353-374, 1983.

Srianand, et. al. "The cosmic microwave background radiation temperature at a redshift of 2.34." *Nature*, vol. 40, Dec. 2000, pp. 931-935.

Srinivasan, et. al. "Tritium and Excess Heat Generation during Electrolysis of Aqueous Solutions of Alkali Salts with Nickel Cathode." *3$^{rd}$ Annual Conference on Cold Fusion*, Oct. 21-25, 1992.

Stein. "Theory May Explain Cold Fusion Puzzle." *Lexis Reprint, Washington News*, Apr. 25, 1991.

"Stellar Spectra and the Secrets of Starlight" (Internet Pages) www.kingusa.ab.ca/~brian/asto/course/lectures/fall/a200110g.htm (date and author unknown).

Stipp. "Georgia Group Outlines Errors That Led to Withdrawal of Cold Fusion Claims." *The Wall Street Journal*, Apr. 26, 1989, p. B4.

Storms, et. al. "Electrolytic Tritium Production." *Fusion Technology*, vol. 17, Jul. 1990, pp. 680-695.

Suplee. "Two New Theories on Cold Fusion . . . Scientists." *The Washington Post 1$^{st}$ Section*, 1991, p. A11.

Taubes. "Bad Science." *Random House*, 1993, pp. 303, 425-481.

Taubes. "Cold Fusion Conundrum at Texas A & M." *Science*, vol. 248, News & Comment, Jun. 15, 1990.

Taylor, et. al. "Search for neutrons from Deuterated palladium subject to high electrical currents." *Fourth International Conference on Cold Fusion*, Maui Hawaii, Dec. 6-9, 1993.

Technology Insights. "Drafts: Hydrocatalysis Technical Assessment." PACIFICORP, Aug. 1996.

Tegmark, et. al. "100 Years of Quantum Mysteries." *Scientific American*, Feb. 2001, pp. 68-75.

Thermacore, Inc. "SBIR Phase I Nascent Hydrogen: An Energy Source." Final Report, Mar. 1994.

Thomas. "Zur Photocjemie des KH-KBR Mischjristalles." *Annalen der Physik*, vol. 38, 1940, pp. 601-608.

Thorne, et. al. "Recombination during the Electrolysis of Light Water in 0.6 M K$_2$CO$_3$ Can It Account for the Reports of Excess Heat?" Departments of Physics and Chemistry, Brigham Young University, Jun. 1993.

Tolman, Richard C. "The Priniciples of Statistical Mechanics." *California Institute of Technology*, 1979, pp. 180-188.

Turner. "Declaration of Dr. Gary L. Turner." Aug. 24, 2004.

Vaselli et. al. "Screenin Effect of Impurities in Metals: A possible Explanation of the Process of Cold Nuclear Fusion." 11 Nuovo Cimento Della Societa Italiana di Fisica, vol. 11D, No. 6, Jun. 1989, Bologna, Italy, pp. 927-932.

Videnovic, et al. "Spectroscopic investigations of a cathode fall region of the Grimm-type glow discharge." *Spectrochimica Acta Part B*, vol. 51, 1996, pp. 1707-1731.

Vigier. "New Hydrogen Energies in Specially Structured Dense Media : Capillary Chemistry and Capillary Fusion." *Proceedings of the Third Annual Conf. on Cold Fusion*, Nagoya, Japan, Oct. 21-25, 1992, H. Ikegami, Ed. Universal Academy.

Vigier. "New Hydrogen (Deuterium) Bohr Orbits." *Proc. ICCF4*, vol. 4, 1994, p. 7-10.

Weisskopf, V.F. "Recent developments in the theory of the electron." *Reviews on Modern Physics*, vol. 21, No. 2, 1949, pp. 305-315.

Wheeler, et. al. "Quantum Theory and Measurement." Translation of Heisenburg's Uncertainty Principle Paper, *Zeitschrift für Physik*, 1927, vol. 43, pp. 172-198.

Williams. "Upper Bounds on Cold Fusion in Electrolytic Cells." *Nature*, vol. 342, Nov. 23, 1989, pp. 375-384.

Wilson, et. al. "Analysis of experiments on the calorimetry of LiOD-$D_2O$ electrochemical cells." *Elsevier Sequoia S.A.*, vol. 332, Aug. 14, 1992, pp. 1-31.

Yamaguchi et. al. "Direct Evidence . . . Palladium." *NTT Basic Research Laboratories*, 1992 pp. 1-10.

Ziegler, et. al. "Electrochemical Experiments in Cold Nuclear-Fusion." *Physical Review Letters*, vol. 62, No. 25, Jun. 19, 1989, pp. 2929-2932.

Zimmerman, Peter "An analysis of theoretical flaws in so-called classical quantum mechanics and of experimental evidence against CQM" (internet page) groups.yahoo.com/group/hydrino/files/analysis.rtf (date unknown).

Zweig, "Quark Catalysis of Exothermal Nuclear Reactions", Science, vol. 201, (1978), pp. 973-979.

R.L. Mills, K. Akhtar, B. Dhandapani, "Tests of Features of Field-Acceleration Models for the Extraordinary Selective H Balmer α Broadening in Certain Hydrogen Mixed Plasmas," Journal of Applied Physics, submitted. (Web Publication Date: Jun. 24, 2005.).

R.L. Mills, "Physical Solutions of the Nature of the Atom, Photon, and Their Interactions to Form Excited and Predicted Hydrino States," New Journal of Physics, submitted. (Web Publication Date: Jun. 9, 2005.).

R. L. Mills, J. He, Y. Lu, Z, M. Nansteel, Chang, B. Dhandapani, "Comprehensive Identification and Potential Applications of New States of Hydrogen," Central European Journal of Physics, submitted. (Web Publication Date: May 9, 2005.).

R. L. Mills, J. He, Z, Chang, W. Good, Y. Lu, B. Dhandapani, "Catalysis of Atomic Hydrogen to Novel Hydrogen Species H(1/4) and $H_2$(1/4) as a New Power Source," New J. Chem., submitted. (Web Publication Date: May 6, 2005.).

R. L. Mills, J. He, Z, Chang, W. Good, Y. Lu, B. Dhandapani, "Catalysis of Atomic Hydrogen to Novel Hydrides as a New Power Source," Prepr. Pap.—Am. Chem. Soc., Div. Fuel Chem 2005, 50(2). (Web Publication Date: Apr. 22, 2005.).

R. L. Mills, M. Nansteel, J. He, B. Dhandapani, "Low-Voltage EUV and Visible Light Source Due to Catalysis of Atomic Hydrogen," J. Plasma Physics, submitted. (Web Publication Date: Apr. 15, 2005.).

R. L. Mills, J. He, M. Nansteel, B. Dhandapani, "Catalysis of Atomic Hydrogen to New Hydrides as a New Power Source," International Journal of Global Energy Issues (IJGEI). Special Edition in Energy System, submitted. (Web Publication Date: Apr. 4, 2005.).

R. L. Mills, "Maxwells's Equations and QED: Which is Fact and Which is Fiction," Physica Scripta, submitted. (Web Publication Date: Oct. 28, 2004.).

R. L. Mills, "Exact Classical Quantum Mechanical Solution for Atomic Helium which Predicts Conjugate Parameters from a Unique Solution for the First Time," Foundations of Science, submitted. (Web Publication Date: Oct. 28, 2004.).

J. Phillips, C. K. Chen, R. L. Mills, "Evidence of Catalytic Production of Hot Hydrogen in RF-Generated Hydrogen/Argon Plasmas," J. Appl. Physics, submitted. (Web Publication Date: Sep. 7, 2004).

R. L. Mills, Y. Lu, M. Nansteel, J. He, A. Voigt, W. Good, B. Dhandapani, "Energetic Catalyst-Hydrogen Plasma Reaction as a Potential New Energy Source," Division of Fuel Chemistry, Session: Advances in Hydrogen Energy, 228th American Chemical Society National Meeting, Aug. 22-26, 2004, Philadelphia, PA.

R. L. Mills, Dhandapani, W. Good, J. He, "New States of Hydrogen Isolated from $K_2CO_3$ Electrolysis Gases," Electrochim. Acta, submitted. (Web Publication Date: Apr. 28, 2004.).

R. L. Mills, "Exact Classical Quantum Mechanical Solutions for One- through Twenty-Electron Atoms," Phys. Essays, submitted. (Web Publication Date: Apr. 22, 2004.).

R. L. Mills, Y. Lu, M. Nansteel, J. He, A. Voigt, B. Dhandapani, "Energetic Catalyst-Hydrogen Plasma Reaction as a Potential New Energy Source," Division of Fuel Chemistry, Session: Chemistry of Solid, Liquid, and Gaseous Fuels, 227th American Chemical Society National Meeting, Mar. 28-Apr. 1, 2004, Anaheim, CA.

R. Mills, B. Dhandapani, J. He, "Highly Stable Amorphous Silicon Hydride from a Helium Plasma Reaction," Materials Chemistry and Physics, submitted. (Web Publication Date: Nov. 17, 2003.).

R. L. Mills, Y. Lu, B. Dhandapani, "Spectral Identification of $H_2$(½)," submitted.

R. L. Mills, Y. Lu, J. He, M. Nansteel, P. Ray, X. Chen, A. Voigt, B. Dhandapani, "Spectral Identification of New States of Hydrogen,"New Journal of Chemistry, submitted. (Web Publication Date: Nov. 18, 2003.).

R. L. Mills, P. Ray, B. Dhandapani, "Evidence of an Energy Transfer Reaction Between Atomic Hydrogen and Argon II or Helium II as the Source of Excessively Hot H Atoms in RF Plasmas," Journal of Plasma Physics, in press. (Web Publication Date: Sep. 26, 2003.).

J. Phillips, C.K. Chen, R. L. Mills, "Evidence of the Production of Hot Hydrogen Atoms in RF Plasmas by Catalytic Reactions Between Hydrogen and Oxygen Species," Spectrochimica Acta Part B: Atomic Spectroscopy, submitted. (Web Publication Date: Sep. 12, 2003.).

R. L. Mills, P. Ray, B. Dhandapani, "Excessive Balmer α Line Broadening of Water-Vapor Capactively-Coupled RF Discharge Plasmas" IEEE Transactions on Plasma Science, submitted. (Web Publication Date: Aug. 18, 2003.).

R. L. Mills, "The Nature of the Chemical Bond Revisited and an Alternative Maxwellian Approach," Physics Essays, in press. (Web Publication Date: Aug. 6, 2003.).

R. L. Mills, P. Ray, M. Nansteel, J. He, X. Chen, A. Voigt, B. Dhandapani, "Energetic Catalyst-Hydrogen Plasma Reaction Forms a New State of Hydrogen," Doklady Physical Chemistry, submitted.

R. L. Mills, P. Ray, M. Nansteel, J. He, X. Chen, A. Voigt, B. Dhandapani, Luca Gamberale, "Energetic Catalyst-Hydrogen Plasma Reaction as a Potential New Energy Source," Central European Journal of Physics, submitted. (Web Publication Date: Jun. 6, 2003.).

R. Mills, P. Ray, "New H I Laser Medium Based on Novel Energetic Plasma of Atomic Hydrogen and Certain Group I Catalysts," J. Plasma Physics, submitted.

R. L. Mills, P. Ray, M. Nansteel, J. He, X. Chen, A. Voigt, B. Dhandapani, "Characterization of Energetic Catalyst-Hydrogen Plasma Reaction as a Potential New Energy Source," Am. Chem. Soc. Div. Fuel Chem. Prepr., vol. 48, No. 2, (2003).

R. Mills, P. C. Ray, M. Mayo, M. Nansteel, W. Good, P. Jansson, B. Dhandapani, J. He, "Hydrogen Plasmas Generated Using Certain Group I Catalysts Show Stationary Inverted Lyman Populations and Free-Free and Bound-Free Emission of Lower-Energy State Hydride," Fizika A, submitted.

R. Mills, J. Sankar, A. Voigt, J. He, P. Ray, B. Dhandapani, "Role of Atomic Hydrogen Density and Energy in Low Power CVD Synthesis of Diamond Films," Thin Solid Films, 478, (2005) 77-90. (Web Publication Date: Dec. 22, 2003.).

R. Mills, B. Dhandapani, M. Nansteel, J. He, P. Ray, "Liquid-Nitrogen-Condensable Molecular Hydrogen Gas Isolated from a Catalytic Plasma Reaction," J. Phys. Chem. B, submitted.

R. L. Mills, P. Ray, J. He, B. Dhandapani, M. Nansteel, "Novel Spectral Series from Helium-Hydrogen Evenson Microwave Cavity Plasmas that Matched Fractional-Principal-Quantum-Energy-Level Atomic and Molecular Hydrogen," European Journal of Physics, submitted. (Web Publication Date: Apr. 24, 2003.).

R. L. Mills, P. Ray, R. M. Mayo, "Highly Pumped Inverted Balmer and Lyman Populations," New Journal of Physics, submitted.

R. L. Mills, P. Ray, J. Dong, M. Nansteel, R. M. Mayo, B. Dhandapani, X. Chen, "Comparison of Balmer α Line Broadening and Power Balances of Helium-Hydrogen Plasma Sources," Braz. J. Phys., submitted. (Web Publication Date: Mar. 12, 2003.).

R. Mills, P. Ray, M. Nansteel, R. M. Mayo, "Comparison of Water-Plasma Sources of Stationary Inverted Balmer and Lyman Populations for a CW HI Laser," J. Appl. Spectroscopy, in preparation.

R. Mills, J. Sankar, P. Ray, J. He, A. Voigt, B. Dhandapani, "Synthesis and Characterization of Diamond Films from MPCVD of an Energetic Agron-Hydrogen Plasma and Methane," J. of Materials Research, submitted. (Web Publication Date: May 7, 2003.).

R. Mills, P. Ray, B. Dhandapani, W. Good, P. Jansson, M. Nansteel, J. He, A. Voigt, "Spectroscopic and NMR Identification of Novel Hydride Ions in Fractional Quantum Energy States Formed by an Exolthermic Reaction of Atomic Hydrogen with Certain Catalysts," European Physical Journal: Applied Physics, 28, (2004), 83-104. (Web Publication Date: Feb. 21, 2003.).

R. L. Mills, "The Fallacy of Feynman's Argument on the Stabilityof the Hydrogen Atom According to Quantum Mechanics," Annales de la Fondation Louis de Broglie, submitted. (Web Publication Date: Jan. 27, 2003.).

R. Mills, J. He, B. Dhandapani, P. Ray, "Comparison of Catalysts and Microwave Plasma Sources of Vibrational Spectral Emission of Fractional-Rydberg-State Hydrogen Molecular Ion," Canadian Journal of Physics, submitted.

R. L. Mills, P. Ray, X. Chen, B. Dhandapani, "Vibrational Spectral Emission of Fractional-Principal-Quantum-Energy-Level Molecular Hydrogen", J. of the Physical Society of Japan, submitted. (Web Publication Date: Sep. 9, 2002.).

J. Phillips, R. L. Mills, X. Chen, "Water Bath Calorimetric Study of Excess Heat in 'Resonance Transfer' Plasmas," J. Appl. Phys., vol. 96, No. 6, (2004) 3095-3012. (Web Publication Date: Jun. 16, 2003.).

R. L. Mills, P. Ray, B. Dhandapani, X. Chen, "Comparison of Catalysts and Microwave Plasma Sources of Spectral Emission of Fractional-Principal-Quantum-Energy-Level Atomic and Molecular Hydrogen," Journal of Applied Spectroscopy, submitted. (Web Publication Date: Feb. 12, 2002.).

R. L. Mills, P. Ray, B. Dhandapani, J. He, "Novel Liquid-Nitrogen-Condensable Molecular Hydrogen Gas," Acta Physica Polonica A, submitted. (Web Publication Date: Oct. 29, 2002.).

R. L. Mills, P. C. Ray, R. M. May, M. Nansteel, B. Dhandapani, J. Phillips, "Spectroscopic Study of Unique Line Broadening and Inversion in Low Pressure Microwave Generated Water Plasmas," Journal of Plasma Physics, in press. (Web Publication Date: Jun. 18, 2003.).

R. L. Mills, P. Ray, B. Dhandapani, J. He, "Energetic Helium-Hydrogen Plasma Reaction," AIAA Journal, submitted. (Web Publication Date: Jul. 26, 2002.).

R. L. Mills, P. Ray, M. Nansteel, P. C. Ray, "Bright Hydrogen-Light and Power Source due to a Resonant Energy Transfer with Strontium and Argon Ions," Vacuum, submitted.

R. L. Mills, P. Ray, B. Dhandapani, J. Dong, X. Chen, "Power Source Based on Helium-Plasma Catalysis of Atomic Hydrogen to Fractional Rydberg States," Contributions to Plasma Physics, submitted.

R. Mills, J. He, A. Echezuria, B Dhandapani, P. Ray, "Comparison of Catalysts and Plasma Sources of Vibrational Spectral Emission of Fractional-Rydberg-State Hydrogen Molecular Ion," The European Physical Journal Applied Physics, submitted. (Web Publication Date: Sep. 2, 2002.).

R. L. Mills, J. Sankar, A. Voigt, J. He, B. Dhandapani, "Spectroscopic Characterization of the Atomic Hydrogen Energies and Densities and Carbon Species During Helium-Hydrogen-Methane Plasma CVD Synthesis of Diamond Films," Chemistry of Materials, vol. 15, (2003), pp. 1313-1321. (Web Publication Date: Dec. 31, 2002.).

R. Mills, P. Ray, R. M. Mayo, "Stationary Inverted Balmer and Lyman Populations for a CW HI Water-Plasma Laser," IEEE Transactions on Plasma Science, submitted. (Web Publication Date: Aug. 16, 2002.).

R. L. Mills, P. Ray, B. Dhandapani, J. He, "Extreme Ultraviolet Spectroscopy of Helium-Hydrogen Plasma," J. Phys. D, vol. 36, (2003), pp. 1535-1542. (Web Publication Date: Jul. 17, 2002.).

R. L. Mills, P. Ray, "Spectroscopic Evidence for a Water-Plasma Laser," Europhysics Letters, submitted. (Web Publication Date: Sep. 19, 2002.).

R. Mills, P. Ray."Spectroscopic Evidence for Highly Pumped Balmer and Lyman Populations in a Water-Plasma," J. of Applied Physics, submitted. (Web Publication Date: Sep. 18, 2002.).

R. L. Mills, J. Sankar, A. Voigt, J. He, B. Dhandapani, "Low Power MPCVD of Diamond Films on Silicon Substrates," Journal of Vacuum Science & Technology A, submitted. (Web Publication Date: Jun. 26, 2002.).

R. L. Mills, X. Chen, P. Ray, J. He, B. Dhandapani, "Plasma Power Source Based on a Catalytic Reaction of Atomic Hydrogen Measured by Water Bath Calorimetry," Thermochimica Acta, vol. 406, Issue 1-2, (2003), pp. 35-53. (Web Publication Date: Jun. 25, 2002.).

R. L. Mills, A. Voigt, B. Dhandapani, J. He, "Synthesis and Spectroscopic Identification of Lithium Chloro Hydride," Materials Characterization, submitted.

R. L. Mills, B. Dhandapani, J. He, "Highly Stable Amorphous Silicon Hydride," Solar Energy Materials & Solar Cells, vol. 80, (2003), pp. 1-20. (Web Publication Date: Apr. 15, 2002.).

R. L. Mills, J. Sankar, A. Voigt, J. He, B. Dhandapani, "Synthesis of HDLC Films from Solid Carbon," Journal of Materials Science, in press. (Web Publication Date: May 3, 2002.).

R. Mills, P. Ray, R. M. Mayo, "The Potential for a Hydrogen Water-Plasma Laser," Applied Physics Letters, vol. 82, No. 11, (2003), pp. 1679-1681. (Web Publication Date: Jul. 11, 2002.).

R. L. Mills, "Classical Quantum Mechanics," Physics Essays, vol. 16, (2003) 433-498. (Web Publication Date: May 23, 2002.).

R. L. Mills, P. Ray, Spectroscopic Characterization of Stationary Inverted Lyman Populations and Free-Free and Bound-Free Emission of Lower-Energy State Hydride Ion Formed by a Catalytic Reaction of Atomic Hydrogen and Certain Group I Catalysts, Quantitative Spectroscopy and Radiative Transfer, No. 39, sciencedirect.com, Apr. 17, 2003.

R. M. Mayo, R. Mills, "Direct Plasmadynamic Conversion of Plasma Thermal Power to Electricity for Microdistributed Power Applications," 40th Annual Power Sources Conference, Cherry Hill, NJ, Jun. 10-13, 2002, pp. 1-4. (Web Publication Date: Mar. 28, 2002.), R. Mills, P. Ray, R. M. Mayo, "Chemically-Generated Stationary Inverted Lyman Population for a CW HI Laser," European J of Phys. D., submitted. (Web Publication Date: Apr. 22, 2004.).

R. L. Mills, P. Ray, "Stationary Inverted Lyman Population Formed from Incandescently Heated Hydrogen Gas with Certain Catalysts," J. Phys. D, Applied Physics, vol. 36, (2003), pp. 1504-1509. (Web Publication Date: Mar. 20, 2002.).

R. Mills, "A Maxwellian Approach to Quantum Mechanics Explains the Nature of Free Electrons in Superfluid Helium," Low Temp. Phys., submitted. (Web Publication Date: Jun. 4, 2002.).

R. Mills and M. Nansteel, P. Ray, "Bright Hydrogen-Light Source due to a Resonant Energy Transfer with Strontium and Argon Ions," New Journal of Physics, vol. 4, (2002), pp. 70.1-70.28. (Web Publication Date: Oct. 2002, when it became available on the New Journal of Physics website.).

R. Mills, P. Ray, R. M. Mayo, "CW HI Laser Based on a Stationary Inverted Lyman Population Formed from Incancdescently Heated Hydrogen Gas with certain Group I Catalysts," IEEE Transactions on Plasma Science, vol. 31, No. 2, (2003), pp. 236-247. (Web Publication Date: Feb. 4, 2002.).

R. L. Mills, P. Ray, J. Dong, M. Nansteel, B. Dhandapani, J. He, "Spectral Emission of Fractional-Principal-Quantum-Energy-Level Atomic and Molecular Hydrogen," Vibrational Spectroscopy, vol. 31, No. 2, (2003), pp. 195-213.

R. L. Mills, P. Ray, E. Dayalan, B. Dhandapani, J. He, "Comparison of Excessive Balmer α Line Broadening of Inductively and Capacitively Coupled RF, Microwave, and Glow Discharge Hydrogen Plasmas with Certain Catalysts," IEEE Transactions on Plasma Science, vol. 31, No. 3, (2003), pp. 338-355. (Web Publication Date: Sep. 17, 2002.).

R. M. Mayo, R. Mills, "Direct Plasmadynamic Conversion of Plasma Thermal Power to Electricity," IEEE Transactions on Plasma Science, Oct. 2002, vol. 30, No. 5, pp. 2066-2073. (Web Publication Date: Mar. 26, 2002.).

H. Conrads, R. Mills, Th. Wrubel, "Emission in the Deep Vacuum Ultraviolet from a Plasma Formed by Incandescently Heating Hydrogen Gas with Trace Amounts of Potassium Carbonate," Plasma Sources Science and Technology, vol. 12, (2003), pp. 389-395.

R. L. Mills, P. Ray, "Stationary Inverted Lyman Population and a Very Stable Novel Hydride Formed by a Catalytic Reaction of Atomic Hydrogen and Certain Catalysts," Opt. Mater, in press.

R. L. Mills, J. He, P. Ray, B. Dhandapani, X. Chen, "Synthesis and Characterization of a Highly Stable Amorphous Silicon Hydride as the Product of a Catalytic Helium-Hydrogen Plasma Reaction," Int. J. Hydrogen Energy, vol. 28, No. 12, (2003), pp. 1401-1424. (Web Publication Date: Apr. 15, 2002.).

R. L. Mills, A. Voigt, B. Dhandapani, J. He, "Synthesis and Characterization of Lithium Chloro Hydride," Int. J. Hydrogen Energy, submitted. (Web Publication Date: Jan. 7, 2002.).

R. L. Mills, P. Ray, "Substantial Changes in the Characteristics of a Microwave Plasma Due to Combining Argon and Hydrogen," New Journal of Physics, www.njp.org, vol. 4, (2002), pp. 22.1-22.17. (Web Publication Date: Dec. 27, 2001.).

R. L. Mills, P. Ray, "A Comprehensive Study of Spectra of the Bound-Free Hyperfine Levels of Novel Hydride Ion $H^-(½)$, Hydrogen, Nitrogen, and Air," Int. J. Hydrogen Energy, vol. 28, No. 8, (2003), pp. 825-871. (Web Publication Date: Nov. 14, 2001.).

R. L. Mills, E. Dayalan, "Novel Alkali and Alkaline Earth Hydrides for High Voltage and High Energy Density Batteries," Proceedings of the 17th Annual Battery Conference on Applications and Advances, California State University, Long Beach, CA, (Jan. 15-18, 2002), pp. 1-6. (Web Publication Date: Nov. 9, 2001.).

R. M. Mayo, R. Mills, M. Nansteel, "On the Potential of Direct and MHD Conversion of Power from a Novel Plasma Source to Electricity for Microdistributed Power Applications," IEEE Transactions on Plasma Science, Aug. 2002, vol. 30, No. 4, pp. 1568-1578. (Web Publication Date: Nov. 12, 2001.).

R. Mills, P. C. Ray, R. M. Mayo, M. Nansteel, W. Good, P. Jansson, B. Dhandapani, J. He, "Stationary Inverted Lyman Populations and Free-Free and Bound-Free Emission of Lower-Energy State Hydride Ion Formed by an Exothermic Catalytic Reaction of Atomic Hydrogen and Certain Group I Catalysts," J. Phys. Chem. A, submitted. (Web Publication Date: Nov. 13, 2001.).

R. Mills, E. Dayalan, P. Ray, B. Dhandapani, J. He, "Highly Stable Novel Inorganic Hydrides from Aqueous Electrolysis and Plasma Electrolysis," Electrochimica Acta, vol. 47, No. 24, (2002), pp. 3909-3926. (Web Publication Date: Jun. 13, 2002.).

R. L. Mills, P. Ray, B. Dhandapani, R. M. Mayo, J. He, "Comparison of Excessive Balmer α Line Broadening of Glow Discharge and Microwave Hydrogen Plasmas with Certain Catalysts," J. of Applied Physics, (2002), vol. 92, No. 12, pp. 7008-7022. (Web Publication Date: Oct. 9, 2002.).

R. L. Mills, P. Ray, B. Dhandapani, J. He, "Emission Spectroscopic Identification of Fractional Rydberg States of Atomic Hydrogen Formed by a Catalytic Helium-Hydrogen Plasma Reaction," Vacuum, submitted. (Web Publication Date: Oct. 9, 2001.).

R. L. Mills, P. Ray, B. Dhandapani, M. Nansteel, X. Chen, J. He, "New Power Source from Fractional Rydberg States of Atomic Hydrogen," Current Appl. Phys., submitted. (Web Publication Date: Oct. 9, 2001.).

R. L. Mills, P. Ray, B. Dhandapani, M. Nansteel, X. Chen, J. He, "Spectroscopic Identification of Tanstitions of Fractional Rydberg States of Atomic Hydrogen," J. of Quantitative Spectroscopy and Radiative Transfer, in press. (Web Publication Date: Oct. 9, 2001.).

R. L. Mills, P. Ray, B. Dhandapani, M. Nansteel, X. Chen, J. He, "New Power Source from Fractional Quantum Energy Levels of Atomic Hydrogen that Surpasses Internal Combustion," J Mol. Struct., vol. 643, No. 1-3, (2002), pp. 43-54. (Web Publication Date: Oct. 10, 2001.).

R. L. Mills, P. Ray, "Spectroscopic Identification of a Novel Catalytic Reaction of Rubidium Ion with Atomic Hydrogen and the Hydride Ion Product," Int. J. Hydrogen Energy, vol. 27, No. 9, (2002), pp. 927-935. (Web Publication Date: Sep. 19, 2001.).

R. Mills, J. Dong, W. Good, P. Ray, J. He, B. Dhandapani, "Measurement of Energy Balances of Noble Gas-Hydrogen Discharge Plasmas Using Calvet Calorimetry," Int. J. Hydrogen Energy, vol. 27, No. 9, (2002), pp. 967-978. (Web Publication Date: Sep. 14, 2001.).

R. L. Mills, A. Voigt, P. Ray, M. Nansteel, B. Dhandapani, "Measurement of Hydrogen Balmer Line Broadening and Thermal Power Balances of Noble Gas-Hydrogen Discharge Plasmas," Int. J. Hydrogen Energy, vol. 27, No. 6, (2002), pp. 671-685. (Web Publication Date: Aug. 22, 2001.).

R. Mills, P. Ray, "Vibrational Spectral Emission of Fractional-Principal-Quantum-Energy-Level Hydrogen Molecular Ion," Int. J. Hydrogen Energy, vol. 27, No. 5, (2002), pp. 533-564. (Web Publication Date: Jul. 19, 2001.).

R. Mills, P. Ray, "Spectral Emission of Fractional Quantum Energy Levels of Atomic Hydrogen from a Helium-Hydrogen Plasma and the Implications for Dark Matter," Int. J. Hydrogen Energy, (2002), vol. 27, No. 3, pp. 301-322. (Web Publication Date: Aug. 1, 2001.).

R. Mills, P. Ray, "Spectroscopic Identification of a Novel Catalytic Reaction of Potassium and Atomic Hydrogen and the Hydride Ion Product," Int. J. Hydrogen Energy, vol. 27, No. 2, (2002), pp. 183-192. (Web Publication Date: Jan. 11, 2002.).

R. Mills, "BlackLight Power Technology—A New Clean Hydrogen Energy Source with the Potential for Direct Conversion to Electricity," Proceedings of the National Hydrogen Association, 12 th Annual U.S. Hydrogen Meeting and Exposition, *Hydrogen: The Common Thread*, The Washington Hilton and Towers, Washington DC, (Mar. 6-8, 2001), pp. 671-697, (Presented at the conference on Mar. 7, 2001; Web Publication Date: Apr. 20, 2001.).

R. Mills, W. Good, A. Voigt, Jinquan Dong, "Minimum Heat of Formation of Potassium Iodo Hydride," Int. J. Hydrogen Energy, vol. 26, No. 11, (2001), pp. 1199-1208. (Web Publication Date: Mar. 23, 2001.).

R. Mills, "Spectroscopic Identification of a Novel Catalytic Reaction of Atomic Hydrogen and the Hydride Ion Product," Int. J. Hydrogen Energy, vol. 26, No. 10, (2001), pp. 1041-1058. (Web Publication Date: Mar. 23, 2001.).

R. Mills, N. Greenig, S. Hicks, "Optically Measured Power Balances of Glow Discharges of Mixtures of Argon, Hydrogen, and Potassium, Rubidium, Cesium, or Strontium Vapor," Int. J. Hydrogen Energy, vol. 27, No. 6, (2002), pp. 651-670. (Web Publication Date: Jul. 20, 2001.).

R. Mills, "The Grand Unified Theory of Classical Quantum Mechanics," Global Foundations, Inc. Orbis Scientiae entitied *The Role of Attractive and Repulsive Gravitational Forces in Cosmic Accerleration of Particles The Origin of the Cosmic Gamma Ray Bursts*, (29th Conference on High Energy Physics and Comology Since 1964) Dr. Behram N. Kursunoglu, Chairman, Dec. 14-17, 2000, Lago Mar Resort, Fort Lauderdale, FL, Kluwer Academic/Plenum Publishers, New York, pp. 243-258. (Presented at the conference on Dec. 15, 2000; Web Publication Date: May 17, 2001.).

R. Mills, "The Grand Unified Theory of Classical Quantum Mechanics," Int. J. Hydrogen Energy, vol. 27, No. 5, (2002), pp. 565-590. (Web Publication Date: Sep. 17, 2001.).

R. Mills, M. Nansteel, P. Ray, "Argon-Hydrogen-Strontium Discharge Light Source," IEEE Transactions on Plasma Science, vol. 30, No. 2, (2002), pp. 639-653. (Web Publication Date: Dec. 7, 2000.).

R. Mills, B. Dhandapani, M. Nansteel, J. He, A. Voigt, "Identification of Compounds Containing Novel Hydride Ions by Nuclear Magnetic Resonance Spectroscopy," Int. J. Hydrogen Energy, vol. 26, No. 9, (2001), pp. 965-979. (Web Publication Date: Mar. 22, 2001.).

R. Mills, "BlackLight Power Technology—A New Clean Energy Source with the Potential for Direct Conversion to Electricity," Global Foundation International Conference on "Global Warming and Energy Policy," Dr. Behram N. Kursunoglu, Chairman, Fort Lauderdale, FL, Nov. 26-28, 2000, Kluwer Academic/Plenum Publishers, New York, pp. 187-202. (Presented at the conference on Nov. 26, 2000; Web Publication Date: Jan. 19, 2001.).

R. Mills, "The Nature of Free Electrons in Superfluid Helium—a Test of Quantum Mechanics and a Basis to Review its Foundations and Make a Compromised to Classical Theory," Int. J. Hydrogen Energy, vol. 26, No. 10, (2001), pp. 1059-1096. (Web Publication Date: Dec. 11, 2000.).

R. Mills, M. Nansteel, and Y. Lu, "Excessively Bright Hydrogen-Strontium Plasma Light Source Due to Energy Resonance of Strontium with Hydrogen," J. of Plasma Physics, vol. 69, (2003), pp. 131-158. (Web Publication Date: Aug. 27, 2001.).

R. Mills, J. Dong, Y. Lu, "Observation of Extreme Ultraviolet Hydrogen Emission from Incandescently Heated Hydrogen Gas with Certain Catalysts," Int. J. Hydrogen Energy, vol. 25, (2000), pp. 919-943. (Web Publication Date: Jun. 27, 2000.).

R. Mills, "Observation of Extreme Ultraviolet Emission from Hydrogen-Kl Plasmas Produced by a Hollow Cathode Discharge," Int. J. Hydrogen Energy, vol. 26, No. 6, (2001), pp. 579-592. (Web Publication Date: Jul. 10, 2000.).

R. Mills, "Temporal Behavior of Light-Emission in the Visible Spectral Range from a Ti-K2CO3-H-Cell," Int. J. Hydrogen Energy, vol. 26, No. 4, (2001), pp. 327-332. (Web Publication Date: Jul. 10, 2000.).

R. Mills, T. Onuma, and Y. Lu, "Formation of a Hydrogen Plasma from an incandescently Heated Hydrogen-Catalyst Gas Mixture with an Anomalous Afterglow Duration," Int. J. Hydrogen Energy, vol. 26, No. 7, Jul. 2001, pp. 749-762. (Web Publication Date: Jun. 28, 2000.).

R. Mills, M. Nansteel, and Y. Lu, "Observation of Extreme Ultraviolet Hydrogen Emission from Incandescently Heated Hydrogen Gas with Strontium that Produced an Anomalous Optically Measured Power Balance," Int. J. Hydrogen Energy, vol. 26, No. 4, (2001), pp. 309-326. (Web Publication Date: Jun. 27, 2000.).

R. Mills, B. Dhandapani, N. Greenig, J. He, "Synthesis and Characterization of Potassium Iodo Hydride," Int. J. of Hydrogen Energy, vol. 25, Issue 12, Dec. 2000, pp. 1185-1203. (Web Publication Date: Nov. 12, 2001.).

R. Mills, "Novel Inorganic Hydride," Int. J. of Hydrogen Energy, vol. 25, (2000), pp. 669-683. (Web Publication Date: Jun. 28, 2000.).

R. Mills, B. Dhandapani, M. Nansteel, J. He, T. Shannon, A. Echezuria, "Synthesis and Characterization of Novel Hydride Compounds," Int. J. of Hydrogen Energy, vol. 26, No. 4, 2001, pp. 339-367. (Web Publication Date: Jun. 13, 2001.).

R. Mills, "Highly Stable Novel Inorganic Hydrides," Journal of New Materials for Electrochemical Systems, vol. 6, (2003), pp. 45-54. (Web Publication Date: Nov. 20, 2001.).

R. Mills, "Novel Hydrogen Compounds from a Potassium Carbonate Electrolytic Cell," Fusion Technology, vol. 37, No. 2, Mar. 2000, pp. 157-182. (Web Publication Date: Jun. 26, 2000.).

R. Mills, "The Hydrogen Atom Revisited," Int. J. of Hydrogen Energy, vol. 25, Issue 12, Dec. 2000, pp. 1171-1183. (Web Publication Date: Jun. 27, 2000.).

Mills, R., Good, W., "Fractional Quantum Energy Levels of Hydrogen," Fusion Technology, vol. 28, No. 4, Nov. 1995, pp. 1697-1719. (Web Publication Date: Nov. 1, 2001.).

Mills, R., Good, W., Shaubach, R., "Dihydrino Molecule Identification," Fusion Technology, vol. 25, 103 (1994). (Web Publication Date: Apr. 11, 2001.).

R. Mills and S. Kneizyz, Fusion Technol. vol. 20, 65 (1991). (Web Publication Date: Apr. 11, 2001.).

R. Mills, *The Grand Unified Theory of Classical Quantum Mechanics*, Sep. 2001 Edition, BlackLight Power, Inc., Cranbury, New Jersey, Distributed by Amazon.com; Jul. 2003 Edition posted at www.blacklightpower.com.

Mills, "Author's response 'A possible trick of Hydride atom'." *International Journal of Hydrogen Energy*, vol. 26, 2001, p. 1225.

Mills."Author's response to 'Hydrino atom: novel chemistry or invalid physics'." *International Journal of Hydrogen Energy*, vol. 26, 2001, pp. 1233.

Mills."Author's response to 'Hydrino theory—a proposed amendment'." *International Journal of Hydrogen Energy*, vol. 26, 2001, pp. 1229-1231.

Mills. "BlackLight Power Technology: A New Clean Energy Source with the Potential for Direct Conversion to Electricity." *International Conference on Global Warning and Energy Policy*, Ft. Lauderdale, Florida, Nov. 26-28, 2000. Internet Publication Jan. 19, 2001.

Mills, "Classical Quantum Mechanics." Physica Scripta, submitted.

Mills. "The Grand Unified Theory of Classical Quantum Mechanics." pp. 1-9.

Mills, "The Grand Unified Theory of Classical Quantum Mechanics," (2001), Distributed by Amazon.com.

Mills. "Hydro catalysis Power Technology." *Statement of Dr. Randell L. Mills*, May 1993.

Mills, "A Maxwellian Approach to Quantum Mechanics Explains the Nature of Free Electrons in Superfluid Helium." Foundations of Science, submitted. Internet Publication Date Jun. 4, 2002.

Mills."Power Spectrum of the Cosmic Microwave Background" *BlackLight Power, Inc.* 2001.

Mills. "Spectral Emission of Fractional Quantum Energy Levels of Atomic Hydrogen from a Helium-Hydrogen Plasma and the implications for Dark Matter." *International Journal of Hydrogen Energy*, vol. 27, 2002, pp. 301-322. Internet Publication Aug. 1, 2001.

Mills, "Spectroscopic Identification of a Novel Catalytic Reaction of Atomic Hydrogen and the Hydride Ion Product," Int. J. Hydrogen Energy, vol. 26, No. 10, (2001), pp. 1041-1058. (Web Publication Date: Mar. 23, 2001.).

Mills. "Unification of Spacetime, the Forces, Matter, Energy, Hydro catalysis Power Corporation." 1992, pp. 53-84.

Mills, et. al. "Anomalous Argon-Hydrogen-Strontium Discharge." *IEEE Transactions of Plasma Science*, submitted.

Mills et al., "Chemically-Generated Stationary Inverted Lyman Population for a CW HI Laser," European J of Phys. D, submitted. (Web Publication Date: Apr. 22, 2002.).

Mills, et. al. "Comparison of Excessive Balmer Line Broadening of Glow Discharge and Microwave Hydrogen Plasmas with Certain Catalysts." *Chemical* Physics. Submitted. Internet Publication Date Sep. 17, 2002.

Mills, et. al. "CVD Synthesis of Single Crystal Diamond Films on Silicon Substrates Without Seeding." Diamond and Related Materials, submitted. Internet Publication Date Jun. 26, 2002.

Mills, et. al. "Direct Plasmadynamic Conversion of Plasma Thermal Power to Electricity." IEEE Transactions on Plasma Science, submitted. Internet Publication Date Mar. 26, 2002.

Mills et al., "Energetic Catalyst-Hydrogen Plasma Reaction as a Potential New Energy Source," European Physical Journal D, submitted. (Web Publication Date: Jun. 6, 2003.).

Mills, et. al. "Excess Heat Production . . . Cold Fusion." *Fusion Technology*, vol. 20, Feb. 1991, pp. 65-81.

Mills, et. al. "Excessive Balmer Line Broadening, Power Balance, and Novel Hydride Ion Product of Plasma Formed from Incandescently Heated Hydrogen Gas with Certain Catalysts." *International Journal of Hydrogen Energy*. Submitted.

Mills, "The Fallacy of Feynman's Argument on the Stability of the Hydrogen Atom According to Quantum Mechanics," Annales De La Fondation Louis DeBroglie, submitted. (Web Publication Date: Jan. 27, 2003.).

Mills, et. al. "Highly Stable Amorphous Silicon Hydride" J of Materials Research, submitted. Internet Publication Date Apr. 15, 2002.

Mills, et. al. "High Resolution Spectoscopic Observation of the Bound-Free Hyperfine Levels of a Novel Hydride Ion Corresponding to a Fractional Rydberg State of Atomic Hydrogen," *International Journal of Hydrogen Energy*, in press.

Mills et al., "Liquid-Nitrogen-Condensable Molecular Hydrogen Gas Isolated form a Catalytic Plasma Reaction," J. Phys. Chem. B, submitted.

Mills, et. al. "New Energy States of Atomic Hydrogen Formed in a Catalytic Helium-Hydrogen Plasma." IEEE Transactions on Plasma Science, submitted. Internet Publication Date Jul. 17, 2002.

Mills, et. al. "Plasma Power Source Based on a Catalytic Reaction of Atomic Hydrogen." Fuels and Energy, submitted.

Mills, et. al. "The Potential for an Extremely versatile Hydrogen Water-Plasma Laser." Phys. Rev. E, submitted.

Mills, et. al. "Spectroscopic Characterization of Stationary Inverted Lyman Populations and Free-Free and Bound-Free Emission of Lower-Energy State Hydride Ion Formed by a Catalytic Reaction of Atomic Hydrogen and Certain Group I Catalysts, Quantitative Spectroscopy and Radiative." Submitted.

Mills, et. al. "Spectroscopic Identification of Fractional Rydberg States of Atomic Hydrogen." *Journal of Physical Chemistry* (letter), Submitted.

Mills, et. al. "Spectroscopic Identification of Fractional Rydberg States of Atomic Hydrogen Formed by a Catalytic Helium-Hydrogen Plasma Reaction." Spectrochimica Acta B, submitted. Internet Publication Date Jul. 26, 2002.

Mills, et. al. "Spectroscopic Identification of Transitions of Fractional Rydberg States of Atomic Hydrogen." *Quantitative Spectroscopy and Energy Transfer*, Submitted. Internet Publication Date Oct. 9, 2001.

Mills, et. al. "Stationary Inverted Lyman Population Formed from Incandescently Heated Hydrogen Gas with Certain Catalysts", *Chemical Physics Letts*. submitted. Internet Publication Date Mar. 20, 2002.

Mills, et. al. "Synthesis and Characterization of a Highly Stable Amorphous Silicon Hydride", *International Journal of Hydrogen Energy*, submitted. Internet Publication Date Apr. 15, 2002.

Mills, et. al. "Synthesis of Diamond Films form Solid Carbon." Diamond and Related Materials, submitted.

Mills, et. al. "Water-Plasma Medium for a Hydrogen Laser." J of Phys. Chem. Lett., submitted.

Mills Technologies. "1KW Heat Exchanger System." *Thermacore, Inc.*, Oct. 11, 1991, pp. 1-6.

Mills Technologies. "1KW Heat Exchanger System." *Thermacore, Inc.*, Apr. 16, 1992, pp. 1-6.

K. Akhtar, J. Scharer, R. Mills, "Substantial Dopple Broadening of Atomic-Hydrogen Lines in DC and Capactively Coupled RF Plasmas," Dept. of Elect. and Computer Engineering, U of Wisc-Madison, WI 53706.

R. Mills, H. Zea, J. He, B. Dhandapani, "Water Bath Calorimetry on a Catalytic Reaction of Atomic Hydrogen," submitted.

R. Mills, "Physical Solutions of the Nature of the Atom, Photon, and Their Interactions to Form Excited and Predicted Hydrino States", New Journal of Physics, submitted.

R. L. Mills, "Exact Classical Quantum Mechanical Solution for Atomic Helium Which Predicts Conjugate Parameters from a Unique Solution for the First Time", Annales de la Fondation Louis de Broglie, submitted.

R. L. Mills, "Exact Classical Quantum Mechanical Solutions for One- Through Twenty-Electron Atoms", Physics Essays, submitted.

R. Mills, B. Dhandapani, J. He, "Highly Stable Amorphous Silicon Hydride from Helium Plasma Reactions", Materials Chemistry and Physics, 94, pp. 298-302 (2005).

R. L. Mills, P. C. Ray, R. M. Mayo, M. Nansteel, B. Dhandapani, J. Phillips, "Spectroscopic Study of Unique Line Broadening and Inversion in Low Pressure Microwave Generated Water Plasmas," Journal of Plasma Physics, vol. 1, Part 6, (2005), 877-888. (Web Publication Date: Jun. 18, 2003.).

R. L. Mills, "The Fallacy of Feynman's Argument on the Stability of the Hydrogen According to Quantum Mechanics," Annales de la Fondation Louis de Broglie, vol. 30, (2005), pp. 129-151. (Web Publication Date: Jan. 27, 2003.).

R. L. Mills, "The Nature of the Chemical Bond Revisited and an Alternative Maxwell Approach," Physics Essays, vol. 17, (2004), 342-389. (Web Publication Date: Aug. 6.).

U.S. Appl. No. 10/513,026, filed Nov. 1, 2004.
U.S. Appl. No. 10/494,571, filed May 6, 2004.
U.S. Appl. No. 10/469,913, filed Sep. 5, 2003.
U.S. Appl. No. 10/331,725, filed Dec. 31, 2002.
U.S. Appl. No. 10/319,460, filed Nov. 27, 2002.
U.S. Appl. No. 09/669,877, filed Sep. 27, 2000.
U.S. Appl. No. 09/813,792, filed Mar. 22, 2001.
U.S. Appl. No. 09/513,768, filed Feb. 25, 2000.
U.S. Appl. No. 09/678,730, filed Oct. 4, 2000.
U.S. Appl. No. 09/362,693, filed Jul. 29, 1999.
U.S. Appl. No. 09/181,180, filed Oct. 28, 1998.
U.S. Appl. No. 09/225,687, filed Jan. 6, 1999.
U.S. Appl. No. 09/110,717, filed Jul. 7, 1998.
U.S. Appl. No. 09/110,694, filed Jul. 7, 1998.
U.S. Appl. No. 09/501,622, filed Feb. 9, 2000.
U.S. Appl. No. 09/501,621, filed Feb. 9, 2000.
U.S. Appl. No. 09/111,003, filed Jul. 7, 1998.
U.S. Appl. No. 09/111,160, filed Jul. 7, 1998.
U.S. Appl. No. 09/110,678, filed Jul. 7, 1998.
U.S. Appl. No. 09/009,455, filed Jan. 20, 1998.
U.S. Appl. No. 09/009,294, filed Jan. 20, 1998.
U.S. Appl. No. 09/008,947, filed Jan. 20, 1998.
U.S. Appl. No. 09/009,837, filed Jan. 20, 1998.
U.S. Appl. No. 08/467,051, filed Jun. 6, 1995.
U.S. Appl. No. 08/467,911, filed Jun. 6, 1995.
U.S. Appl. No. 08/416,040, filed Apr. 3, 1995.
U.S. Appl. No. 08/107,357, filed Aug. 16, 1993.
U.S. Appl. No. 08/075,102, filed Jun. 11, 1993.
U.S. Appl. No. 07/825,845, filed Jan. 28, 1992.
U.S. Appl. No. 07/626,496, filed Dec. 12, 1990.
U.S. Appl. No. 07/345,628, filed Apr. 28, 1989.
U.S. Appl. No. 07/341,733, filed Apr. 21, 1989.

* cited by examiner

METHOD AND SYSTEM OF COMPUTING AND RENDERING THE NATURE OF THE CHEMICAL BOND OF HYDROGEN-TYPE MOLECULES AND MOLECULAR IONS

This application claims priority to U.S. Provisional Patent Application Nos. 60/488,622, filed Jul. 21, 2003; 60/491,963, filed Aug. 4, 2003; 60/534,112, filed Jan. 5, 2004; 60/542,278, filed Feb. 9, 2004; and 60/571,667, filed May 17, 2004, the complete disclosures of which are incorporated herein by reference.

I. INTRODUCTION

1. Field of the Invention

This invention relates to a method and system of physically solving the charge, mass, and current density functions of hydrogen-type molecules and molecular ions and computing and rendering the nature of the chemical bond using the solutions. The results can be displayed on visual or graphical media. The display can be static or dynamic such that vibration and rotation can be displayed in an embodiment. The displayed information is useful to anticipate reactivity and physical properties. The insight into the nature of the chemical bond can permit the solution and display of other molecules and provide utility to anticipate their reactivity and physical properties.

The quantum mechanical theory of the nature of the chemical bond is based on phenomena that are "unique to quantum mechanics" and have no basis in experimental observation. The current methods of arriving at numbers that are meant to reproduce and possibly predict new experimental results on bonds and spectra can be classified as a plethora of curving-fitting algorithms, often computer-programmed, that have no basis in reality and are not representative of the corresponding real molecules or molecular ions. Specifically, they all depend on the nonexistent, nonphysical "exchange integral" that is a consequence of a postulated linear combination of product wavefunctions wherein it is implicit that each point electron with infinite self-electric-and-magnetic-field energies must exist as a "probability-wave cloud" and be in two places at the same time (i.e. centered on two nuclei simultaneously!) The exchange integral is a "spooky action" phenomenon that violates Einstein causality. A further nonphysical aspect is that the molecular solution is obtained without considering the nuclei to move under the Born-Oppenheimer approximation; yet, the molecule must have a further nonphysical perpetual-motion-type property of "zero point vibration." Additional internal inconsistencies arise. The electron clouds mutually shield the nuclear charge to provide an adjustable parameter, "effective nuclear charge"; yet, neither has any self shielding effect even though the clouds are mutually indistinguishable and must classically result in a self interaction instability. The corresponding self-interaction energy term as well as the equally large electron-spin pairing energy are conspicuously absent from the Hamiltonian. Instead arbitrary types of variational parameters of the wavefunctions and mixing of wavefunctions as well as other adjustable parameters are introduced to force the solutions of a multitude of methods to more closely approximate the experimental parameters. Yet, the experimental bond energy is not calculated; rather a parameter $D_e$ is determined from which the "zero point vibration" is subtracted and "anharmonicity term in the zero-point vibration" is added to obtain the experimentally measurable bond energy $D_o$.

Zero point vibration (ZOV), like the similar nonsensical prediction of quantum mechanics, zero-point energy of the vacuum, has never been directly measured. Furthermore, ZOV violates the second law of thermodynamics, and it is in conflict with direct experimental results such as the formation of solid hydrogen and Bose-Einstein condensates of molecules. As a consequence, the bond energy predictions of quantum mechanics have never been tested experimentally, and it is not possible to state that the methods predict the experimental bond energy at all. The many conflicting attempts suffer from the same short comings that plague atomic quantum theory, infinities, instability with respect to radiation according to Maxwell's equations, violation of conservation of linear and angular momentum, lack of physical relativistic invariance, etc. From a physical perspective, the implication for the basis of the chemical bond according to quantum mechanics being the exchange integral and the requirement of zero point vibration, "strictly quantum mechanical phenomena," is that the theory cannot be a correct description of reality.

A proposed solution based on physical laws and fully compliant with Maxwell's equations solves the parameters of molecular ions and molecules of hydrogen isotopes from the Laplacian in elliptic coordinates in closed form equations with fundamental constants only. The boundary condition of nonradiation requires that the electron be a solution of the two-dimensional wave equation plus time. There is no a priori basis why the electron cannot obey this wave equation versus one based on three dimensions plus time. The corresponding Dirac delta function in the elliptic parameter $\xi$ gives the physical representation of the bound electron as a two-dimensional equipotential surface of charge (mass) density with time-harmonic motion along a geodesic at each position on the surface. The electron molecular orbitals in this case that do not depend on an exchange integral are truly physical rather than purely mathematical. The closed form solutions of $H_2^+$, $D_2^+$, $H_2$, and $D_2$ given in TABLE I show that hydrogen species can be solved in closed form with tremendous accuracy using first principles. The observed $$\sqrt{\frac{k}{\mu}}$$

dependency of vibrational energies on the isotope is obtained without the requirement of any imaginary (experimentally not observed) zero-point vibration.

The results corresponding to the nature of the chemical bond match over 20 parameters of hydrogen molecular ions and molecules. Overall, the results are better than those given by current approaches, without the fabricated exchange integral, zero-point vibration, anharmonicity term in the zero-point vibration, renormalization, effective nuclear charge, multitude of contradictory and non-unique approaches and solutions having variational and adjustable parameters and all types of violations of first principles. Such a classical solution was deemed to be impossible according to quantum mechanics since the molecule is not supposed to obey physical laws—"it was impossible to explain why two hydrogen atoms come together to form a stable chemical bond . . . the existence of the chemical bond is a quantum mechanical effect" [10]. Yet, classical laws predict the current observations and also predict new forms of hydrogen molecular ion and molecular hydrogen that was missed by QM. Remarkably, the predictions match recent experimental data [49–71, 91, 96–97].

Additionally, the ground-state density p and the ground-state wavefunction $\Psi[\rho]$ of the more recent advancement, density functional theory, have some similarities with the equipotential, minimum energy, charge-density functions (molecular orbitals) of classical quantum mechanics (CQM) [98–100]. Perhaps an opportunity exists to go beyond the nonphysical exchange integral, zero order vibration, adjustable parameters, and other "phenomena that are unique to quantum mechanics." The goal of developing curve-fitting algorithms that simply generate good numbers may be replaced by an understanding of the physical nature of the chemical bond and derivations from first principles. With such an understanding, further accurate predictions can be anticipated.

2. Background of the Invention

2.A. Classical Approach to the Nature of the Chemical Bond

2.A.a. Nonradiation Boundary Condition

In an attempt to provide some physical insight into atomic problems and starting with the same essential physics as Bohr of $e^-$ moving in the Coulombic field of the proton and the wave equation as modified by Schrödinger, a classical approach was explored which yields a model which is remarkably accurate and provides insight into physics on the atomic level [1–5, 40]. The proverbial view deeply seated in the wave-particle duality notion that there is no large-scale physical counterpart to the nature of the electron may not be correct. Physical laws and intuition may be restored when dealing with the wave equation and quantum mechanical problems. Specifically, a theory of classical quantum mechanics (CQM) was derived from first principles that successfully applies physical laws on all scales. Using Maxwell's equations, the classical wave equation is solved with the constraint that the bound n=1-state electron cannot radiate energy. It was found that quantum phenomena were predicted with accuracy within that of the fundamental constants in closed form equations that contained fundamental constants only. In this paper, the hydrogen-isotope molecular ions and molecules are solved in the same manner.

One-electron atoms include the hydrogen atom, $He^+$, $Li^{2+}$, $Be^{3+}$, and so on. The mass-energy and angular momentum of the electron are constant; this requires that the equation of motion of the electron be temporally and spatially harmonic. Thus, the classical wave equation applies and $$\left[\nabla^2 - \frac{1}{v^2}\frac{\partial^2}{\partial t^2}\right]\rho(r, \theta, \phi, t) = 0 \quad (I.1)$$

where $\rho(r,\theta,\phi,t)$ is the time dependent charge-density function of the electron in time and space. In general, the wave equation has an infinite number of solutions. To arrive at the solution which represents the electron, a suitable boundary condition must be imposed. It is well known from experiments that each single atomic electron of a given isotope radiates to the same stable state. Thus, the physical boundary condition of nonradiation of the bound electron was imposed on the solution of the wave equation for the time dependent charge-density function of the electron [1–5]. The condition for radiation by a moving point charge given by Haus [28] is that its spacetime Fourier transform does possess components that are synchronous with waves traveling at the speed of light. Conversely, it is proposed that the condition for nonradiation by an ensemble of moving point charges that comprises a current-density function is For non-radiative states, the current-density function must NOT possess spacetime Fourier components that are synchronous with waves traveling at the speed of light.

The time, radial, and angular solutions of the wave equation are separable. The motion is time harmonic with angular frequency $\omega_n$. A constant angular function is a solution to the wave equation. Solutions of the Schrödinger wave equation comprising a radial function radiate according to Maxwell's equation as shown previously by application of Haus' condition [1–5]. In fact, it was found that any function which permitted radial motion gave rise to radiation. A radial function which does satisfy the boundary condition is a radial delta function $$f(r) = \frac{1}{r^2}\delta(r - r_n) \quad (I.2)$$

This function defines a constant charge density on a spherical shell where $r_n = nr_1$ wherein n is an integer in an excited state as given in the Excited States section of Ref. [5], and Eq. (1.1) becomes the two-dimensional wave equation plus time with separable time and angular functions. As discussed in Sec. IV.1, the solution for nonradiation also gives a two-dimensional equipotential membrane for the molecular orbitals of the hydrogen molecular ion and hydrogen molecule. Consequently, the wave equation in the corresponding preferred coordinates, elliptic coordinates after James and Coolidge [10, 16], becomes two dimensional plus time. Although unconventional in this application, the two-dimensional wave equation is also familiar to quantum mechanics. For example, it is used to solve the angular functions of the Schrödinger equation [41]. The solutions are the well known spherical harmonics.

There is no a priori reason why the electron must be a solution of the three dimensional wave equation plus time and cannot obey a two-dimensional wave equation plus time. Furthermore, in addition to the important result of stability to radiation, several more very important physical results are subsequently realized: 1.) The charge is distributed on a two-dimension surface; thus, there are no infinities in the corresponding fields. Infinite fields are simply renormalized in the case of the point-particles of quantum mechanics, but it is physically gratifying that none arise in this case since infinite fields have never been measured or realized in the laboratory. 2.) The hydrogen molecular ion or molecule has finite dimensions rather than extending over all space. From measurements of the resistivity of hydrogen as a function of pressure, the finite dimensions of the hydrogen molecule are evident in the plateau of the resistivity versus pressure curve of metallic hydrogen [42]. This is in contradiction to the predictions of quantum probability functions such as an exponential radial distribution in space. 3.) Consistent with experiments, neutral scattering is predicted without violation of special relativity and causality wherein a point must be everywhere at once as required in the QM case. 4.) There is no electron self interaction. The continuous charge-density function is a two-dimensional equipotential energy surface with an electric field that is strictly normal for the elliptic parameter $\xi > 0$ (See Sec. IV) according to Gauss' law and Faraday's law. The relationship between the electric field equation and the electron source charge-density function is given by Maxwell's equation in two dimensions [43–44].

$$n \cdot (E_1 - E_2) = \frac{\sigma}{\varepsilon_0} \tag{I.3}$$

where n is the normal unit vector, $E_1=0$ ($E_1$ is the electric field inside of the MO), $E_2$ is the electric field outside of the MO and σ is the surface charge density. This relation shows that only a two-dimensional geometry meets the criterion for a fundamental particle. This is the nonsingularity geometry which is no longer divisible. It is the dimension from which it is not possible to lower dimensionality. In this case, there is no electrostatic self interaction since the corresponding potential is continuous across the surface according to Faraday's law in the electrostatic limit, and the field is discontinuous, normal to the charge according to Gauss' law [43–45]. 5.) The instability of electron-electron repulsion of molecular hydrogen is eliminated since the central field of the hydrogen molecular ion relative to a second electron at ξ>0 which binds to form the hydrogen molecule is that of a single charge at the foci. 6.) The ellipsoidal MOs allow exact spin pairing over all time which is consistent with experimental observation. This aspect is not possible in the QM model. And, 7.) The ellipsoidal MOs allow for the basis of excited states as fully Maxwellian compliant resonator mode excitations and for the ionization of the electron as a plane wave with the $\hbar$ of angular momentum conserved corresponding to the de Broglie wavelength. Physical predictions match the wave-particle duality nature of the free electron as shown in the Electron in Free Space section of Ref [5].

As with any model, the proving ground is experimental data and also the ability to predict new results. The Maxwellian solutions are unique—not an infinite number of arbitrary results from corresponding inconsistent algorithms, wavefunctions, and variational and adjustable parameters as is the case with quantum mechanics. It is found that CQM based on Maxwell's equations gives the bond energy and other parameters associated with the nature of the chemical bond in closed form equations containing fundamental constants without a plethora of fudge factors (e.g. the value used for the nuclear charge is the fundamental constant e=+1.6021892×10$^{-19}$ C). The complications of prior approaches based on the Schrödinger equation with point-particle-probability-density wavefunctions such as the required exchange integral and zero-point vibration which does not experimentally exist are eliminated. It is shown that there is remarkable agreement between predictions and the experimental observations, and the results are physically intuitive in contrast to the "phenomena that are unique to quantum mechanics" [7–8, 10]. Furthermore the theory is predictive and the predictions match recent experimental results as discussed infra. and in Secs. I.2.A.b and IV.9.

2.A.b. Excited States and the Possibility of Lower-Energy States

Consider the excited states of the hydrogen atom. The central field of the proton corresponds to integer one charge. Excited states comprise an electron with a trapped photon. In all energy states of hydrogen, the photon has an electric field which superposes with the field of the proton. In the n=1 state, the sum is one, and the sum is zero in the ionized state. In an excited state, the sum is a fraction of one (i.e. between zero and one). Derivations from first principles given in Ref. [5] demonstrate that each "allowed" fraction corresponding to an excited state is $$\frac{1}{\text{integer}}.$$

The relationship between the electric field equation and the "trapped photon" source charge-density function is given by Maxwell's equation in two dimensions. The result is given by Eq. (I.3) where n is the radial normal unit vector, $E_1=0$ ($E_1$ is the electric field outside of the electron), $E_2$ is given by the total electric field at $r_n=na_H$, and σ is the surface charge density. The electric field of an excited state is fractional; therefore, the source charge function is fractional. It is well known that fractional charge is not "allowed." The reason is that fractional charge typically corresponds to a radiative current-density function. The excited states of the hydrogen atom are examples. They are radiative; consequently, they are not stable as shown in Ref. [5]. Thus, an excited electron decays to the first nonradiative state corresponding to an integer field, n=1 (i.e. a field of integer one times the central field of the proton). Equally valid from first principles are electronic states where the magnitude of the sum of the electric field of the photon and the proton central field are an integer greater than one times the central field of the proton. These states are nonradiative. A catalyst can effect a transition between these states via a nonradiative energy transfer [5].

J. R. Rydberg showed that all of the spectral lines of atomic hydrogen were given by a completely empirical relationship:

$$\bar{\nu} = R\left(\frac{1}{n_f^2} - \frac{1}{n_i^2}\right) \tag{I.4}$$

where R=109,677 cm$^{-1}$, $n_f$=1,2,3, ..., $n_i$=2,3,4, ... and $n_i > n_f$. Bohr, Schrödinger and Heisenberg each developed a theory for atomic hydrogen that gave the energy levels in agreement with Rydberg's equation.

$$E_n = -\frac{e^2}{n^2 8\pi\varepsilon_o a_H} = -\frac{13.598 \text{ eV}}{n^2} \tag{I.5a}$$

$$n = 1, 2, 3, \ldots \tag{I.5b}$$

The excited energy states of atomic hydrogen are given by Eq. (I.5a) for n>1 in Eq. (I.5b). The n=1 state is the "ground" state for "pure" photon transitions (i.e. the n=1 state can absorb a photon and go to an excited electronic state, but it cannot release a photon and go to a lower-energy electronic state). However, an electron transition from the ground state to a lower-energy state may be possible by a resonant nonradiative energy transfer such as multipole coupling or a resonant collision mechanism. Processes such as hydrogen molecular bond formation that occur without photons and that require collisions are common [46]. Also, some commercial phosphors are based on resonant nonradiative energy transfer involving multipole coupling [47].

It is proposed that atomic hydrogen may undergo a catalytic reaction with certain atoms, excimers, and ions which provide a reaction with a net enthalpy of an integer multiple of the potential energy of atomic hydrogen, m·27.2 eV wherein m is an integer. The ionization energy of He$^+$ to He$^{2+}$ is equal to two times the potential energy of atomic hydrogen, respectively [48]. Thus, this reaction fulfills the catalyst criterion—a chemical or physical process with an enthalpy change equal to an integer multiple of 27.2 eV. The theory and supporting data were given previously [5, 49–71]. The reaction involves a nonradiative energy transfer to form a hydrogen atom that is lower in energy than unreacted atomic hydrogen that corresponds to a fractional principal quantum number. That is $$n = \frac{1}{2}, \frac{1}{3}, \frac{1}{4}, \ldots, \frac{1}{p}; \quad p \text{ is an integer} \qquad (\text{I}.5\text{c})$$

replaces the well known parameter n=integer in the Rydberg equation for hydrogen excited states. The n=1 state of hydrogen and the $$n = \frac{1}{\text{integer}}$$

states of hydrogen are nonradiative, but a transition between two nonradiative states, say n=1 to n=½, is possible via a nonradiative energy transfer. Thus, a catalyst provides a net positive enthalpy of reaction of m·27.2 eV (i.e. it resonantly accepts the nonradiative energy transfer from hydrogen atoms and releases the energy to the surroundings to affect electronic transitions to fractional quantum energy levels). As a consequence of the nonradiative energy transfer, the hydrogen atom becomes unstable and emits further energy until it achieves a lower-energy nonradiative state having a principal energy level given by Eqs. (I.5a) and (I.5c).

The predicted emission was recently reported [53]. Extreme ultraviolet (EUV) spectroscopy was recorded on microwave discharges of helium with 2% hydrogen. Novel emission lines were observed with energies of q·13.6 eV where q=1,2,3,4,6,7,8,9,11 or these discrete energies less 21.2 eV corresponding to inelastic scattering of these photons by helium atoms due to excitation of He (1s$^2$) to He (1s$^1$2p$^1$). These lines matched H(1/p), fractional Rydberg states of atomic hydrogen, formed by a resonant nonradiative energy transfer to He$^+$. Substantial experimental evidence exists that supports the existence of this novel hydrogen chemistry and its applications [49–71] such as EUV spectroscopy [49–60, 63–65, 67–68], characteristic emission from catalysts and the hydride ion products [50–51, 59–60, 65], lower-energy hydrogen emission [53–58, 67–68], chemically formed plasmas [49–62, 59–60, 63–64, 65], extraordinary (>100 eV) Balmer α line broadening [49–51, 53, 55, 59, 61–62, 65, 69], population inversion of H lines [59, 65–67], elevated electron temperature [53, 62–62, 68], anomalous plasma afterglow duration [63–64], power generation [54–55, 67–68], and analysis of novel chemical compounds [69–71].

The possibility of states with n=1/p is also predicted in the case of hydrogen molecular species wherein H(1/p) reacts a proton or two H(1/p) atoms react to form H$_2^+$(1/p) and H$_2$(1/p), respectively. The natural molecular-hydrogen coordinate system based on symmetry that was used by James and Coolidge [16], Kolos and Wolniewicz [15], and others [10] is elliptic coordinates. The magnitude of the central field in the derivations of molecular hydrogen species is taken as the general parameter p wherein p may be an integer which may be predictive of new possibilities. Thus, p replaces the effective nuclear charge of quantum mechanics and corresponds to the physical field of a resonant photon superimposed with the field of the proton. The case with p=1 is evaluated and compared with the experimental results for hydrogen species in Secs. IV.3 and IV.4, and the consequences that p=integer are considered in Sec. IV.9.

The background theory of classical quantum mechanics (CQM) for the physical solutions of hydrogen-type molecules and molecular ions is disclosed in R. Mills, *The Grand Unified Theory of Classical Quantum Mechanics*, January 2000 Edition, BlackLight Power, Inc., Cranbury, N.J., ("00 Mills GUT"), provided by BlackLight Power, Inc., 493 Old Trenton Road, Cranbury, N.J., 08512; R. Mills, *The Grand Unified Theory of Classical Quantum Mechanics*, September 2001 Edition, BlackLight Power, Inc., Cranbury, N.J., Distributed by Amazon.com ("'01 Mills GUT"), provided by BlackLight Power, Inc., 493 Old Trenton Road, Cranbury, N.J., 08512; R. Mills, *The Grand Unified Theory of Classical Quantum Mechanics*, July 2004 Edition, BlackLight Power, Inc., Cranbury, N.J., ("'04 Mills GUT"), provided by BlackLight Power, Inc., 493 Old Trenton Road, Cranbury, N.J., 08512 (posted at www.blacklightpower.com); in prior PCT applications PCT/US02/35872; PCT/US02/06945; PCT/US02/06955; PCT/US01/09055; PCT/US01/25954; PCT/US00/20820; PCT/US00/20819; PCT/US00/09055; PCT/US99/17171; PCT/US99/17129; PCT/US 98/22822; PCT/US98/14029; PCT/US96/07949; PCT/US94/02219; PCT/US91/08496; PCT/US90/01998; and PCT/US89/05037 and U.S. Pat. No. 6,024,935; the entire disclosures of which are all incorporated herein by reference; (hereinafter "Mills Prior Publications").

II. SUMMARY OF THE INVENTION

An object of the present invention is to solve the charge (mass) and current-density functions of hydrogen-type molecules and molecular ions from first principles. In an embodiment, the solution is derived from Maxwell's equations invoking the constraint that the bound electron does not radiate even though it undergoes acceleration.

Another objective of the present invention is to generate a readout, display, or image of the solutions so that the nature of the chemical bond can be better understood and potentially applied to predict reactivity and physical properties.

Another objective of the present invention is to apply the methods and systems of solving the nature of the chemical bond and its rendering to numerical or graphical form to molecules and ions other than hydrogen-types.

1. The Nature of the Chemical Bond

1.A. Dimensions of Hydrogen Molecular Ion

The hydrogen molecular ion charge and current density functions, bond distance, and energies are solved from the Laplacian in ellipsoidal coordinates with the constraint of nonradiation.

$$(\eta - \zeta) R_\xi \frac{\partial}{\partial \xi}\left(R_\xi \frac{\partial \phi}{\partial \xi}\right) + (\zeta - \xi) R_\eta \frac{\partial}{\partial \eta}\left(R_\eta \frac{\partial \phi}{\partial \eta}\right) + (\xi - \eta) R_\zeta \frac{\partial}{\partial \zeta}\left(R_\zeta \frac{\partial \phi}{\partial \zeta}\right) = 0 \qquad (\text{II}.1)$$

The force balance equation for the hydrogen molecular ion is $$\frac{\hbar^2}{m_e a^2 b^2} 2ab^2 X = \frac{e^2}{4\pi\varepsilon_o} X \qquad (II.2)$$

where $$X = \frac{1}{\sqrt{\xi + a^2}} \frac{1}{\sqrt{\xi + b^2}} \frac{1}{c} \sqrt{\frac{\xi^2 - 1}{\xi^2 - \eta^2}} \qquad (II.3)$$

Eq. (II.2) has the parametric solution $$r(t) = ia\cos\omega t + jb\sin\omega t \qquad (II.4)$$

when the semimajor axis, a, is $$a = 2a_0 \qquad (II.5)$$

The internuclear distance, $2c'$, which is the distance between the foci is $$2c' = 2a_0 \qquad (II.6)$$

The experimental internuclear distance is $\sqrt{2}a_0$. The semiminor axis is $$b = \sqrt{3}a_0 \qquad (II.7)$$

The eccentricity, e, is $$e = \frac{1}{2} \qquad (II.8)$$

1.B. The Energies of the Hydrogen Molecular Ion

The potential energy of the electron in the central field of the protons at the foci is $$V_e = \frac{-4e^2}{8\pi\varepsilon_o\sqrt{a^2 - b^2}} \ln\frac{a + \sqrt{a^2 - b^2}}{a - \sqrt{a^2 - b^2}} = -59.7575 \text{ eV} \qquad (II.9)$$

The potential energy of the two protons is $$V_p = \frac{e^2}{8\pi\varepsilon_o a_H} = 13.5984 \text{ eV} \qquad (II.10)$$

The kinetic energy of the electron is $$T = \frac{2\hbar^2}{m_e a\sqrt{a^2 - b^2}} \ln\frac{a + \sqrt{a^2 - b^2}}{a - \sqrt{a^2 - b^2}} = 29.8787 \text{ eV} \qquad (II.11)$$

During bond formation, the electron undergoes a reentrant oscillatory orbit with vibration of the protons. The corresponding energy $\overline{E}_{osc}$ is the difference between the Doppler and average vibrational kinetic energies:

$$\overline{E}_{osc} = \overline{E}_D + \overline{E}_{Kvib} = (V_e + T + V_p)\sqrt{\frac{2E_K}{Mc^2}} + \frac{1}{2}\hbar\sqrt{\frac{k}{\mu}} \qquad (II.12)$$

The total energy is $$E_T = V_e + T + V_p + \overline{E}_{osc} \qquad (II.13)$$

$$E_T = -\left\{\left[\frac{e^2}{8\pi\varepsilon_o a_H}(4\ln 3 - 1 - 2\ln 3)\right]\left[1 + \sqrt{\frac{2\hbar\sqrt{\frac{2e^2}{4pe_o(2a_H)^3}}}{m_e c^2}}\right] - \frac{1}{2}\hbar\sqrt{\frac{k}{m}}\right\} \qquad (II.14)$$

$$= -16.2803 \text{ eV} - 0.118811 \text{ eV} + \frac{1}{2}(0.29282 \text{ eV})$$

$$= -16.2527 \text{ eV}$$

The energy of a hydrogen atom is $$E(H) = -13.59844 \text{ eV} \qquad (II.15)$$

The bond dissociation energy, $E_D$, is the difference between the total energy of the hydrogen atom (Eq. (II.15)) and $E_T$ (Eq. (II.14)).

$$E_D = E(H) - E_T = 2.654 \text{ eV} \qquad (II.16)$$

2.A. Dimensions of Hydrogen

The hydrogen molecule charge and current density functions, bond distance, and energies are solved from the Laplacian in ellipsoidal coordinates with the constraint of nonradiation.

$$(\eta - \zeta)R_\xi \frac{\partial}{\partial\xi}\left(R_\xi \frac{\partial\phi}{\partial\xi}\right) + \qquad (II.17)$$

$$(\zeta - \xi)R_\eta \frac{\partial}{\partial\eta}\left(R_\eta \frac{\partial\phi}{\partial\eta}\right) + (\xi - \eta)R_\zeta \frac{\partial}{\partial\zeta}\left(R_\zeta \frac{\partial\phi}{\partial\zeta}\right) = 0$$

The force balance equation for the hydrogen molecule is $$\frac{\hbar^2}{m_e a^2 b^2} 2ab^2 X = \frac{e^2}{4\pi\varepsilon_o} X + \frac{\hbar^2}{2m_e a^2 b^2} 2ab^2 X \qquad (II.18)$$

where $$X = \frac{1}{\sqrt{\xi + a^2}} \frac{1}{\sqrt{\xi + b^2}} \frac{1}{c}\sqrt{\frac{\xi^2 - 1}{\xi^2 - \eta^2}} \qquad (II.19)$$

Eq. (II.18) has the parametric solution $$r(t) = ia\cos\omega t + jb\sin\omega t \qquad (II.20)$$

when the semimajor axis, a, is $$a = a_0 \qquad (II.21)$$

The internuclear distance, 2c', which is the distance between the foci is $$2c' = \sqrt{2}a_o \quad \text{(II.22)}$$

The experimental internuclear distance is $\sqrt{2}a_o$. The semiminor axis is $$b = \frac{1}{\sqrt{2}}a_o \quad \text{(II.23)}$$

The eccentricity, e, is $$e = \frac{1}{\sqrt{2}} \quad \text{(II.24)}$$

2.B. The Energies of the Hydrogen Molecule

The potential energy of the two electrons in the central field of the protons at the foci is $$V_e = \frac{-2e^2}{8\pi\varepsilon_o \sqrt{a^2-b^2}} \ln\frac{a+\sqrt{a^2-b^2}}{a-\sqrt{a^2-b^2}} = -67.836 \text{ eV} \quad \text{(II.25)}$$

The potential energy of the two protons is $$V_p = \frac{e^2}{8\pi\varepsilon_o \sqrt{a^2-b^2}} = 19.242 \text{ eV} \quad \text{(II.26)}$$

The kinetic energy of the electrons is $$T = \frac{\hbar^2}{2m_e a\sqrt{a^2-b^2}} \ln\frac{a+\sqrt{a^2-b^2}}{a-\sqrt{a^2-b^2}} = 33.918 \text{ eV} \quad \text{(II.27)}$$

The energy, $V_m$, of the magnetic force between the electrons is $$V_m = \frac{-\hbar^2}{4m_e a\sqrt{a^2-b^2}} \ln\frac{a+\sqrt{a^2-b^2}}{a-\sqrt{a^2-b^2}} = -16.959 \text{ eV} \quad \text{(II.28)}$$

During bond formation, the electrons undergo a reentrant oscillatory orbit with vibration of the protons. The corresponding energy $\overline{E}_{osc}$ is the difference between the Doppler and average vibrational kinetic energies:

$$\overline{E}_{osc} = \overline{E}_D + \overline{E}_{Kvib} = (V_e + T + V_m + V_p)\sqrt{\frac{2\overline{E}_K}{Mc^2}} + \frac{1}{2}\hbar\sqrt{\frac{k}{\mu}} \quad \text{(II.29)}$$

The total energy is $$E_T = V_e + T + V_m + V_p + \overline{E}_{osc} \quad \text{(II.30)}$$

$$E_T = -\frac{e^2}{8\pi\varepsilon_o a_0}\left[\left(2\sqrt{2} - \sqrt{2} + \frac{\sqrt{2}}{2}\right)\ln\frac{\sqrt{2}+1}{\sqrt{2}-1} - \sqrt{2}\right] \quad \text{(II.31)}$$

$$\left[1 + \sqrt{\frac{2\hbar\sqrt{\frac{e^2}{4\pi\varepsilon_o a_0^3}}}{m_e c^2}}\right] - \frac{1}{2}\hbar\sqrt{\frac{k}{\mu}}$$

$$= -31.689 \text{ eV}$$

The energy of two hydrogen atoms is $$E(2H[a_H]) = -27.21 \text{ eV} \quad \text{(II.32)}$$

The bond dissociation energy, $E_D$, is the difference between the total energy of the corresponding hydrogen atoms (Eq. (II.32)) and $E_T$ (Eq. (II.31)).

$$E_D = E(2H[a_H]) - E_T = 4.478 \text{ eV} \quad \text{(II.33)}$$

The experimental energy is $E_D$=4.478 eV. The calculated and experimental parameters of $H_2$, $D_2$, $H_2^+$, and $D_2^+$; from Sec. IV and Chp. 12 of Ref. [3] are given in TABLE I.

3. Hydrinos

A hydrogen atom having a binding energy given by $$\text{Binding Energy} = \frac{13.6 \text{ eV}}{\left(\frac{1}{p}\right)^2} \quad \text{(II.34)}$$

where p is an integer greater than 1, preferably from 2 to 200, is disclosed in R. Mills, *The Grand Unified Theory of Classical Quantum Mechanics*, January 2000 Edition, BlackLight Power, Inc., Cranbury, N.J., Distributed by Amazon.com ("'00 Mills GUT"), provided by BlackLight Power, Inc., 493 Old Trenton Road, Cranbury, N.J., 08512; R. Mills, *The Grand Unified Theory of Classical Quantum Mechanics*, September 2001 Edition, BlackLight Power, Inc., Cranbury, N.J., Distributed by Amazon.com ("'01 Mills GUT"), provided by BlackLight Power, Inc., 493 Old Trenton Road, Cranbury, N.J., 08512 R. Mills, *The Grand Unified Theory of Classical Quantum Mechanics*, July, 2004 Edition posted at www.blacklightpower.com ("'04 Mills GUT").

With regard to the Hydrino Theory—BlackLight Process section of '04 Mills GUT, the possibility of states with n=1/p is also predicted in the case of hydrogen molecular species wherein H(1/p) reacts a proton or two H(1/p) atoms react to form $H_2^+(1/p)$ and $H_2(1/p)$, respectively. The natural molecular-hydrogen coordinate system based on symmetry is elliptic coordinates. The magnitude of the central field in the derivations of molecular hydrogen species is taken as the general parameter p wherein p may be an integer which may be predictive of new possibilities. Thus, p replaces the effective nuclear charge of quantum mechanics and corresponds to the physical field of a resonant photon superimposed with the field of the proton. The case with p=1 is evaluated and compared with the experimental results for hydrogen species in TABLE I, and the consequences that p=integer are considered in the Nuclear Magnetic Resonance Shift section.

Two hydrogen atoms react to form a diatomic molecule, the hydrogen molecule.

$$2H[a_H] \to H_2[2c'=\sqrt{2}a_o] \tag{II.35}$$

where $2c'$ is the internuclear distance. Also, two hydrino atoms react to form a diatomic molecule, a dihydrino molecule.

$$2H\left[\frac{a_H}{p}\right] \to H_2\left[2c' = \frac{\sqrt{2}\,a_o}{p}\right] \tag{II.36}$$

where p is an integer.

Hydrogen molecules form hydrogen molecular ions when they are singly ionized.

$$H_2[2c'=\sqrt{2}a_o] \to H_2[2c'=2a_o]^+ + e- \tag{II.37}$$

Also, dihydrino molecules form dihydrino molecular ions when they are singly ionized.

$$H_2\left[2c' = \frac{\sqrt{2}\,a_o}{p}\right] \to H_2\left[2c' = \frac{2a_o}{p}\right]^+ + e- \tag{II.38}$$

3.A. Dimensions of Hydrogen Molecular Ion $H_2^+(1/p)$

To obtain the parameters of $H_2^+(1/p)$, the Laplacian in ellipsoidal coordinates (Eq. (II.1)) is solved with the constraint of nonradiation. The force balance equation for the hydrogen molecular ion $H_2^+(1/p)$ having a central field of +pe at each focus of the prolate spheroid molecular orbital is $$\frac{\hbar^2}{m_e a^2 b^2} 2ab^2 X = \frac{pe^2}{4\pi\varepsilon_o} X \tag{II.39}$$

where $$X = \frac{1}{\sqrt{\xi+a^2}} \frac{1}{\sqrt{\xi+b^2}} \frac{1}{c}\sqrt{\frac{\xi^2-1}{\xi^2-\eta^2}} \tag{II.40}$$

Eq. (II.39) has the parametric solution $$r(t) = ia \cos \omega t + jb \sin \omega t \tag{II.41}$$

when the semimajor axis, a, is $$a = \frac{2a_o}{p} \tag{II.42}$$

The internuclear distance, $2c'$, which is the distance between the foci is $$2c' = \frac{2a_o}{p} \tag{II.43}$$

The semiminor axis is $$b = \frac{\sqrt{3}}{p} a_o \tag{II.44}$$

The eccentricity, e, is $$e = \frac{1}{2} \tag{II.45}$$

3.B. The Energies of the Hydrogen Molecular Ion $H_2^+(1/p)$

The potential energy of the electron in the central field of +pe at the foci is $$V_e = \frac{-4p^2 e^2}{8\pi\varepsilon_o a_o} \ln 3 \tag{II.46}$$

The potential energy of the two protons is $$V_p = \frac{p^2 e^2}{8\pi\varepsilon_o a_o} \tag{II.47}$$

The kinetic energy of the electron is $$T = \frac{2p^2 e^2}{8\pi\varepsilon_o a_o} \ln 3 \tag{II.48}$$

During bond formation, the electron undergoes a reentrant oscillatory orbit with vibration of the protons. The corresponding energy $\overline{E}_{osc}$ is the difference between the Doppler and average vibrational kinetic energies:

$$\overline{E}_{osc} = \overline{E}_D + \overline{E}_{Kvib} = (V_e + T + V_p)\sqrt{\frac{2\overline{E}_K}{Mc^2}} + \frac{1}{2}\hbar p^2 \sqrt{\frac{k}{\mu}} \tag{II.49}$$

$$= -p^3 0.118755 \text{ eV} + \frac{1}{2}p^2(0.29282 \text{ eV})$$

The total energy of the hydrogen molecular ion having a central field of +pe at each focus of the prolate spheroid molecular orbital is $$E_T = V_e + T + V_p + \overline{E}_{osc} \tag{II.50}$$

$$E_T = -p^2 \left\{ \left[ \frac{e^2}{8\pi\varepsilon_o a_H}(4\ln 3 - 1 - 2\ln 3) \right] \left[ 1 + p\sqrt{\frac{2\hbar\sqrt{\frac{2e^2}{4\pi\varepsilon_o(2a_H)^3 m_e}}}{m_e c^2}} \right] - \frac{1}{2}\hbar\sqrt{\frac{k}{\mu}} \right\} \tag{II.51}$$

$$= -p^2 16.13392 \text{ eV} - p^3 0.118755 \text{ eV}$$

The energy of a hydrogen atom H(1/p) is $$E(H(1/p)) = -p^2 13.59844 \text{ eV} \tag{II.52}$$

The bond dissociation energy, $E_D$, is the difference between the total energy of the hydrogen atom H(1/p) (Eq. (II.52)) and $E_T$ (Eq. (II.51)).

$$\begin{aligned} E_D &= -p^2 13.59844 - E_T \\ &= -p^2 13.59844 - (-p^2 16.13392 \text{ eV} - p^3 0.118755 \text{ eV}) \\ &= p^2 2.535 \text{ eV} + p^3 0.118755 \text{ eV} \end{aligned} \tag{II.53}$$

4.A. Dimensions of Hydrogen $H_2$ (1/p)

To obtain the parameters of $H_2(1/p)$, the Laplacian in ellipsoidal coordinates (Eq. (II.1)) is solved with the constraint of nonradiation. The force balance equation for the hydrogen molecule $H_2(1/p)$ having a central field of +pe at each focus of the prolate spheroid molecular orbital is $$\frac{\hbar^2}{m_e a^2 b^2} 2ab^2 X = \frac{pe^2}{4\pi\varepsilon_o} X + \frac{\hbar^2}{2m_e a^2 b^2} 2ab^2 X \tag{II.54}$$

where $$X = \frac{1}{\sqrt{\xi + a^2}} \frac{1}{\sqrt{\xi + b^2}} \frac{1}{c} \sqrt{\frac{\xi^2 - 1}{\xi - \eta^2}} \tag{II.55}$$

Eq. (II.54) has the parametric solution $$r(t) = ia \cos \omega t + jb \sin \omega t \tag{II.56}$$

when the semimajor axis, a, is $$a = \frac{a_o}{p} \tag{II.57}$$

The internuclear distance, 2c', which is the distance between the foci is $$2c' = \frac{\sqrt{2}}{p} a_o \tag{II.58}$$

The semiminor axis is $$b = c' = \frac{1}{p\sqrt{2}} a_o \tag{II.59}$$

The eccentricity, e, is $$e = \frac{1}{\sqrt{2}} \tag{II.60}$$

4.B. The Energies of the Hydrogen Molecule $H_2$(1/p)

The potential energy of the two electrons in the central field of +pe at the foci is $$V_e = \frac{-2pe^2}{8\pi\varepsilon_o \sqrt{a^2 - b^2}} \ln \frac{a + \sqrt{a^2 - b^2}}{a - \sqrt{a^2 - b^2}} \tag{II.61}$$

The potential energy of the two protons is $$V_p = \frac{p}{8\pi\varepsilon_o} \frac{e^2}{\sqrt{a^2 - b^2}} \tag{II.62}$$

The kinetic energy of the electrons is $$T = \frac{\hbar^2}{2m_e a \sqrt{a^2 - b^2}} \ln \frac{a + \sqrt{a^2 - b^2}}{a - \sqrt{a^2 - b^2}} \tag{II.63}$$

The energy, $V_m$, of the magnetic force between the electrons is $$V_m = \frac{-\hbar^2}{4m_e a \sqrt{a^2 - b^2}} \ln \frac{a + \sqrt{a^2 - b^2}}{a - \sqrt{a^2 - b^2}} \tag{II.64}$$

During bond formation, the electrons undergo a reentrant oscillatory orbit with vibration of the protons. The corresponding energy $\overline{E}_{osc}$ is the difference between the Doppler and average vibrational kinetic energies:

$$\begin{aligned} \overline{E}_{osc} &= \overline{E}_D + \overline{E}_{Kvib} \\ &= (V_e + T + V_m + V_p)\sqrt{\frac{2\overline{E}_K}{Mc^2}} + \frac{1}{2}\hbar p^2 \sqrt{\frac{k}{\mu}} \\ &= -p^3 0.326469 \text{ eV} + \frac{1}{2} p^2 (0.56764 \text{ eV}) \end{aligned} \tag{II.65}$$

The total energy of the hydrogen molecule having a central field of +pe at each focus of the prolate spheroid molecular orbital is $$E_T = V_e + T + V_m + V_p + \overline{E}_{osc} \tag{II.66}$$

$$E_T = -p^2 \left\{ \frac{e^2}{8\pi\varepsilon_o a_0} \left[ \left(2\sqrt{2} - \sqrt{2} + \frac{\sqrt{2}}{2}\right) \ln \frac{\sqrt{2}+1}{\sqrt{2}-1} \right. \right. \\ \left. \left. -\sqrt{2} \right] \left[ 1 + p \sqrt{\frac{2\hbar \sqrt{\frac{e^2}{4\pi\varepsilon_o a_0^3}}}{m_e c^2}} \right] - \frac{1}{2}\hbar\sqrt{\frac{k}{\mu}} \right\} \tag{II.67}$$

$$= -p^2 31.351 \text{ eV} - p^3 0.326469 \text{ eV}$$

The energy of two hydrogen atoms H(1/p) is $$E(2H(1/p)) = -p^2 27.20 \text{ eV} \tag{II.68}$$

The bond dissociation energy, $E_D$, is the difference between the total energy of the corresponding hydrogen atoms (Eq. (II.68)) and $E_T$ (Eq. (II.67)).

$$\begin{aligned}E_D &= E(2H(1/p)) - E_T \tag{II.69}\\ &= -p^2 27.20 \text{ eV} - E_T \\ &= -p^2 27.20 \text{ eV} - (-p^2 31.351 \text{ eV} - p^3 0.326469 \text{ eV}) \\ &= p^2 4.151 \text{ eV} + p^3 0.326469 \text{ eV}\end{aligned}$$

In an embodiment, the physical, Maxwellian solutions for the dimensions and energies of hydrogen-type molecules and molecular ions are processed with a processing means to produce an output. Embodiments of the system for performing computing and rendering of the nature of the chemical bond using the physical solutions may comprise a general purpose computer. Such a general purpose computer may have any number of basic configurations. For example, such a general purpose computer may comprise a central processing unit (CPU), one or more specialized processors, system memory, a mass storage device such as a magnetic disk, an optical disk, or other storage device, an input means such as a keyboard or mouse, a display device, and a printer or other output device. A system implementing the present invention can also comprise a special purpose computer or other hardware system and all should be included within its scope.

III. BRIEF DESCRIPTION OF THE DRAWINGS

Figure 1B:
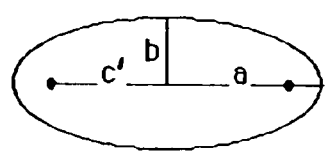
Figure 1C:
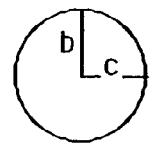

FIG. 1A is a prolate spheroid molecular orbital in accordance with the present invention, and FIGS. 1B and 1C are cross sections of the prolate spheroid molecular orbital showing the parameters of molecules and molecular ions in accordance with the present invention where, a is the semimajor axis, 2a is the total length of the molecule or molecular ion along the principal axis, b=c is the semiminor axis 2 b=2 c is the total width of the molecule or molecular ion along the minor axis, c' is the distance from the origin to a focus (nucleus), and 2c' is the internuclear distance.

IV. DETAILED DESCRIPTION OF THE INVENTION

The following preferred embodiments of the invention disclose numerous calculations which are merely intended as illustrative examples. Based on the detailed written description, one skilled in the art would easily be able to practice this invention within other like calculations to produce the desired result without undue effort.

1. Hydrogen-Type Molecular Ions

Each hydrogen-type molecular ion comprises two protons and an electron where the equation of motion of the electron is determined by the central field which is p times that of a proton at each focus (p is one for the hydrogen molecular ion, and p is an integer greater than one for each $H_2^+(1/p)$, called dihydrino molecular ion). The differential equations of motion in the case of a central field are [72]

$$m(\ddot{r} - r\dot{\theta}^2) = f(r) \tag{15}$$

$$m(2\dot{r}\dot{\theta} + r\ddot{\theta}) = 0 \tag{16}$$

The second or transverse equation, Eq. (16), gives the result that the angular momentum is constant.

$$r^2\dot{\theta} = \text{constant} = L/m \tag{17}$$

where L is the angular momentum ($\hbar$ in the case of the electron). The central force equations can be transformed into an orbital equation by the substitution, $$u = \frac{1}{r}.$$

The differential equation of the orbit of a particle moving under a central force is $$\frac{\delta^2 u}{\delta \theta^2} + u = \frac{-1}{\frac{mL^2 u^2}{m^2}} f(u^{-1}) \tag{18}$$

Because the angular momentum is constant, motion in only one plane need be considered; thus, the orbital equation is given in polar coordinates. The solution of Eq. (18) for an inverse-squared force is $$f(r) = -\frac{k}{r^2} \tag{19}$$

$$r = r_0 \frac{1+e}{1+e\cos\theta} \tag{20}$$

$$e = A \frac{m\frac{L^2}{m^2}}{k} \tag{21}$$

$$r_0 = \frac{m\frac{L^2}{m^2}}{k(1+e)} \tag{22}$$

where e is the eccentricity of the ellipse and A is a constant. The equation of motion due to a central force can also be expressed in terms of the energies of the orbit. The square of the speed in polar coordinates is $$v^2 = (\dot{r}^2 + r^2\dot{\theta}^2) \tag{23}$$

Since a central force is conservative, the total energy, E, is equal to the sum of the kinetic, T, and the potential, V, and is constant. The total energy is $$\frac{1}{2}m(\dot{r}^2 + r^2\dot{\theta}^2) + V(r) = E = \text{constant} \tag{24}$$

Substitution of the variable $$u = \frac{1}{r}$$

and Eq. (17) into Eq. (24) gives the orbital energy equation.

$$\frac{1}{2}m\frac{L^2}{m^2}\left(\left(\frac{\delta^2 u}{\delta \theta^2}\right) + u^2\right) + V(u^{-1}) = E \tag{25}$$

Because the potential energy function, V(r), for an inverse-squared force field is $$V(r) = -\frac{k}{r} = -ku \quad (26)$$

the energy equation of the orbit, Eq. (25), $$\frac{1}{2}m\frac{L^2}{m^2}\left(\left(\frac{\delta^2 u}{\delta\theta^2}\right) + u^2\right) - ku = E \quad (27)$$

which has the solution $$r = \frac{m\frac{L^2}{m^2}k^{-1}}{1 + \left(1 + 2Em\frac{L^2}{m^2}k^{-2}\right)^{1/2}\cos\theta} \quad (28)$$

where the eccentricity, e, is $$e = \left(1 + 2Em\frac{L^2}{m^2}k^{-2}\right)^{1/2} \quad (29)$$

Eq. (29) permits the classification of the orbits according to the total energy, E, as follows:
  E<0, e<1 closed orbits (ellipse or circle)
  E=0, e=1 parabolic orbit
  E>0, e>1 hyperbolic orbit Since E=T+V and is constant, the closed orbits are those for which T<|V|, and the open orbits are those for which T≧|V|. It can be shown that the time average of the kinetic energy, <T>, for elliptic motion in an inverse-squared field is ½ that of the time average of the potential energy, <V>. <T>=½<V>.

As demonstrated in the One Electron Atom section of Ref. [5], the electric inverse-squared force is conservative; thus, the angular momentum of the electron, $\hbar$, and the energy of atomic orbitals called "orbitspheres" are constant. In addition, the orbitspheres are nonradiative when the boundary condition is met.

The central force equation, Eq. (24), has orbital solutions which are circular, elliptic, parabolic, or hyperbolic. The former two types of solutions are associated with atomic and molecular orbitals. These solutions are nonradiative. The boundary condition for nonradiation given in the One Electron Atom section of Ref. [5], is the absence of components of the space-time Fourier transform of the charge-density function synchronous with waves traveling at the speed of light. The boundary condition is met when the velocity for the charge density at every coordinate position on the orbitsphere is $$v_n = \frac{\hbar}{m_e r_n} \quad (30)$$

The allowed velocities and angular frequencies are related to $r_n$ by $$v_n = r_n \omega_n \quad (31)$$

$$\omega_n = \frac{\hbar}{m_e r_n^2} \quad (32)$$

As demonstrated in the One Electron Atom section of Ref. [5] and by Eq. (32), this condition is met for the product function of a radial Dirac delta function and a time harmonic function where the angular frequency, ω, is constant and given by Eq. (32).

$$\omega_n = \frac{\hbar}{m_e r_n^2} = \frac{\frac{\pi L}{m_e}}{A} \quad (33)$$

where L is the angular momentum and A is the area of the closed geodesic orbit. Consider the solution of the central force equation comprising the product of a two-dimensional ellipsoid and a time harmonic function. The spatial part of the product function is the convolution of a radial Dirac delta function with the equation of an ellipsoid. The Fourier transform of the convolution of two functions is the product of the individual Fourier transforms of the functions; thus, the boundary condition is met for an ellipsoidal-time harmonic function when $$\omega_n = \frac{\pi\hbar}{m_e A} = \frac{\hbar}{m_e ab} \quad (34)$$

where the area of an ellipse is $$A = \pi ab \quad (35)$$

where 2b is the length of the semiminor axis and 2a is the length of the semimajor axis[1]. The geometry of molecular hydrogen is elliptic with the internuclear axis as the principal axis; thus, the electron orbital is a two-dimensional ellipsoidal-time harmonic function. The mass follows geodesics time harmonically as determined by the central field of the protons at the foci. Rotational symmetry about the internuclear axis further determines that the orbital is a prolate spheroid. In general, ellipsoidal orbits of molecular bonding, hereafter referred to as ellipsoidal molecular orbitals (MOs), have the general equation $$\frac{x^2}{a^2} + \frac{y^2}{b^2} + \frac{z^2}{c^2} = 1 \quad (36)$$

The semiprincipal axes of the ellipsoid are a, b, c.

[1] In addition to nonradiation, the angular frequency given by Eq. (34) corresponds to a Lorentzian invariant magnetic moment of a Bohr magneton, $\mu_B$, as given in Sec. VIII. The internal field is uniform along the semiminor axis, and the far field is that of a dipole as shown in Sec. VIII.

In ellipsoidal coordinates, the Laplacian is $$(\eta - \zeta)R_\xi \frac{\partial}{\partial \xi}\left(R_\xi \frac{\partial \phi}{\partial \xi}\right) + \\ (\zeta - \xi)R_\eta \frac{\partial}{\partial \eta}\left(R_\eta \frac{\partial \phi}{\partial \eta}\right) + (\xi - \eta)R_\zeta \frac{\partial}{\partial \zeta}\left(R_\zeta \frac{\partial \phi}{\partial \zeta}\right) = 0 \quad (37)$$

An ellipsoidal MO is equivalent to a charged perfect conductor (i.e. no dissipation to current flow) whose surface is given by Eq. (36). It is a two-dimensional equipotential membrane where each MO is supported by the outward centrifugal force due to the corresponding angular velocity which conserves its angular momentum of $\hbar$. It satisfies the boundary conditions for a discontinuity of charge in Maxwell's equations, Eq. (12). It carries a total charge q, and it's potential is a solution of the Laplacian in ellipsoidal coordinates, Eq. (37).

Excited states of orbitspheres are discussed in the Excited States of the One Electron Atom (Quantization) section of Ref. [5]. In the case of ellipsoidal MOs, excited electronic states are created when photons of discrete frequencies are trapped in the ellipsoidal resonator cavity of the MO The photon changes the effective charge at the MO surface where the central field is ellipsoidal and arises from the protons and the effective charge of the "trapped photon" at the foci of the MO Force balance is achieved at a series of ellipsoidal equipotential two-dimensional surfaces confocal with the ground state ellipsoid. The "trapped photons" are solutions of the Laplacian in ellipsoidal coordinates, Eq. (37).

As is the case with the orbitsphere, higher and lower energy states are equally valid. The photon standing wave in both cases is a solution of the Laplacian in ellipsoidal coordinates. For an ellipsoidal resonator cavity, the relationship between an allowed circumference, 4aE, and the photon standing wavelength, $\lambda$, is $$4aE = n\lambda \quad (38)$$

where n is an integer and where $$k = \frac{\sqrt{a^2 - b^2}}{a} \quad (39)$$

is used in the elliptic integral, E, of Eq. (38). Applying Eqs. (38) and (39), the relationship between an allowed angular frequency given by Eq. (34) and the photon standing wave angular frequency, $\omega$, is:

$$\frac{\pi \hbar}{m_e A} = \frac{\hbar}{m_e n a_1 n b_1} = \frac{\hbar}{m_e a_n b_n} = \frac{1}{n^2}\omega_1 = \omega_n \quad (40)$$

where n=1, 2, 3, 4, . . .

$$n = \frac{1}{2}, \frac{1}{3}, \frac{1}{4}, \ldots$$

$\omega_1$ is the allowed angular frequency for n=1
$a_1$ and $b_1$ are the allowed semimajor and semiminor axes for n=1

The potential, $\phi$, and distribution of charge, $\sigma$, over the conducting surface of an ellipsoidal MO are sought given the conditions: 1.) the potential is equivalent to that of a charged ellipsoidal conductor whose surface is given by Eq. (36), 2.) it carries a total charge q, and 3.) initially there is no external applied field. To solve this problem, a potential function must be found which satisfies Eq. (37), which is regular at infinity, and which is constant over the given ellipsoid. The solution is well known and is given after Stratton [73]. Consider that the Laplacian is solved in ellipsoidal coordinates wherein $\xi$ is the parameter of a family of ellipsoids all confocal with the standard surface 4=0 whose axes have the specified values a, b, c. The variables $\zeta$ and $\eta$ are the parameters of confocal hyperboloids and as such serve to measure position on any ellipsoid $\xi$=constant. On the surface $\xi$=0; therefore, $\phi$ must be independent of $\zeta$ and $\eta$. Due to the uniqueness property of solutions of the Laplacian, a function which satisfies Eq. (37), behaves properly at infinity, and depends only on $\xi$, can be adjusted to represent the potential correctly at any point outside the ellipsoid $\xi$=0.

Thus, it is assumed that $\phi=\phi(\xi)$. Then, the Laplacian reduces to $$\frac{\delta}{\delta \xi}\left(R_\xi \frac{\partial \phi}{\partial \xi}\right) = 0 \quad R_\xi = \sqrt{(\xi + a^2)(\xi + b^2)(\xi + c^2)} \quad (41)$$

which on integration leads to $$\phi(\xi) = C_1 \int_\xi^\infty \frac{\delta \xi}{R_\xi} \quad (42)$$

where $C_1$ is an arbitrary constant. The upper limit is selected to ensure the proper behavior at infinity. When $\xi$ becomes very large, $R_\xi$ approaches $\xi^{3/2}$ and $$\phi \sim \frac{2C_1}{\sqrt{\xi}} \quad (\xi \to \infty) \quad (43)$$

Furthermore, the equation of an ellipsoid can be written in the form $$\frac{x^2}{1 + \frac{a^2}{\xi}} + \frac{y^2}{1 + \frac{b^2}{\xi}} + \frac{z^2}{1 + \frac{c^2}{\xi}} = \xi \quad (44)$$

If $r^2 = x^2 + y^2 + Z^2$ is the distance from the origin to any point on the ellipsoid $\xi$, it is apparent that as $\xi$ becomes very large $\xi \to r^2$. Thus, at great distances from the origin, the potential becomes that of a point charge at the origin:

$$\phi \sim \frac{2C_1}{r} \quad (45)$$

The solution Eq. (32) is, therefore, regular at infinity, and the constant $C_1$ is then determined. It has been shown by Stratton [73] that whatever the distribution, the dominant term of the expansion at remote points is the potential of a point charge at the origin equal to the total charge of the distribution—in this case q. Hence $$C_1 = \frac{q}{8\pi\varepsilon_o},$$

and the potential at any point is $$\phi(\xi) = \frac{q}{8\pi\varepsilon_o} \int_\xi^\infty \frac{\partial \xi}{R_\xi} \quad (46)$$

The equipotential surfaces are the ellipsoids $\xi$=constant. Eq. (46) is an elliptic integral and its values have been tabulated [74].

Since the distance along a curvilinear coordinate $u^1$ is measured not by $du^1$ but by $h_1 du^1$, the normal derivative in ellipsoidal coordinates is given by $$\frac{\delta\phi}{\delta n} = \frac{1}{h_1}\frac{\delta\phi}{\delta\xi} = \frac{-q}{4\pi\varepsilon_o}\frac{1}{\sqrt{(\xi-\eta)(\xi-\zeta)}} \quad (47)$$

where $$h_1 = \frac{1}{2}\frac{\sqrt{(\xi-\eta)(\xi-\zeta)}}{R_\xi} \quad (48)$$

The density of charge, $\sigma$, over the surface $\xi=0$ is $$\sigma = \varepsilon_o\left(\frac{\delta\phi}{\delta n}\right)_{\xi=0} = \frac{q}{4\pi\sqrt{\eta\zeta}} \quad (49)$$

Defining x, y, z in terms of $\xi$, $\eta$, $\zeta$ we put $\xi=0$, it may be easily verified that $$\frac{x^2}{a^4} + \frac{y^2}{b^4} + \frac{z^2}{c^4} = \frac{\zeta\eta}{a^2b^2c^2} \quad (\xi=0) \quad (50)$$

Consequently, the charge density in rectangular coordinates is $$\sigma = \frac{q}{4\pi abc}\frac{1}{\sqrt{\frac{x^2}{a^4}+\frac{y^2}{b^4}+\frac{z^2}{c^4}}} \quad (51)$$

(The mass-density function of an MO is equivalent to its charge-density function where m replaces q of Eq. (51)). The equation of the plane tangent to the ellipsoid at the point $x_0$, $y_0$, $z_0$ is $$X\frac{x_0}{a^2} + Y\frac{y_0}{b^2} + Z\frac{z_0}{c^2} = 1 \quad (52)$$

where X, Y, Z are running coordinates in the plane. After dividing through by the square root of the sum of the squares of the coefficients of X, Y, and Z, the right member is the distance D from the origin to the tangent plane. That is, $$D = \frac{1}{\sqrt{\frac{x^2}{a^4}+\frac{y^2}{b^4}+\frac{z^2}{c^4}}} \quad (53)$$

so that $$\sigma = \frac{q}{4\pi abc}D \quad (54)$$

In other words, the surface density at any point on a charged ellipsoidal conductor is proportional to the perpendicular distance from the center of the ellipsoid to the plane tangent to the ellipsoid at the point. The charge is thus greater on the more sharply rounded ends farther away from the origin.

In the case of hydrogen-type molecules and molecular ions, rotational symmetry about the internuclear axis requires that two of the axes be equal. Thus, the MO is a spheroid, and Eq. (46) can be integrated in terms of elementary functions. If a>b=c, the spheroid is prolate, and the potential is given by $$\phi = \frac{1}{8\pi\varepsilon_o}\frac{q}{\sqrt{a^2-b^2}}\ln\frac{\sqrt{\xi+a^2}+\sqrt{a^2-b^2}}{\sqrt{\xi+a^2}-\sqrt{a^2-b^2}} \quad (55)$$

A prolate spheroid MO and the definition of axes are shown in FIGS. 1A and 1B, respectively.

1.A. Spheroidal Force Equations

1.A.a. Electric Force

The spheroidal MO is a two-dimensional surface of constant potential given by Eq. (55) for $\xi=0$. For an isolated electron MO the electric field inside is zero as given by Gauss' Law $$\int_S E dA = \int_V \frac{\rho}{\varepsilon_o} dV \quad (56)$$

where the charge density, $\rho$, inside the MO is zero. Gauss' Law at a two-dimensional surface with continuity of the potential across the surface according to Faraday's law in the electrostatic limit [43–45] is $$n \cdot (E_1 - E_2) = \frac{\sigma}{\varepsilon_0} \quad (57)$$

$E_2$ is the electric field inside which is zero. The electric field of an ellipsoidal MO is given by substituting σ given by Eq. (47) and Eq. (49) into Eq. (57).

$$E = \frac{\sigma}{\varepsilon_o} = \frac{q}{4\pi\varepsilon_o} \frac{1}{\sqrt{(\xi-\eta)(\xi-\zeta)}} \quad (58)$$

The electric field in spheroid coordinates is $$E = \frac{q}{8\pi\varepsilon_o} \frac{1}{\sqrt{\xi+a^2}} \frac{1}{\sqrt{\xi+b^2}} \frac{1}{c}\sqrt{\frac{\xi^2-1}{\xi^2-\eta^2}} \quad (59)$$

From Eq. (40), the magnitude of the elliptic field corresponding to a below "ground state" hydrogen-type molecular ion is an integer. The integer is one in the case of the hydrogen molecular ion and an integer greater than one in the case of each dihydrino molecular ion. The central electric force from the two protons, $F_e$, is $$F_e = ZeE = \frac{p2e^2}{8\pi\varepsilon_o} \frac{1}{\sqrt{\xi+a^2}} \frac{1}{\sqrt{\xi+b^2}} \frac{1}{c}\sqrt{\frac{\xi^2-1}{\xi^2-\eta^2}} \quad (60)$$

where p is one for the hydrogen molecular ion, and p is an integer greater than one for each dihydrino molecule and molecular ion.

1.A.b. Centrifugal Force

Each point or coordinate position on the continuous two-dimensional electron MO defines an infinitesimal mass-density element which moves along a geodesic orbit of a spheroidal MO in such a way that its eccentric angle, θ, changes at a constant rate. That is θ=ωt at time t where ω is a constant, and $$r(t) = ia \cos\omega t + jb \sin\omega t \quad (61)$$

is the parametric equation of the ellipse of the geodesic. If a(t) denotes the acceleration vector, then $$a(t) = -\omega^2 r(t) \quad (62)$$

In other words, the acceleration is centripetal as in the case of circular motion with constant angular speed, ω. The centripetal force, $F_c$, is $$F_c = ma = -m\omega^2 r(t) \quad (63)$$

Recall that nonradiation results when ω=constant given by Eq. (40). Substitution of ω given by Eq. (40) into Eq. (63) gives $$F_c = \frac{-\hbar^2}{m_e a^2 b^2} r(t) = \frac{-\hbar^2}{m_e a^2 b^2} D \quad (64)$$

where D is the distance from the origin to the tangent plane as given by Eq. (53). If X is defined as follows $$X = \frac{1}{\sqrt{\xi+a^2}} \frac{1}{\sqrt{\xi+b^2}} \frac{1}{c}\sqrt{\frac{\xi^2-1}{\xi^2-\eta^2}} \quad (65)$$

then it follows from Eqs. (47), (54), (58), and (60) that $$D = 2ab^2 X \quad (66)$$

1.B. Force Balance of Hydrogen-Type Molecular Ions

Force balance between the electric and centrifugal forces is $$\frac{\hbar^2}{m_e a^2 b^2} 2ab^2 X = \frac{pe^2}{4\pi\varepsilon_o} X \quad (67)$$

which has the parametric solution given by Eq. (61) when $$a = \frac{2a_0}{p} \quad (68)$$

1.C. Energies of Hydrogen-type Molecular Ions

From Eq. (40), the magnitude of the elliptic field corresponding to a below "ground state" hydrogen-type molecule is an integer, p. The potential energy, $V_e$, of the electron MO in the field of magnitude p times that of the protons at the foci (ξ=0) is $$V_e = \frac{-4pe^2}{8\pi\varepsilon_o\sqrt{a^2-b^2}} \ln\frac{a+\sqrt{a^2-b^2}}{a-\sqrt{a^2-b^2}} \quad (69)$$

where $$\sqrt{a^2-b^2} = c' \quad (70)$$

2c' is the distance between the foci which is the internuclear distance. The kinetic energy, T, of the electron MO is given by the integral of the left side of Eq. (67)

$$T = \frac{2\hbar^2}{m_e a\sqrt{a^2-b^2}} \ln\frac{a+\sqrt{a^2-b^2}}{a-\sqrt{a^2-b^2}} \quad (71)$$

From the orbital equations in polar coordinates, Eqs. (20–22), the following relationship can be derived:

$$a = \frac{m\frac{L^2}{m^2}}{k(1-e^2)} \quad (72)$$

For any ellipse, $$b = a\sqrt{1-e^2} \quad (73)$$

Thus, $$b = a\sqrt{\frac{\frac{L^2}{m^2}m}{ka}} \text{ (polar coordinates)} \quad (74)$$

Using Eqs. (64) and (71), and (26) and (71), respectively, it can be appreciated that b of polar coordinates corresponds to $c'=\sqrt{a^2-b^2}$ of elliptic coordinates, and k of polar coordinates with one attracting focus is replaced by 2k of elliptic coordinates with two attracting foci. In elliptic coordinates, k is given by Eqs. (58) and (60)

$$k = \frac{2pe^2}{4\pi\varepsilon_o} \qquad (75)$$

and L for the electron equals $\hbar$; thus, in elliptic coordinates $$c' = a\sqrt{\frac{\hbar^2 4\pi\varepsilon_o}{me^2 2pa}} = \sqrt{\frac{aa_0}{2p}} \qquad (76)$$

Substitution of a given by Eq. (68) into Eq. (76) gives $$c' = \frac{a_0}{p} \qquad (77)$$

The internuclear distance from Eq. (77) is $$2c' = \frac{2a_o}{p}. \qquad$$

One half the length of the semiminor axis of the prolate spheroidal MO, b=c, is $$b=\sqrt{a^2-c'^2} \qquad (78)$$

Substitution of $$a = \frac{2a_o}{p}$$

into Eq. (78) gives $$b = \frac{\sqrt{3}}{p} a_o \qquad (79)$$

The eccentricity, e, is $$e = \frac{c'}{a} \qquad (80)$$

Substitution of $$a = \frac{2a_o}{p} \text{ and } c' = \frac{a_o}{p}$$

into Eq. (80) gives $$e = \frac{1}{2} \qquad (81)$$

The potential energy, $V_p$, due to proton-proton repulsion in the field of magnitude p times that of the protons at the foci ($\xi$=0) is $$V_p = \frac{pe^2}{8\pi\varepsilon_o\sqrt{a^2-b^2}} \qquad (82)$$

The total energy $E_T$ is given by the sum of the energy terms $$E_T = V_e + V_p + T \qquad (83)$$

Substitution of a and b given by Eqs. (68) and (79), respectively, into Eqs. (69), (71), (82), and (83) gives $$V_e = \frac{-4p^2 e^2}{8\pi\varepsilon_o a_o} \ln 3 \qquad (84)$$

$$V_p = \frac{p^2 e^2}{8\pi\varepsilon_o a_o} \qquad (85)$$

$$T = \frac{2p^2 e^2}{8\pi\varepsilon_o a_o} \ln 3 \qquad (86)$$

$$E_T = -13.6 \text{ eV}(4p^2 \ln 3 - p^2 - 2p^2 \ln 3) = -p^2 16.28 \text{ eV} \qquad (87)$$

1.D. Vibration of Hydrogen-Type Molecular Ions

A charge, q, oscillating according to $r_0(t)=d \sin \omega_0 t$ has a Fourier spectrum $$J(k,\omega) = \frac{q\omega_0 d}{2} J_m(k\cos\theta d)\{\delta[\omega-(m+1)\omega_0] + \delta[\omega-(m-1)\omega_0]\} \qquad (88)$$

where $J_m$'s are Bessel functions of order m. These Fourier components can, and do, acquire phase velocities that are equal to the velocity of light [28]. The protons of hydrogen-type molecular ions and molecules oscillate as simple harmonic oscillators; thus, vibrating protons will radiate. Moreover, nonoscillating protons may be excited by one or more photons that are resonant with the oscillatory resonance frequency of the molecule or molecular ion, and oscillating protons may be further excited to higher energy vibrational states by resonant photons. The energy of a photon is quantized according to Planck's equation $$E = \hbar\omega \qquad (89)$$

The energy of a vibrational transition corresponds to the energy difference between the initial and final vibrational states. Each state has an electromechanical resonance frequency, and the emitted or absorbed photon is resonant with the difference in frequencies. Thus, as a general principle, quantization of the vibrational spectrum is due to the quantized energies of photons and the electromechanical resonance of the vibrationally excited ion or molecule.

It is shown by Fowles [75] that a perturbation of the orbit determined by an inverse-squared force results in simple harmonic oscillatory motion of the orbit. In a circular orbit in spherical coordinates, the transverse equation of motion gives $$\dot{\theta} = \frac{L/m}{r^2} \qquad (90)$$

where L is the angular momentum. The radial equation of motion is $$m(\ddot{r}-r\dot{\theta}^2)=f(r) \qquad (91)$$

Substitution of Eq. (90) into Eq. (91) gives $$m\ddot{r} - \frac{m(L/m)^2}{r^3} = f(r) \qquad (92)$$

For a circular orbit, r is a constant and $\ddot{r}=0$. Thus, the radial equation of motion is given by $$-\frac{m(L/m)^2}{a^3} = f(a) \qquad (93)$$

where a is the radius of the circular orbit for central force, $f(a)$, at r=a. A perturbation of the radial motion may be expressed in terms of a variable x defined by $$x=r-a \qquad (94)$$

The differential equation can then be written as $$m\ddot{x}-m(L/m)^2(x+a)^{-3}=f(x+a) \qquad (95)$$

Expanding the two terms involving x+a as a power series in x, gives $$m\ddot{x} - m(L/m)^2 a^{-3}\left(1 - 3\frac{x}{a} + \ldots\right) = f(a) + f'(a)x + \ldots \qquad (96)$$

Substitution of Eq. (93) into Eq. (96) and neglecting terms involving $x^2$ and higher powers of x gives $$m\ddot{x} + \left[\frac{-3}{a}f(a) - f'(a)\right]x = 0 \qquad (97)$$

For an inverse-squared central field, the coefficient of x in Eq. (97) is positive, and the equation is the same as that of the simple harmonic oscillator. In this case, the particle, if perturbed, oscillates harmonically about the circle r=a, and an approximation of the angular frequency of this oscillation is $$\omega = \sqrt{\frac{\left[\frac{-3}{a}f(a) - f'(a)\right]}{m}} = \sqrt{\frac{k}{m}} \qquad (98)$$

An apsis is a point in an orbit at which the radius vector assumes an extreme value (maximum or minimum). The angle swept out by the radius vector between two consecutive apsides is called the apsidal angle. Thus, the apsidal angle is π for elliptic orbits under the inverse-squared law of force. In the case of a nearly circular orbit, Eq. (97) shows that r oscillates about the circle r=a, and the period of oscillation is given by $$\tau_r = 2\pi \sqrt{\frac{m}{-\left[\frac{-3}{a}f(a) + f'(a)\right]}} \qquad (99)$$

The apsidal angle in this case is just the amount by which the polar angle θ increases during the time that r oscillates from a minimum value to the succeeding maximum value which is $\tau_r$. From Eq. (90), $$\dot{\theta} = \frac{L/m}{r^2};$$

therefore, θ remains constant, and Eq. (93) gives $$\dot{\theta} \approx \frac{L/m}{a^2} = \left[-\frac{f(a)}{ma}\right]^{1/2} \qquad (100)$$

Thus, the apsidal angle is given by $$\psi = \frac{1}{2}\tau_r \dot{\theta} = \pi\left[3 + a\frac{f'(a)}{f(a)}\right]^{1/2} \qquad (101)$$

Thus, the power force of $f(r)=-cr^n$ gives $$\psi = \pi(3+n)^{-1/2} \qquad (102)$$

The apsidal angle is independent of the size of the orbit in this case. The orbit is re-entrant, or repetitive, in the case of the inverse-squared law (n=−2) for which ψ=π.

A prolate spheroid MO and the definition of axes are shown in FIGS. 1A and 1B, respectively. Consider the two nuclei A and B, each at focus of the prolate spheroid MO. From Eqs. (65), (67), (69), and (71), the attractive force between the electron and each nucleus at a focus is $$f(a) = -\frac{pe^2}{4\pi\varepsilon_o a^2} \qquad (103)$$

and $$f'(a) = \frac{2pe^2}{4\pi\varepsilon_o a^3} \qquad (104)$$

In addition to the attractive force between the electron and the nuclei, there is a repulsive force between the two nuclei that is the source of a corresponding reactive force on the reentrant electron orbit. Consider an elliptic geodesic of the MO in the xy-plane with a nucleus A at (−c', 0) and a nucleus B at (c', 0). For B acting as the attractive focus, the reactive repulsive force at the point (a, 0), the positive semimajor axis, depends on the distance from (a, 0) to nucleus A at (-c', 0) (i.e. the distance from the position of the electron MO at the semimajor axis to the opposite nuclear repelling center at the opposite focus). The distance is given by the sum of the semimajor axis a and c', ½ the internuclear distance. The contribution from the repulsive force between the two protons is $$f(a+c') = \frac{pe^2}{8\pi\varepsilon_o(a+c')^2} \quad (105)$$

and $$f'(a+c') = -\frac{pe^2}{4\pi\varepsilon_o(a+c')^3} \quad (106)$$

Thus, from Eqs. (98) and (103–106), the angular frequency of this oscillation is $$\omega = \sqrt{\frac{\frac{pe^2}{4\pi\varepsilon_o a^3} - \frac{pe^2}{8\pi\varepsilon_o(a+c')^3}}{\mu}} \quad (107)$$

$$= \sqrt{\frac{\frac{pe^2}{4\pi\varepsilon_o\left(\frac{2a_H}{p}\right)^3} - \frac{pe^2}{8\pi\varepsilon_o\left(\frac{3a_H}{p}\right)^3}}{\mu}}$$

$$= p^2 4.44865 \times 10^{14} \text{ rad/s}$$

where the semimajor axis, a, is $$a = \frac{2a_H}{p}$$

according to Eq. (68) and c' is $$c' = \frac{a_H}{p}$$

according to Eq. (77).

In the case of a hydrogen molecule or molecular ion, the electrons which have a mass of $1/1836$ that of the protons move essentially instantaneously, and the charge density is that of a continuous membrane. Thus, a stable electron orbit is maintained with oscillatory motion of the protons. Hydrogen molecules and molecular ions are symmetrical along the semimajor axis; thus, the oscillatory motion of protons is along this axis. Let x be the increase in the semimajor due to the reentrant orbit with a corresponding displacement of the protons along the semimajor axis from the position of the initial foci of the stationary state. The equation of proton motion due to the perturbation of an orbit having an inverse-squared central force [72] and neglecting terms involving $x^2$ and higher is given by $$\mu\ddot{x}+kx=0 \quad (108)$$

which has the solution in terms of the maximum amplitude of oscillation, A, the reduced nuclear mass, $\mu$, the restoring constant or spring constant, k, the resonance angular frequency, $\omega_0$, and the vibrational energy, $E_{vib}$, [76]

$$A \cos \omega_0 t \quad (109)$$

where $$\omega_0 = \sqrt{\frac{k}{\mu}} \quad (110)$$

For a symmetrical displacement, x, the potential energy corresponding to the oscillation, $E_{Pvib}$, is given by $$E_{Pvib} = 2\left(\frac{1}{2}kx^2\right) = kx^2 \quad (111)$$

The total energy of the oscillating molecular ion, $E_{Totalvib}$, is given as the sum of the kinetic and potential energies $$E_{Totalvib} = \frac{1}{2}\mu x'^2 + kx^2 \quad (112)$$

The velocity is zero when x is the maximum amplitude, A. The total energy of the oscillating molecular ion, $E_{Totalvib}$, is then given as the potential energy with x=A $$E_{Totalvib}=kA^2 \quad (113)$$

Thus, $$A = \sqrt{\frac{E_{Totalvib}}{k}} \quad (114)$$

It is shown in the Excited States of the One Electron Atom (Quantization) section of Ref. [5] that the change in angular frequency of the electron orbitsphere, Eq. (2.21) of Ref. [5], is identical to the angular frequency of the photon necessary for the excitation, $\omega_{photon}$, (Eq. (2.19) of Ref. [5]). The energy of the photon necessary to excite the equivalent transition in an electron orbitsphere is one-half of the excitation energy of the stationary cavity because the change in kinetic energy of the electron orbitsphere supplies one-half of the necessary energy. The change in the angular frequency of the orbitsphere during a transition and the angular frequency of the photon corresponding to the superposition of the free space photon and the photon corresponding to the kinetic energy change of the orbitsphere during a transition are equivalent. The correspondence principle holds. It can be demonstrated that the resonance condition between these frequencies is to be satisfied in order to have a net change of the energy field [27]. The bound electrons are excited with the oscillating protons. Thus, the mechanical resonance frequency, $\omega_0$, is only one-half that of the electromechanical frequency which is equal to the angular frequency of the free space photon, $\omega$, which excites the vibrational mode of the hydrogen molecule or hydrogen molecular ion. The vibrational energy, $E_{vib}$, corresponding to the photon is given by $$E_{vib} = \hbar\omega = \hbar\omega_0 = \hbar\sqrt{\frac{k}{\mu}} = 2kA^2 \tag{115}$$

where Planck's equation (Eq. (89)) was used. The reduced mass is given by $$\mu = \frac{m_1 m_2}{m_1 + m_2} \tag{116}$$

Thus, $$A = \sqrt{\frac{\hbar\omega_0}{2k}} \tag{117}$$

Since the protons and electron are not fixed, but vibrate about the center of mass, the maximum amplitude is given by the reduced amplitude, $A_{reduced}$, given by $$A_{reduced} = \frac{A_1 A_2}{A_1 + A_2} \tag{118}$$

where $A_n$ is the amplitude n if the origin is fixed. Thus, Eq. (117) becomes $$A_{reduced} = \frac{1}{2}\sqrt{\frac{\hbar\omega_0}{2k}} \tag{119}$$

and from Eq. (110), $A_{reduced}$ is $$A_{reduced} = \frac{1}{2}\sqrt{\frac{\hbar\omega_0}{2k}} = \frac{1}{2}\sqrt{\frac{\hbar}{2k}}\left(\frac{k}{\mu}\right)^{1/4} = \frac{\sqrt{\hbar}}{2^{3/2}(k\mu)^{1/4}} \tag{120}$$

Then, from Eq. (80), $A_{c'}$, the displacement of c' is the eccentricity e given by Eq. (81) times $A_{reduced}$ (Eq. (120)):

$$A_{c'} = eA_{reduced} = \frac{A_{reduced}}{2} = \frac{\sqrt{\hbar}}{2^{5/2}(k\mu)^{1/4}} \tag{121}$$

Thus, during bond formation, the perturbation of the orbit determined by an inverse-squsred force results in simple harmonic oscillatory motion of the orbit, and the coresponding frequency, $\omega(0)$, for a hydrogen-type molecular ion $H_2^+(1/p)$ given by Eqs. (98) and (107) is $$\omega(0) = p^2\sqrt{\frac{k(0)}{\mu}} \tag{122}$$

$$= p^2\sqrt{\frac{165.51 \text{ Nm}^{-1}}{\mu}} = p^2 4.449 \times 10^{14} \text{ radians/s}$$

where the reduced nucear mass of hydrogen given by Eq.(116) is $$\mu = 0.5 \, m_p \tag{123}$$

and dthe spring constant, k(0), given by Eqs. (98) and (107) is $$(0) = {}^4 165.51 \text{ Nm}^{31} \, {}^1 \tag{124}$$

The transition-state vibrational energy, $E_{vib}(0)$, is given by Planck's equation (Eq. (89)):

$$E_{vib}(0) = \hbar\omega = \hbar p^4 4.44865 \times 10^{14} \text{ rad/s} = p^2 0.2982 \text{ eV} \tag{125}$$

The amplidtude of the oscillation, $A_{reduced}(0)$, given by Eq. (120) and Eqs. (123–124) is $$A_{reduced}(0) = \frac{\sqrt{\hbar}}{2^{3/2}(p^4 165.51 \text{ Nm}^{-1}\mu)^{1/4}} \tag{126}$$

$$= \frac{5.952 \times 10^{-12} \text{ m}}{p}$$

$$= 0.1125 \frac{a_o}{p}$$

Then, from Eq. (80), $A_{c'}(0)$, the displacement of c', is the eccentricity e given by Eq. (81) time $A_{reduced}(0)$ (Eq. (126)):

$$A_{c'}(0) = eA_{reduced}(0) = \frac{A_{reduced}(0)}{2} = \frac{\sqrt{\hbar}}{2^{5/2}(k\mu)^{1/4}} = \frac{0.05625 a_o}{p} \tag{127}$$

The spring constant and vibrational frequency for the formed molecular ion are then obtained from Eqs. (98) and (103–107using the increases in the semimajor axis and internuclear distances due to vibration in the transition state. The vibrational energy, $E_{vib}(1)$, for the $H_2^+(1/p)$ $\upsilon = \to \upsilon = 0$ transition given by adding $A_{c'}(0)$ (Eq. (121)) to the distance a and a+c' in Eqs. (107) and (125) is $$E_{vib}(1) = p^2 0.270 \text{ eV} \tag{128}$$

where $\upsilon$ is the vibrational quantum number.

A harmonic oscillator is a linear system as given by Eq. (108). In this case, the predicted resonant vibrational frequencies and energies, spring constants, and amplitudes for $H_2^+(1/p)$ for vibrational transitions to higher energy $\upsilon_i \to \upsilon_f$ are given by $(\upsilon_f \to \upsilon_i)$ times the corresponding parameters given by Eq. (122) and Eqs. (124–128). However, excitation of vibration of the molecular ion by eternal radiation causes the semimajor axis and, consequently, the internuclear distance to increase as a function of the vibrational quantum number, $\upsilon$. Consequently, the vibrational energies of hydrogen-type molecular ions are nonlinear as a function of the vibrational quantum number, $\upsilon$. The lines become more closely spaced and the change in amplitude, $\Delta A_{reduced}$, between successive states larger as higher states are excited due to the distortion of the molecular ion in these states. The energy difference of each successive transition of the vibrational spectrum can be obtained by considering nonlinear terms corresponding to anharmonicity.

The harmonic oscillator potential energy function can be expanded about the internuclear distance and expressed as a Maclaurin series corresponding to a Morse potential after Karplus and Porter (K&P) [8] and after Eq. (96). Treating the Maclaurin series terms as anharmonic perturbation terms of the harmonic states, the energy corrections can be found by perturbation methods. The energy $\tilde{\nu}_\upsilon$ of state $\upsilon$ is $$\tilde{\nu}_\upsilon = \upsilon\omega_0 - \upsilon(\upsilon-1)\omega_0 x_0, \quad \upsilon 0,1,2,3 \tag{129}$$

where $$\omega_0 x_0 = \frac{hc\omega_0^2}{4D_0} \quad (130)$$

$\omega$ is frequency of the $\upsilon=1 \rightarrow \upsilon=0$ transition corresponding to Eq. (128) and $D_0$ is the bond dissociation energy given by Eq. (160). From Eqs. (130), and (160), $$\omega_0 x_0 = \frac{100\,hc\left(8.06573 \times 10^3 \frac{cm^{-1}}{eV} p^2 0.270\,eV\right)^2}{4e(p^2 2.535\,eV + p^3 0.118755\,eV)} cm^{-1} \quad (131)$$

The vibrational energies of successive states are given by Eqs. (128–131).

Using Eqs. (107), (120–122), (124–131), and Eq. (161) the corresponding parameters for deuterium-type molecular ions with $$\mu = m_p \text{ are} \quad (132)$$

$$\omega(0) = p^2 \sqrt{\frac{k(0)}{\mu}} \quad (133)$$

$$= p^2 \sqrt{\frac{165.65 \text{ Nm}^{-1}}{\mu}}$$

$$= p^2 3.147 \times 10^{14} \text{ radians/s}$$

$$k(0) = p^4 165.65 \text{ Nm}^{-1} \quad (134)$$

$$E_{vib}(0) = p^2 0.20714 \text{ eV} \quad (135)$$

$$A_{reduced}(0) = \frac{\sqrt{\hbar}}{2^{3/2}(p^4 165.65 \text{ Nm}^{-1}\mu)^{1/4}} \quad (136)$$

$$= \frac{5.004 \times 10^{-12} \text{ m}}{p}$$

$$= 0.09457 \frac{a_o}{p}$$

$$E_{vib}(1) = p^2 0.193 \text{ eV} \quad (137)$$

$$\omega_0 x_0 = \frac{100\,hc\left(8.06573 \times 10^3 \frac{cm^{-1}}{eV} p^2 0.193\,eV\right)^2}{4e(p^2 2.5770\,eV + p^3 0.118811\,eV)} cm^{-1} \quad (138)$$

The vibrational energy of successive states are given by Eqs. (129) and (137–138).

1.E. The Doppler Energy Term of Hydrogen-type Molecular Ions

As shown in Sec. IV.1.D, the electron orbiting the nuclei at the foci of an ellipse may be perturbed such that a stable reentrant orbit is established that gives rise to a vibrational state corresponding to time harmonic oscillation of the nuclei and electron. The perturbation is caused by a photon that is resonant with the frequency of oscillation of the nuclei wherein the radiation is electric dipole with the corresponding selection rules.

Oscillation may also occur in the transition state. The perturbation arises from the decrease in internuclear distance as the molecular bond forms. Relative to the unperturbed case given in Sec. IV.1.B, the reentrant orbit may give rise to a decrease in the total energy while providing a transient kinetic energy to the vibrating nuclei. However, as an additional condition for stability, radiation must be considered. Regarding the potential for radiation, the nuclei may be considered point charges. A point charge under going periodic motion accelerates and as a consequence radiates according to the Larmor formula (cgs units) [77]:

$$P = \frac{2e^2}{3c^3}|\dot{v}|^2 \quad (139)$$

where e is the charge, $\tilde{v}$ is its acceleration, and c is the speed of light. The radiation has a corresponding force that can be determined based on conservation of energy with radiation. The radiation reaction force, $F_{rad}$, given by Jackson [78] is $$F_{rad} = \frac{2}{3}\frac{e^2}{c^3}\ddot{v} \quad (140)$$

Then, the Abraham-Lorentz equation of motion is given by [78]

$$m\left(\dot{v} - \frac{2}{3}\frac{e^2}{mc^3}\ddot{v}\right) = F_{ext} \quad (141)$$

where $F_{ext}$ the external force and m is the mass. The external force for the vibrating system is given by Eq. (108).

$$F_{ext} = kz \quad (142)$$

where x is the displacement of the protons along the semi-major axis from the position of the initial foci of the stationary state in the absence of vibration with a reentrant orbit of the electron. A nonradiative state must be achieved after the emission due to transient vibration wherein the nonradiative condition given by Eq. (34) must be satisfied.

As shown in the Resonant Line Shape and Lamb Shift section of Ref. [5], the spectroscopic linewidth arises from the classical rise-time band-width relationship, and the Lamb Shift is due to conservation of energy and linear momentum and arises from the radiation reaction force between the electron and the photon. The radiation reaction force in the case of the vibration of the molecular ion in the transition state corresponds to a Doppler energy, $E_D$, that is dependent on the motion of the electron and the nuclei. The Doppler energy of the electron is given by Eq. (2.72) of Ref. [5]:

$$\overline{E}_D \cong 2\sqrt{E_K E_R} = E_{h\nu}\sqrt{\frac{2\overline{E}_K}{Mc^2}} \quad (143)$$

where $E_R$ is the recoil energy which arises from the photon's linear momentum given by Eq. (2.67) of Ref. [5], $E_K$ is the vibrational kinetic energy of the reentrant orbit in the transition state, and M is the mass of the electron $m_e$.

As given in Sec. IV.1.D, for inverse-squared central field, the coefficient of x in Eq. (97) is positive, and the equation is the same as that of the simple harmonic oscillator. Since the electron of the hydrogen molecular ion is perturbed as the internuclear separation decreases with bond formation, it oscillates harmonically about the semimajor axis given by Eq. (68), and an approximation of the angular frequency of this oscillation is $$\omega = \sqrt{\frac{\left[\frac{-3}{a}f(a) - f'(a)\right]}{m_e}} = \sqrt{\frac{k}{m_e}} \tag{144}$$

from Eqs. (65), (67), (69), and (71), the central force terms between the electrons MO and the two protons are $$f(a) = -\frac{2pe^2}{4\pi\varepsilon_o a^2} \text{ and} \tag{145}$$

$$f'(a) = \frac{4pe^2}{4\pi\varepsilon_o a^3} \tag{146}$$

Thus, the angular frequency of this oscillation is $$\omega = \sqrt{\frac{\frac{2pe^2}{4\pi\varepsilon_o \left(\frac{2a_H}{p}\right)^3}}{m_e}} = p^2 2.06538 \times 10^{16} \text{ rad/s} \tag{147}$$

where the semimajor axis, $a$, is $$a = \frac{2a_H}{p}$$

according to Eq. (68) including the reduced electron mass. The kinetic energy, $E_K$, is given by Plank's equation (Eq. (89)):

$$\overline{E}_K = \hbar\omega = \hbar p^2 2.06538 \times 10^{16} \text{ rad/s} = p^2 13.594697 \text{ eV} \tag{148}$$

In Eq. (143), substitution of the total energy of the hydrogen molecular ion, $E_T$, (Eq. (87)) for $E_{h\nu}$, the mass of the electron, $m_e$, for M, and the kinetic energy given by Eq. (148) for $\overline{E}_K$ gives the Doppler energy of the electron for the reentrant orbit.

$$\overline{E}_D \cong E_{h\nu}\sqrt{\frac{2\overline{E}_K}{Mc^2}} \tag{149}$$

$$= -p^2 16.28034 \text{ eV} \sqrt{\frac{2e(p^2 13.594697 \text{ eV})}{m_e c^2}}$$

$$= -p^3 0.118755 \text{ eV}$$

The total energy of the molecular ion is decreased by $\overline{E}_D$.

In addition to the electron, the nuclei also undergo simple harmonic oscillation in the transition state of their corresponding frequency given in Sec. IV.1.D. On average, the total energy of vibration is equally distributed between kinetic energy and potential energy [79]. Thus, the average kinetic energy of vibration corresponding to the Doppler energy of the electrons, $\overline{E}_{Kvib}$, is ½ of the vibrational energy of the molecular ion given by Eq. (125). The decrease in the energy of the hydrogen molecular ion due to the reentrant orbit in the transition state corresponding to simple harmonic oscillation of the electron and nuclei, $\overline{E}_{osc}$, is given by sum of the corresponding energies, $\overline{E}_D$ and $\overline{E}_{Kvib}$. Using Eq. (149) and $E_{vib}$ from Eq. (125) gives $$\overline{E}_{osc} = \overline{E}_D + \overline{E}_{Kvib} = \overline{E}_D + \frac{1}{2}\hbar p^2 \sqrt{\frac{k}{\mu}} \tag{150}$$

$$\overline{E}_{osc} = -p^3 0.118755 \text{ eV} + \frac{1}{2}p^2(0.29282 \text{ eV}) \tag{151}$$

To the extent that the MO dimensions are the same, the electron reentrant orbital energies, $\overline{E}_K$, are the same independent of the isotope of hydrogen, but the vibrational energies are related by Eq. (110). Thus, the differences in bond energies are essentially given by ½ the differences in vibrational energies. Using Eq. (149) with the deuterium reduced electron mass for $\overline{E}_T$ and $\overline{E}_D$, and $E_{vib}$ for $D_2^+(1/p)$ given by Eq. (135), that corresponds to the deuterium reduced nuclear mass (Eq. (132)), the corresponding $\overline{E}_{osc}$ is $$\overline{E}_{osc} = -p^3 0.118811 \text{ eV} + \frac{1}{2}p^2(0.20714 \text{ eV}) \tag{152}$$

1.F. Total (Ionization) and Bond Energies of Hydrogen and Deuterium Molecular Ions The total energy of the hydrogen molecular ion which is equivalent to the negative of the ionization energy is given by the sum of $E_T$ (Eqs. (83) and (87)) and $\overline{E}_{osc}$ given by Eqs. (147–150). Thus, the total energy of the hydrogen molecular ion having a central field of +pe at each focus of the prolate spheroid molecular orbital including the Doppler term is $$E_T = V_e + V_p + T + \overline{E}_{osc} \tag{153}$$

$$E_T = -p^2 \left\{ \left[ \frac{\frac{e^2}{8\pi\varepsilon_o a_H}(4\ln 3 - 1 - 2\ln 3)}{1 + p\sqrt{\frac{2\hbar\sqrt{\frac{2e^2}{4\pi\varepsilon_o(2a_H)^3}}}{m_e c^2}}} \right] - \frac{1}{2}\hbar\sqrt{\frac{k}{\mu}} \right\} \tag{154}$$

$$= -p^2 16.2803 \text{ eV} - p^3 0.118811 \text{ eV} + \frac{1}{2}p^2\hbar\sqrt{\frac{k}{\mu}}$$

From Eqs. (151) and (153–154), the total energy for hydrogen-type molecular ions is $$E_T = -p^2 16.28033 \text{ eV} + \overline{E}_{osc} \tag{155}$$

$$= -p^2 16.28033 \text{ eV} - p^3 0.118755 \text{ eV} +$$

$$\frac{1}{2}p^2(0.29282 \text{ eV})$$

$$= -p^2 16.13392 \text{ eV} - p^3 0.118755 \text{ eV}$$

The total energy of the deuterium molecular ion is given by the sum of $E_T$ (Eq. (87)) corrected for the reduced electron mass of D and $\overline{E}_{osc}$ given by Eq. (152):

$$E_T = -p^2 16.284 \text{ eV} + \overline{E}_{osc} \tag{156}$$

$$= -p^2 16.284 \text{ eV} - p^3 0.118811 \text{ eV} + \frac{1}{2}p^2(0.20714 \text{ eV})$$

$$= -p^2 16.180 \text{ eV} - p^3 0.118811 \text{ eV}$$

The bond dissociation energy, $E_D$, is the difference between the total energy of the corresponding hydrogen atom or H(1/p) atom [37, 48], called hydrino atom having a principal quantum number 1/p where p is an integer, and $E_T$.

$$E_D = E(H(1/p)) - E_T \tag{157}$$

where [48]

$$E(H(1/p)) = -p^2 13.59844 \text{ eV} \tag{158}$$

and [37]

$$E(D(1/p)) = -p^2 13.603 \text{ eV} \tag{159}$$

The hydrogen molecular ion bond energy, $E_D$, is given by Eq. (155) with the reduced electron mass and Eqs. (157–158):

$$E_D = -p^2 13.59844 - E_T \tag{160}$$

$$= -p^2 13.59844 - (-p^2 16.13392 \text{ eV} - p^3 0.118755 \text{ eV})$$

$$= p^2 2.535 \text{ eV} + p^3 0.118755 \text{ eV}$$

The deuterium molecular ion bond energy, $E_D$, is given by Eq. (156) with the reduced electron mass of D and Eqs. (157) and (159):

$$E_D = -p^2 13.603 - E_T \tag{161}$$

$$= -p^2 13.603 - (-p^2 16.180 \text{ eV} - p^3 0.118811 \text{ eV})$$

$$= p^2 2.5770 \text{ eV} + p^3 0.118811 \text{ eV}$$

2. Hydrogen-Type Molecules

2.A. Force Balance of Hydrogen-Type Molecules

Hydrogen-type molecules comprise two indistinguishable electrons bound by an elliptic field. Each electron experiences a centrifugal force, and the balancing centripetal force (on each electron) is produced by the electric force between the electron and the elliptic electric field and the magnetic force between the two electrons causing the electrons to pair. In the present case of hydrogen-type molecules, if the eccentricity equals $$\frac{1}{\sqrt{2}},$$

then the vectorial projection of the magnetic force between the electrons, $$\sqrt{\frac{3}{4}}$$

of Eq. (7.15) of the Two Electron Atom section of Ref. [5], is one. The molecules will be solved by self consistency. Assume $$e = \frac{1}{\sqrt{2}},$$

then the force balance equation given by Eq. (7.18) of the Two Electron Atom section of Ref. [5] and Eq. (67)

$$\frac{\hbar^2}{m_e a^2 b^2} 2ab^2 X = \frac{pe^2}{4\pi\varepsilon_o} X + \frac{\hbar^2}{2m_e a^2 b^2} 2ab^2 X \tag{162}$$

$$\frac{2a_o}{pa} - \frac{a_0}{pa} = 1 \tag{163}$$

$$a = \frac{a_o}{p} \tag{164}$$

Substitution of Eq. (164) into Eq. (76) is $$c' = \frac{1}{p\sqrt{2}} a_o \tag{165}$$

Substitution of Eqs. (164–165) into Eq. (78) is $$b = c' = \frac{1}{p\sqrt{2}} a_o \tag{166}$$

Substitution of Eqs. (164–165) into Eq. (80) is $$e = \frac{1}{\sqrt{2}} \tag{167}$$

The eccentricity is $$\frac{1}{\sqrt{2}};$$

thus, the present self consistent solution which was obtained as a boundary value problem is correct. The internuclear distance given by multiplying Eq. (165) by two is $$\frac{a_o\sqrt{2}}{p}.$$

2.B. Energies of Hydrogen-Type Molecules

The energy components defined previously for the molecular ion, Eqs. (69), (71), (82), and (83), apply in the case of the corresponding molecule. And, each molecular energy component is given by the integral of corresponding force in Eq. (162) where each energy component is the total for the two equivalent electrons. The parameters a and b are given by Eqs. (164) and (166), respectively.

$$V_e = \frac{-2pe^2}{8\pi\varepsilon_o \sqrt{a^2-b^2}} \ln\frac{a+\sqrt{a^2-b^2}}{a-\sqrt{a^2-b^2}} \qquad (168)$$

$$V_p = \frac{p}{8\pi\varepsilon_o} \frac{e^2}{\sqrt{a^2-b^2}} \qquad (169)$$

$$T = \frac{\hbar^2}{2m_e a \sqrt{a^2-b^2}} \ln\frac{a+\sqrt{a^2-b^2}}{a-\sqrt{a^2-b^2}} \qquad (170)$$

The energy, $V_m$, corresponding to the magnetic force of Eq. (162) is $$V_m = \frac{-\hbar^2}{4m_e a \sqrt{a^2-b^2}} \ln\frac{a+\sqrt{a^2-b^2}}{a-\sqrt{a^2-b^2}} \qquad (171)$$

$$E_T = V_e + T + V_m + V_p \qquad (172)$$

$$E_T = -13.60 \text{ eV} \left[\left(2p^2\sqrt{2} - p^2\sqrt{2} + \frac{p^2\sqrt{2}}{2}\right)\ln\frac{\sqrt{2}+1}{\sqrt{2}-1} - p^2\sqrt{2}\right] \qquad (173)$$

$$= -p^2 31.63$$

2.C. Vibration of Hydrogen-Type Molecules

The vibrational energy levels of hydrogen-type molecules may be solved in the same manner as hydrogen-type molecular ions given in Sec. IV.1.D. The corresponding central force terms of Eq. (98) are $$f(a) = -\frac{pe^2}{8\pi\varepsilon_o a^2} \qquad (174)$$

and $$f'(a) = \frac{pe^2}{4\pi\varepsilon_o a^3} \qquad (175)$$

The distance for the reactive nuclear-repulsive terms is given by the sum of the semimajor axis, a, and c', ½ the internuclear distance. The contribution from the repulsive force between the two protons is $$f(a+c') = \frac{pe^2}{8\pi\varepsilon_o (a+c')^2} \qquad (176)$$

and $$f'(a+c') = -\frac{pe^2}{4\pi\varepsilon_o (a+c')^3} \qquad (177)$$

Thus, from Eqs. (98) and (174–177), the angular frequency of the oscillation is $$\omega = \sqrt{\frac{\frac{pe^2}{8\pi\varepsilon_o a^3} - \frac{pe^2}{8\pi\varepsilon_o (a+c')^3}}{\mu}} \qquad (178)$$

$$= \sqrt{\frac{\frac{pe^2}{8\pi\varepsilon_o \left(\frac{a_0}{p}\right)^3} - \frac{pe^2}{8\pi\varepsilon_o \left(\frac{\left(1+\frac{1}{\sqrt{2}}\right)a_0}{p}\right)^3}}{\mu}}$$

$$= p^2 8.62385 \times 10^{14} \text{ rad/s}$$

where the semimajor axis, a, is $$a = \frac{a_0}{p}$$

according to Eq. (164) and c' is $$c' = \frac{a_0}{p\sqrt{2}}$$

according to Eq. (165). Thus, during bond formation, the perturbation of the orbit determined by an inverse-squared force results in simple harmonic oscillatory motion of the orbit, and the corresponding frequency, $\omega(0)$, for a hydrogen-type molecule $H_2(1/p)$ given by Eqs. (98) and (107) is $$\omega(0) = p^2 \sqrt{\frac{k(0)}{\mu}} = p^2 \sqrt{\frac{621.98 \text{ Nm}^{-1}}{\mu}} \qquad (179)$$

$$= p^2 8.62385 \times 10^{14} \text{ radians/s}$$

where the reduced nuclear mass of hydrogen is given by Eq. (123) and the spring constant, $k(0)$, given by Eqs. (98) and (178) is $$k(0) = p^4 621.98 \text{ Nm}^{-1} \qquad (180)$$

The transition-state vibrational energy, $E_{vib}(0)$, is given by Planck's equation (Eq. (89)):

$$E_{vib}(0) = \hbar\omega = \hbar p^2 8.62385 \times 10^{14} \text{ rad/s} = p^2 0.56764 \text{ eV} \qquad (181)$$

The amplitude of oscillation, $A_{reduced}(0)$, given by Eqs. (120), (123), and (180) is $$A_{reduceds}(0) = \frac{\sqrt{\hbar}}{2^{3/2}(p^4 621.98 \text{ Nm}^{-1}\mu)^{1/4}} \qquad (182)$$

$$= \frac{4.275 \times 10^{-12} \text{ m}}{p}$$

$$= 0.08079 \frac{a_o}{p}$$

Then, from Eq. (80), $A_{c'}(0)$, the displacement of c' is the eccentricity, e, given by Eq. (167) times $A_{reduced}(0)$ (Eq. (182)):

$$A_{c'}(0) = eA_{reduced}(0) = \frac{A_{reduced}(0)}{\sqrt{2}} = \frac{\sqrt{\hbar}}{4(k\mu)^{1/4}} = \frac{0.05713 a_o}{p} \quad (183)$$

The spring constant and vibrational frequency for the formed molecule are then obtained from Eqs. (98) and (174–183) using the increases in the semimajor axis and internuclear distances due to vibration in the transition state. The vibrational energy, $E_{vib}(1)$, for the $H_2(1/p)$ $\upsilon=1\rightarrow\upsilon=0$ transition given by adding $A_{c'}(0)$ (Eq. (183)) to the distances a and a+c' in Eqs. (174–181) is $$E_{vib}(1) = p^2 0.517 \text{ eV} \quad (184)$$

where $\upsilon$ is the vibrational quantum number. Using Eq. (138) with Eqs. (184) and (213), the anharmonic perturbation term, $\omega_0 x_0$, of $H_2(1/p)$ is $$\omega_0 x_0 = \frac{100 hc \left( 8.06573 \times 10^3 \frac{\text{cm}^{-1}}{\text{eV}} p^2 0.517 \text{ eV} \right)^2}{4e(p^2 4.151 \text{ eV} + p^3 0.326469 \text{ eV})} \text{cm}^{-1} \quad (185)$$

where $\omega_0$ is the frequency of the $\upsilon=1\rightarrow\upsilon=0$ transition corresponding to Eq. (184) and $D_0$ is the bond dissociation energy given by Eq. (213). The vibrational energies of successive states are given by Eqs. (129) and (184–185).

Using the reduced nuclear mass given by Eq. (132), the corresponding parameters for deuterium-type molecules $D_2(1/p)$ (Eqs. (174–185) and (214)) are $$\omega(0) = p^2 \sqrt{\frac{k(0)}{\mu}} \quad (186)$$

$$= p^2 \sqrt{\frac{621.98 \text{ Nm}^{-1}}{\mu}}$$

$$= p^2 6.09798 \times 10^{14} \text{ radians/s}$$

$$k(0) = p^4 621.98 \text{ Nm}^{-1} \quad (187)$$

$$E_{vib}(0) = p^2 0.4014 \text{ eV} \quad (188)$$

$$A_{reduced}(0) = \frac{\sqrt{\hbar}}{2^{3/2}(p^4 621.98 \text{ Nm}^{-1}\mu)^{1/4}} \quad (189)$$

$$= \frac{3.595 \times 10^{-12} \text{ m}}{p}$$

$$= 0.06794 \frac{a_o}{p}$$

$$E_{vib}(1) = p^2 0.371 \text{ eV} \quad (190)$$

$$\omega_0 x_0 = \frac{100 hc \left( 8.06573 \times 10^3 \frac{\text{cm}^{-1}}{\text{eV}} p^2 0.371 \text{ eV} \right)^2}{4e(p^2 4.229 \text{ eV} + p^3 0.326469 \text{ eV})} \text{cm}^{-1} \quad (191)$$

The vibrational energies of successive states are given by Eqs. (129) and (190–191).

2.D. The Doppler Energy Term of Hydrogen-Type Molecules

The radiation reaction force in the case of the vibration of the molecule in the transition state also corresponds to the Doppler energy, $E_D$, given by Eq. (143) that is dependent on the motion of the electrons and the nuclei. Here, a nonradiative state must also be achieved after the emission due to transient vibration wherein the nonradiative condition given by Eq. (34) must be satisfied. Typically, a third body is required to form hydrogen-type molecules. For example, the exothermic chemical reaction of H+ H to form H' does not occur with the emission of a photon. Rather, the reaction requires a collision with a third body, M, to remove the bond energy-H+H+M→H₂+M* [46]. The third body distributes the energy from the exothermic reaction, and the end result is the $H_2$ molecule and an increase in the temperature of the system. Thus, a third body removes the energy corresponding to the additional force term given by Eq. (142). From Eqs. (65), (162), (168) and (170), the central force terms between the electron MO and the two protons are $$f(a) = -\frac{pe^2}{4\pi\varepsilon_o a^2} \quad (192)$$

and $$f'(a) = \frac{2pe^2}{4\pi\varepsilon_o a^3} \quad (193)$$

Thus, the angular frequency of this oscillation is $$\omega = \sqrt{\frac{pe^2}{4\pi\varepsilon_o \left(\frac{a_0}{p}\right)^3 m_e}} = p^2 4.13414 \times 10^{16} \text{ rad/s} \quad (194)$$

where the semimajor axis, a, is $$a = \frac{a_0}{p}$$

according to Eq. (164). The kinetic energy, $E_K$, is given by Planck's equation (Eq. (89)):

$$\overline{E}_K = \hbar\omega = \hbar p^2 4.13414 \times 10^{16} \text{ rad/s} = p^2 27.216 \text{ eV} \quad (195)$$

In Eq. (143), substitution of the total energy of the hydrogen molecule, $E_T$, (Eq. (173)) for $E_{hv}$, the mass of the electron, $m_e$, for M, and the kinetic energy given by Eq. (195) for $\overline{E}_K$ gives the Doppler energy of the electrons for the reentrant orbit.

$$\overline{E}_D \cong E_{hv} \sqrt{\frac{2\overline{E}_K}{Mc^2}} = -31.635 p^2 \text{ eV} \sqrt{\frac{2e(p^2 27.216 \text{ eV})}{m_e c^2}} \quad (196)$$

$$= -p^3 0.326469 \text{ eV}$$

The total energy of the molecule is decreased by $\overline{E}_D$.

In addition to the electrons, the nuclei also undergo simple harmonic oscillation in the transition state at their corresponding frequency given in Sec. IV.2.C. On average, the total energy of vibration is equally distributed between kinetic energy and potential energy [79]. Thus, the average kinetic energy of vibration corresponding to the Doppler energy of the electrons, $\overline{E}_{Kvib}$, is ½ of the vibrational energy of the molecule given by Eq. (110). The decrease in the energy of the hydrogen molecule due to the reentrant orbit in the transition state corresponding to simple harmonic oscillation of the electrons and nuclei, $\overline{E}_{osc}$ is given by the sum of the corresponding energies, $\overline{E}_D$ and $\overline{E}_{Kvib}$. Using Eq. (196) and $E_{vib}$ from Eq. (181) gives $$\overline{E}_{osc} = \overline{E}_D + \overline{E}_{Kvib} = \overline{E}_D + \frac{1}{2}\hbar p^2 \sqrt{\frac{k}{\mu}} \qquad (197)$$

$$\overline{E}_{osc} = -p^3 0.326469 \text{ eV} + \frac{1}{2} p^2 (0.56764 \text{ eV}) \qquad (198)$$

To the extent that the MO dimensions are the same, the electron reentrant orbital energies, $\overline{E}_K$, are the same independent of the isotope of hydrogen, but the vibrational energies are related by Eq. (110). Thus, the differences in bond energies are essentially given by ½ the differences in vibrational energies. Using Eq. (196) and $E_{vib}$ for $D_2(1/p)$ given by Eq. (188), that corresponds to the deuterium reduced nuclear mass (Eq. (132)), the corresponding $\overline{E}_{osc}$ is $$\overline{E}_{osc} = -p^3 0.326469 \text{ eV} + \frac{1}{2} p^2 (0.401380 \text{ eV}) \qquad (199)$$

2.E. Total, Ionization, and Bond Energies of Hydrogen and Deuterium Molecules

The total energy of the hydrogen molecule is given by the sum of $E_T$ (Eqs. (172–173)) and $\overline{E}_{osc}$ given Eqs. (194–197). Thus, the total energy of the hydrogen molecule having a central field of +pe at each focus of the prolate spheroid molecular orbital including the Doppler term is $$E_T = V_e + T + V_m + V_p + \overline{E}_{osc} \qquad (200)$$

$$E_T = -p^2 \left\{ \frac{e^2}{8\pi\varepsilon_0 a_0}\left[\left(2\sqrt{2} - \sqrt{2} + \frac{\sqrt{2}}{2}\right)\ln\frac{\sqrt{2}+1}{\sqrt{2}-1} - \sqrt{2}\right] \left[1 + p\sqrt{\frac{2\hbar\sqrt{\frac{e^2}{4\pi\varepsilon_0 a_0^3}}}{m_e c^2}}\right] - \frac{1}{2}\hbar\sqrt{\frac{k}{\mu}} \right\}$$

$$= -p^2 31.635 \text{ eV} - p^3 0.326469 \text{ eV} + \frac{1}{2}\hbar\sqrt{\frac{k}{\mu}} \qquad (201)$$

From Eqs. (198) and (200–201), the total energy for hydrogen-type molecules is $$E_T = -p^2 31.635 \text{ eV} + \overline{E}_{osc} \qquad (202)$$

$$= -p^2 31.635 \text{ eV} - p^3 0.326469 \text{ eV} + \frac{1}{2} p^2 (0.56764 \text{ eV})$$

$$= -p^2 31.351 \text{ eV} - p^3 0.326469 \text{ eV}$$

The total energy of the deuterium molecule is given by the sum of $E_T$ (Eq. (173)) and $\overline{E}_{osc}$ given by Eq. (199):

$$E_T = -p^2 31.635 \text{ eV} + \overline{E}_{osc} \qquad (203)$$

$$= -p^2 31.635 \text{ eV} - p^3 0.326469 \text{ eV} + \frac{1}{2} p^2 (0.401380 \text{ eV})$$

$$= -p^2 31.4345 \text{ eV} - p^3 0.326469 \text{ eV}$$

The first ionization energy of the hydrogen molecule, $IP_1$, $$H_2(1/p) \rightarrow H_2^+(1/p) + e^- \qquad (204)$$

is given by the difference of Eqs. (155) and (202):

$$IP_1 = E_T(H_2^+(1/p)) - E_T(H_2(1/p)) \qquad (205)$$

$$= -p^2 16.13392 \text{ eV} - p^3 0.118755 \text{ eV} -$$

$$(-p^2 31.351 \text{ eV} - p^3 0.326469 \text{ eV})$$

$$= p^2 15.2171 \text{ eV} + p^3 0.207714 \text{ eV}$$

The second ionization energy, $IP_2$, is given by the negative of Eq. (155).

$$IP_2 = p^2 16.13392 \text{ eV} + p^3 0.118755 \text{ eV} \qquad (206)$$

The first ionization energy of the deuterium molecule, $IP_1$, $$D_2(1/p) \rightarrow D_2^+(1/p) + e^- \qquad (207)$$

is given by the difference of Eqs. (156) and (203):

$$IP_1 = E_T(D_2^+(1/p)) - E_T(D_2(1/p)) \qquad (208)$$

$$= -p^2 16.180 \text{ eV} - p^3 0.118811 \text{ eV} -$$

$$(-p^2 31.4345 \text{ eV} - p^3 0.326469 \text{ eV})$$

$$= p^2 15.255 \text{ eV} + p^3 0.2077 \text{ eV}$$

The second ionization energy, $IP_2$, is given by the negative of Eq. (156).

$$IP_2 = p^2 16.180 \text{ eV} + p^3 0.118811 \text{ eV} \qquad (209)$$

The bond dissociation energy, $E_D$, is the difference between the total energy of the corresponding hydrogen atoms and $E_T$ $$E_D = E(2H(1/p)) - E_T \qquad (210)$$

where [48]

$$E(2H(1/p)) = -p^2 27.20 \text{ eV} \qquad (211)$$

and [37]

$$E(2D(1/p)) = -p^2 27.206 \text{ eV} \qquad (212)$$

The hydrogen bond energy, $E_D$, is given by Eqs. (210–211) and (202):

$$E_D = -p^2 27.20 \text{ eV} - E_T \qquad (213)$$

$$= -p^2 27.20 \text{ eV} - (-p^2 31.351 \text{ eV} - p^3 0.326469 \text{ eV})$$

$$= p^2 4.151 \text{ eV} + p^3 0.326469 \text{ eV}$$

The deuterium bond energy, $E_D$, is given by Eqs. (210), (212), and (203):

$$E_D = -p^2 27.206 \text{ eV} - E_T \quad (214)$$
$$= -p^2 27.206 \text{ eV} - (-p^2 31.4345 \text{ eV} - p^3 0.326469 \text{ eV})$$
$$= p^2 4.229 \text{ eV} + p^3 0.326469 \text{ eV}$$

3. The Hydrogen Molecular Ion

3.A. Force Balance of Hydrogen Molecular Ion

Force balance between the electric and centrifugal forces is given by Eq. (67) where p=1

$$\frac{\hbar^2}{m_e a^2 b^2} 2ab^2 X = \frac{e^2}{4\pi\varepsilon_o} X \quad (215)$$

which has the parametric solution given by Eq. (61) when $$a = 2a_o \quad (216)$$

The semimajor axis, a, is also given by Eq. (68) where p=1. The internuclear distance, 2c', which is the distance between the foci is given by Eq. (77) where p=1.

$$2c' = 2a_o \quad (217)$$

The experimental internuclear distance is $2a_o$. The semiminor axis is given by Eq. (79) where p=1.

$$b = \sqrt{3} a_o \quad (218)$$

The eccentricity, e, is given by Eq. (81).

$$e = \frac{1}{2} \quad (219)$$

3.B. Energies of the Hydrogen Molecular Ion

The potential energy, $V_e$, of the electron MO in the field of the protons at the foci ($\xi$=0) is given by Eq. (69) where p=1

$$V_e = \frac{-4e^2}{8\pi\varepsilon_o \sqrt{a^2 - b^2}} \ln \frac{a + \sqrt{a^2 - b^2}}{a - \sqrt{a^2 - b^2}} \quad (220)$$

The potential energy, $V_p$, due to proton-proton repulsion is given by Eq. (82) where p=1

$$V_p = \frac{e^2}{8\pi\varepsilon_o \sqrt{a^2 - b^2}} \quad (221)$$

The kinetic energy, T, of the electron MO is given by Eq. (71) where p=1.

$$T = \frac{2\hbar^2}{m_e a \sqrt{a^2 - b^2}} \ln \frac{a + \sqrt{a^2 - b^2}}{a - \sqrt{a^2 - b^2}} \quad (222)$$

Substitution of a and b given by Eqs. (216) and (218), respectively, into Eqs. (220–222) is $$V_e = \frac{-4e^2}{8\pi\varepsilon_o a_H} \ln 3 = -59.7575 \text{ eV} \quad (223)$$

$$V_p = \frac{e^2}{8\pi\varepsilon_o a_H} = 13.5984 \text{ eV} \quad (224)$$

$$T = \frac{2e^2}{8\pi\varepsilon_o a_H} \ln 3 = 29.8787 \text{ eV} \quad (225)$$

The Doppler term, $\bar{E}_{osc}$, for hydrogen and deuterium are given by Eqs. (151) and (152), respectively, where p=1

$$\bar{E}_{osc}(H_2^+) = \bar{E}_D + \bar{E}_{Kvib} \quad (226)$$
$$= -0.118755 \text{ eV} + \frac{1}{2}(0.29282 \text{ eV})$$
$$= 0.027655$$

$$\bar{E}_{osc}(D_2^+) = -0.118811 \text{ eV} + \frac{1}{2}(0.20714 \text{ eV}) \quad (227)$$
$$= -0.01524 \text{ eV}$$

The total energy, $E_T$, for the hydrogen molecular ion given by Eqs. (153–155) is $$E_T = -\left\{ \left[ \frac{e^2}{8\pi\varepsilon_o a_H}(4 \ln 3 - 1 - 2 \ln 3) \right] \left[ 1 + \sqrt{\frac{2\hbar \sqrt{\frac{2e^2}{4p\varepsilon_o(2a_H)^3}}}{m_e c^2}} \right] - \frac{1}{2}\hbar\sqrt{\frac{k}{m}} \right\} \quad (228)$$

$$= -16.2803 \text{ eV} - 0.118811 \text{ eV} + \frac{1}{2}(0.29282 \text{ eV})$$
$$= -16.2527 \text{ eV}$$

where in Eqs. (223–228), the radius of the hydrogen atom $a_H$(Eq. (1.228) of Ref. [5]) was used in place of $a_o$ to account for the corresponding electrodynamic force between the electron and the nuclei as given in the case of the hydrogen atom by Eq. (1.221) of Ref. [5]. The negative of Eq. (228) is the ionization energy of $H_2^+$ and the second ionization energy, $IP_2$, of $H_2$. From Eqs. (153–154) and (156) the total energy, $E_T$, for the deuterium molecular ion (the ionization energy of $D_2^+$ and the second ionization energy, $IP_2$, of $D_2$) is $$E_T = -16.284 \text{ eV} - 0.118811 \text{ eV} + \frac{1}{2}(0.20714 \text{ eV}) \quad (229)$$
$$= -16.299 \text{ eV}$$

The bond dissociation energy, $E_D$, is the difference between the total energy of the corresponding hydrogen atom and $E_T$. The hydrogen molecular ion bond energy, $E_D$, including the reduced electron mass given by Eq. (160) where p=1 is $$E_D = 2.535 \text{ eV} + 0.118755 \text{ eV} \quad (230)$$
$$= 2.654 \text{ eV}$$

The experimental bond energy of the hydrogen molecular ion [19] is $$E_D = 2.651 \text{ eV} \quad (231)$$

From Eq. (161) where p=1, the deuterium molecular ion bond energy, $E_D$, including the reduced electron mass of D is $$E_D = 2.5770 \text{ eV} + 0.118811 \text{ eV} \quad (232)$$
$$= 2.6958 \text{ eV}$$

The experimental bond energy of the deuterium molecular ion [80] is $$E_D = 2.691 \text{ eV} \quad (233)$$

3.C. Vibration of the Hydrogen Molecular Ion

It can be shown that a perturbation of the orbit determined by an inverse-squared force results in simple harmonic oscillatory motion of the orbit [75]. The resonant vibrational frequency for $H_2^+$ given by Eq. (122) is $$\omega(0) = \sqrt{\frac{k(0)}{\mu}} = \sqrt{\frac{165.51 \text{ Nm}^{-1}}{\mu}} = 4.449 \times 10^{14} \text{ radians/s} \quad (234)$$

wherein p=1. The spring constant, k(0), for $H_2^+$ given by Eq. (124) is $$k(0) = 165.51 \text{ Nm}^{-1} \quad (235)$$

The vibrational energy, $E_{vib}(0)$, of $H_2^+$ during bond formation given by Eq. (125) is $$E_{vib}(0) = 0.29282 \text{ eV} \quad (236)$$

The amplitude of oscillation given by Eq. (126) is $$A(0) = \frac{\sqrt{\hbar}}{2^{3/2}(165.51 \text{ Nm}^{-1}\mu)^{1/4}} \quad (237)$$
$$= 5.952 \times 10^{-12} \text{ m}$$
$$= 0.1125 a_0$$

The vibrational energy for the $H_2^+$ $\upsilon=1 \rightarrow \upsilon=0$ transition given by Eq. (128) is $$E_{vib}(1) = 0.270 \text{ eV} \quad (238)$$

The experimental vibrational energy of $H_2^+$ [8, 37] is $$E_{vib} = 0.271 \text{ eV} \quad (239)$$

The anharmonicity term of $H_2^+$ given by Eq. (131) is $$\omega_0 x_0 = 55.39 \text{ cm}^{-1} \quad (240)$$

The experimental anharmonicity term of $H_2^+$ from NIST [37] is $$\omega_e x_e = 66.2 \text{ cm}^{-1} \quad (241)$$

Higher-order terms after Eq. (96) are indicated. The vibrational energy for the $D_2^+$ $\upsilon=1 \rightarrow \upsilon=0$ transition given by Eq. (137) is $$E_{vib} = 0.193 \text{ eV} \quad (242)$$

The vibrational energy of the $D_2^+$ [37] based on calculations from experimental data is $$E_{vib} = 0.196 \text{ eV} \quad (243)$$

The anharmonicity term of $D_2^+$ given by Eq. (138) is $$\omega_0 x_0 = 27.86 \text{ cm}^{-1} \quad (244)$$

The experimental anharmonicity term of $D_2^+$ for the state $$X^2 \sum_{g}^{+1} s\sigma$$

is not given, but the term for state B $$^2 \sum_{g}^{+3} d\sigma$$

from NIST [37] is $$\omega_e x_e = 2.62 \text{ cm}^{-1} \quad (245)$$

4. The Hydrogen Molecule

4.A. Force Balance of the Hydrogen Molecule

The force balance equation for the hydrogen molecule is given by Eq. (162) where p=1

$$\frac{\hbar^2}{m_e a^2 b^2} 2ab^2 X = \frac{e^2}{4\pi\varepsilon_o} X + \frac{\hbar^2}{2m_e a^2 b^2} 2ab^2 X \quad (246)$$

which has the parametric solution given by Eq. (61) when $$a = a_o \quad (247)$$

The semimajor axis, a, is also given by Eq. (164) where p=1. The internuclear distance, 2c', which is the distance between the foci is given by Eq. (165) where p=1.

$$2c' = \sqrt{2} a_o \quad (248)$$

The experimental internuclear distance is $\sqrt{2} a_o$. The semiminor axis is given by Eq. (166) where p=1.

$$b = \frac{1}{\sqrt{2}} a_o \quad (249)$$

The eccentricity, e, is given by Eq. (167).

$$e = \frac{1}{\sqrt{2}} \quad (250)$$

The finite dimensions of the hydrogen molecule are evident in the plateau of the resistivity versus pressure curve of metallic hydrogen [42].

4.B. Energies of the Hydrogen Molecule

The energies of the hydrogen molecule are given by Eqs. (168–171) where p=1

$$V_e = \frac{-2e^2}{8\pi\varepsilon_o \sqrt{a^2-b^2}} \ln \frac{a+\sqrt{a^2-b^2}}{a-\sqrt{a^2-b^2}} = -67.8358 \text{ eV} \quad (251)$$

$$V_p = \frac{e^2}{8\pi\varepsilon_o \sqrt{a^2-b^2}} = 19.2415 \text{ eV} \quad (252)$$

$$T = \frac{\hbar^2}{2m_e a \sqrt{a^2-b^2}} \ln \frac{a+\sqrt{a^2-b^2}}{a-\sqrt{a^2-b^2}} = 33.9179 \text{ eV} \quad (253)$$

The energy, $V_m$, of the magnetic force is $$V_m = \frac{-\hbar^2}{4m_e a \sqrt{a^2-b^2}} \ln \frac{a+\sqrt{a^2-b^2}}{a-\sqrt{a^2-b^2}} = -16.9589 \text{ eV} \quad (254)$$

The Doppler terms, $\overline{E}_{osc}$, for hydrogen and deuterium molecules are given by Eqs. (198) and (199), respectively, where p=1

$$\overline{E}_{osc}(H_2) = \overline{E}_D + \overline{E}_{Kvib} \quad (255)$$
$$= -0.326469 \text{ eV} + \frac{1}{2}(0.56764 \text{ eV})$$
$$= -0.042649 \text{ eV}$$

$$\overline{E}_{osc}(D_2) = -0.326469 \text{ eV} + \frac{1}{2}(0.401380 \text{ eV}) \quad (256)$$
$$= -0.125779 \text{ eV}$$

The total energy, $E_T$, for the hydrogen molecule given by Eqs. (200–202) is $$E_T = -\left\{ \frac{e^2}{8\pi\varepsilon_o a_0}\left[\left(2\sqrt{2}-\sqrt{2}+\frac{\sqrt{2}}{2}\right)\ln\frac{\sqrt{2}+1}{\sqrt{2}-1}-\sqrt{2}\right] \right. \\ \left. \left[1+\sqrt{\frac{2\hbar\sqrt{\frac{e^2}{4\pi\varepsilon_o a_0^3}}}{m_e c^2}}\right] - \frac{1}{2}\hbar\sqrt{\frac{k}{\mu}} \right\} \quad (257)$$

$$= -31.635 \text{ eV} - 0.326469 \text{ eV} + \frac{1}{2}(0.56764 \text{ eV})$$
$$= -31.6776 \text{ eV}$$

From Eqs. (200–201) and (203), the total energy, $E_T$, for the deuterium molecule is $$E_T = -31.635 \text{ eV} - 0.326469 \text{ eV} + \frac{1}{2}(0.401380 \text{ eV}) \quad (258)$$
$$= -31.7608 \text{ eV}$$

The first ionization energies of the hydrogen and deuterium molecules, $IP_1$, (Eqs. (204) and (207)) are given by the differences in the total energy of corresponding molecular ions and molecules which are given by Eqs. (205) and (208), respectively, where p=1:

$$IP_1(H_2) = 15.2171 \text{ eV} + 0.207714 \text{ eV} \quad (259)$$
$$= 15.4248 \text{ eV}$$

$$IP_1(D_2) = 15.255 \text{ eV} + 0.2077 \text{ eV} \quad (260)$$
$$= 15.4627 \text{ eV}$$

The bond dissociation energy, $E_D$, is the difference between the total energy of two of the corresponding hydrogen atoms and $E_T$. The hydrogen molecular bond energy, $E_D$, given by Eq. (213) where p=1 is $$E_D = 4.151 \text{ eV} + 0.326469 \text{ eV} \quad (261)$$
$$= 4.478 \text{ eV}$$

The experimental bond energy of the hydrogen molecule [19] is $$E_D = 4.478 \text{ eV} \quad (262)$$

The deuterium molecular bond energy, $E_D$, given by Eq. (214) where p=1 is $$E_D = 4.229 \text{ eV} + 0.326469 \text{ eV} \quad (263)$$
$$= 4.556 \text{ eV}$$

The experimental bond energy of the deuterium molecule [19] is $$E_D = 4.556 \text{ eV} \quad (264)$$

4.C. Vibration of the Hydrogen Molecule

It can be shown that a perturbation of the orbit determined by an inverse-squared force results in simple harmonic oscillatory motion of the orbit [75]. The resonant vibrational frequency for $H_2$ given by Eq. (179) is $$\omega(0) = \sqrt{\frac{k(0)}{\mu}} \quad (265)$$
$$= \sqrt{\frac{621.98 \text{ Nm}^{-1}}{\mu}}$$
$$= 8.62385 \times 10^{14} \text{ radians/s}$$

The spring constant, k(0), for $H_2$ given by Eq. (180) is $$k(0) = 621.98 \text{ Nm}^{-1} \quad (266)$$

wherein p=1. The vibrational energy, $E_{vib}(0)$ of $H_2$ during bond formation given by Eq. (181) is $$E_{vib}(0) = 0.56764 \text{ eV} \quad (267)$$

The amplitude of oscillation given by Eq. (182) is $$A(0) = \frac{\sqrt{\hbar}}{2^{3/2}(p^4 621.98 \text{ Nm}^{-1}\mu)^{1/4}} \quad (268)$$

$$= 4.275 \times 10^{-12} \text{ m}$$

$$= 0.08079 a_0$$

The vibrational energy for the $H_2$ $\upsilon=1 \rightarrow \upsilon=0$ transition given by Eq. (184) is $$E_{vib}(1) = 0.517 \text{ eV} \quad (269)$$

The experimental vibrational energy of $H_2$ [20–21] is $$E_{vib}(1) = 0.5159 \text{ eV} \quad (270)$$

The anharmonicity term of $H_2$ given by Eq. (185) is $$\omega_0 x_0 = 120.4 \text{ cm}^{-1} \quad (271)$$

The experimental anharmonicity term of $H_2$ from Huber and Herzberg [80] is $$\omega_e x_e = 121.33 \text{ cm}^{-1} \quad (272)$$

The vibrational energy for the $D_2$ $\upsilon=1 \rightarrow \upsilon=0$ transition given by Eq. (190) is $$E_{vib} = 0.371 \text{ eV} \quad (273)$$

The experimental vibrational energy of $D_2$ [8, 37] is $$E_{vib} = 0.371 \text{ eV} \quad (274)$$

The anharmonicity term of $D_2$ given by Eq. (191) is $$\omega_e x_e = 60.93 \text{ cm}^{-1} \quad (275)$$

The experimental anharmonicity term of $D_2$ from NIST [37] is $$\omega_e x_e = 61.82 \text{ cm}^{-1} \quad (276)$$

The results of the determination of the bond, vibrational, total, and ionization energies, and internuclear distances for hydrogen and deuterium molecules and molecular ions are given in TABLE I. The calculated results are based on first principles and given in closed form equations containing fundamental constants only. The agreement between the experimental and calculated results is excellent.

TABLE I

The calculated and experimental parameters of $H_2$, $D_2$, $H_2^+$ and $D_2^+$.

| Parameter | Calculated | Experimental | Eqs. | Ref. for Exp. |
|---|---|---|---|---|
| $H_2$ Bond Energy | 4.478 eV | 4.478 eV | 261 | 19 |
| $D_2$ Bond Energy | 4.556 eV | 4.556 eV | 263 | 19 |
| $H_2^+$ Bond Energy | 2.654 eV | 2.651 eV | 230 | 19 |
| $D_2^+$ Bond Energy | 2.696 eV | 2.691 eV | 232 | 80 |
| $H_2$ Total Energy | 31.677 eV | 31.675 eV | 257 | 19, 81, 48[a] |
| $D_2$ Total Energy | 31.760 eV | 31.760 eV | 258 | 37, 80[b] |
| $H_2$ Ionization Energy | 15.425 eV | 15.426 eV | 259 | 81 |
| $D_2$ Ionization Energy | 15.463 eV | 15.466 eV | 260 | 80 |
| $H_2^+$ Ionization Energy | 16.253 eV | 16.250 eV | 228 | 19, 48[c] |
| $D_2^+$ Ionization Energy | 16.299 eV | 16.294 eV | 229 | 37, 80[d] |
| $H_2^+$ Magnetic Moment | $9.274 \times 10^{-24}$ $\mu_B$ | $9.274 \times 10^{-24}$ JT$^{-1}$ $\mu_B$ | 328–334 | 82 |
| Absolute $H_2$ Gas-Phase NMR Shift | −28.0 ppm | −28.0 ppm | 345 | 83–84 |
| $H_2$ Internuclear Distance[e] | 0.748 Å $\sqrt{2}a_o$ | 0.741 Å | 248 | 85 |
| $D_2$ Internuclear Distance[e] | 0.748 Å $\sqrt{2}a_o$ | 0.741 Å | 248 | 85 |
| $H_2^+$ Internuclear Distance | 1.058 Å $2a_o$ | 1.06 Å | 217 | 19 |
| $D_2^+$ Internuclear Distance[e] | 1.058 Å $2a_o$ | 1.0559 Å | 217 | 80 |
| $H_2$ Vibrational Energy | 0.517 eV | 0.516 eV | 269 | 20–21 |
| $D_2$ Vibrational Energy | 0.371 eV | 0.371 eV | 274 | 8, 37 |
| $H_2$ $\omega_e x_e$ | 120.4 cm$^{-1}$ | 121.33 cm$^{-1}$ | 271 | 80 |
| $D_2$ $\omega_e x_e$ | 60.93 cm$^{-1}$ | 61.82 cm$^{-1}$ | 275 | 37 |
| $H_2^+$ Vibrational Energy | 0.270 eV | 0.271 eV | 238 | 8, 37 |
| $D_2^+$ Vibrational Energy | 0.193 eV | 0.196 eV | 242 | 37 |
| $H_2$ J = 1 to J = 0 Rotational Energy[e] | 0.0148 eV | 0.01509 eV | 290 | 19 |
| $D_2$ J = 1 to J = 0 Rotational Energy[e] | 0.00741 eV | 0.00755 eV | 278–283, 290 | 19 |

TABLE I-continued

The calculated and experimental parameters of $H_2$, $D_2$, $H_2^+$ and $D_2^+$.

| Parameter | Calculated | Experimental | Eqs. | Ref. for Exp. |
|---|---|---|---|---|
| $H_2^+$ J = 1 to J = 0 Rotational Energy | 0.00740 eV | 0.00739 eV | 286 | 19 |
| $D_2^+$ J = 1 to J = 0 Rotational Energy[e] | 0.00370 eV | 0.003723 eV | 278–286 | 80 |

[a]The experimental total energy of the hydrogen molecule is given by adding the first (15.42593 eV) [81] and second (16.2494 eV) ionization energies where the second ionization energy is given by the addition of the ionization energy of the hydrogen atom (13.59844 eV) [47] and the bond energy of $H_2^+$ (2.651 eV) [19].
[b]The experimental total energy of the deuterium molecule is given by adding the first (15.466 eV) [80] and second (16.294 eV) ionization energies where the second ionization energy is given by the addition of the ionization energy of the deuteriumatom (13.603 eV) [37] and the bond energy of $D_2^+$ (2.692 eV) [80].
[c]The experimental second ionization energy of the hydrogen molecule, $IP_2$, is given by the sum of the ionization energy of the hydrogen atom (13.59844 eV) [47] and the bond energy of $H_2^+$ (2.651 eV) [19].
[d]The experimental second ionization energy of the deuterium molecule, $IP_2$, is given by the sum of the ionization energy of the deuterium atom (13.603 eV) [37] and the bond energy of $D_2^+$ (2.692 eV) [80].
[e]Not corrected for the slight reduction in internuclear distance due to $\bar{E}_{osc}$.

5. Diatomic Molecular Rotation

A molecule with a permanent dipole moment can resonantly absorb a photon which excites a rotational mode about the center of mass of the molecule. Momentum must be conserved with excitation of a rotational mode. The photon carries $\hbar$ of angular momentum; thus, the rotational angular momentum of the molecule changes by $\hbar$. And, the rotational charge-density function is equivalent to the rigid rotor problem considered in the Rotational Parameters of the Electron (Angular Momentum, Rotational Energy, Moment of Inertia) section of Ref. [5]. The corresponding rigid rotor equation is, $$-\frac{\hbar^2}{2I}\left[\frac{1}{\sin\theta}\frac{\partial}{\partial\theta}\left(\sin\theta\frac{\partial}{\partial\theta}\right)_{r,\phi} + \frac{1}{\sin^2\theta}\left(\frac{\partial^2}{\partial\phi^2}\right)_{r,\theta}\right]Y(\theta,\phi) = E_{rot}Y(\theta,\phi) \quad (277)$$

The energies are given by [41]

$$E_{rotational} = \frac{\hbar^2}{2I}J(J+1) \quad (278)$$

where J is an integer. For Eq. (278), J=0 corresponds to rotation about the z-axis where the internuclear axis is along the y-axis, and J≠0 corresponds to a linear combination of rotations about the z and x-axis. For a diatomic molecule having atoms of masses $m_1$ and $m_2$, the moment of inertia is $$I = \mu r^2 \quad (279)$$

where μ is the reduced mass $$\mu = \frac{m_1 m_2}{m_1 + m_2} \quad (280)$$

and where r is the distance between the centers of the atoms, the internuclear distance.

As given in the Selection Rules section of Ref. [5], the radiation of a multipole of order (l, m) carries $m\hbar$ units of the z component of angular momentum per photon of energy $\hbar\omega$. Thus, the z component of the angular momentum of the corresponding excited rotational state is $$L_z = m\hbar \quad (281)$$

Thus, the selection rule for rotational transitions is $$\Delta J = \pm 1 \quad (282)$$

In addition, the molecule must possess a permanent dipole moment. In the case of absorption of electromagnetic radiation, the molecule goes from a state with a quantum number J to one with a quantum number of J+1. Using Eq. (278), the energy difference is $$\Delta E = E_{J+1} - E_J \quad (283)$$

$$= \frac{\hbar^2}{I}[J+1]$$

5.A. Diatomic Molecular Rotation of Hydrozen-Type Molecular Ions

The reduced mass of hydrogen-type molecular ions and molecules, $\mu_{H_2}$, having two protons is given by Eq. (280) where $m_1 = m_2 = m_p$, and $m_p$ is the mass of the proton.

$$\mu_{H_2} = \frac{m_p m_p}{m_p + m_p} \quad (284)$$

$$= \frac{1}{2}m_p$$

The moment of inertia of hydrogen-type molecular ions is given by substitution of the reduced mass, Eq. (284), for μ of Eq. (279) and substitution of the internuclear distance, two times Eq. (77), for r of Eq. (279).

$$I = m_p \frac{2a_o^2}{p^2} \tag{285}$$

where p is an integer which corresponds to $$H_2^+(1/p), n = \frac{1}{p},$$

the fractional quantum number of the hydrogen-type molecular ion. Using Eqs. (283) and (285), the rotational energy absorbed by a hydrogen-type molecular ion with the transition from the state with the rotational quantum number J to one with the rotational quantum number J+1 is $$\Delta E = E_{J+1} - E_J = \frac{p^2 \hbar^2}{m_p 2 a_H^2}[J+1] \tag{286}$$

$$= p^2[J+1]1.186 \times 10^{-21} J$$

$$= p^2[J+1]0.00740 \text{ eV}$$

From Eq. (286), the calculated energy for the J=0 to J=1 transition of the hydrogen molecular ion $H_2^+$ not including the increase in internuclear due to $\overline{E}_{osc}$ given by Eq. (226) is $$\Delta E = 0.00740 \text{ eV} \tag{287}$$

The experimental value is [19].

$$\Delta E = 0.00739 \text{ eV} \tag{288}$$

5.B. Diatomic Molecular Rotation of Hydrogen-Type Molecules

The moment of inertia of hydrogen-type molecules is given by substitution of the reduced mass, Eq. (284), for μ of Eq. (279) and substitution of the internuclear distance, two times Eq. (165), for r of Eq. (279).

$$I = m_p \frac{a_o^2}{p^2} \tag{289}$$

where p is an integer which corresponds to $H_2(1/p)$, n=1/p, the fractional quantum number of the hydrogen-type molecule. Using Eqs. (283) and (289), the rotational energy absorbed by a hydrogen-type molecule with the transition from the state with the rotational quantum number J to one with the rotational quantum number J+1 is $$\Delta E = E_{J+1} - E_J = \frac{p^2 \hbar^2}{m_p a_o^2}[J+1] \tag{290}$$

$$= p^2[J+1]2.37 \times 10^{-21} J$$

$$= p^2[J+1]0.0148 \text{ eV}$$

From Eq. (290), the calculated energy for the J=0 to J=1 transition of the hydrogen molecule $H_2$ not including the reduction in internuclear due to $\overline{E}_{osc}$ given by Eq. (255) is $$\Delta E = 0.0148 \text{ eV} \tag{291}$$

The experimental value is [19].

$$\Delta E = 0.01509 \text{ eV} \tag{292}$$

6. Nuclear Magnetic Resonance Shift

The proton gyromagnetic ratio, $\gamma_p/2\pi$, is $$\gamma_p/2\pi = 42.57602 \text{ MHz } T^{-1} \tag{293}$$

The NMR frequency, f, is the product of the proton gyromagnetic ratio given by Eq. (293) and the magnetic flux, B.

$$f = \gamma_p/2\pi B = 42.57602 \text{ MHz } T^{-1} B \tag{294}$$

A typical flux for a superconducting NMR magnet is 1.5 T. According to Eq. (294) this corresponds to a radio frequency (RF) of 63.86403 MHz. With a constant magnetic field, the frequency is scanned to yield the spectrum where the scan is typically achieved using a Fourier transform on the free induction decay signal following a radio frequency pulse. Or, in a less common type of NMR spectrometer, the radiofrequency is held constant (e.g. 60 MHz), the applied magnetic field, $H_0$ $$\left(H_0 = \frac{B}{\mu_0}\right),$$

is varied over a small range, and the frequency of energy absorption is recorded at the various values for $H_0$. The spectrum is typically scanned and displayed as a function of increasing $H_0$. The protons that absorb energy at a lower $H_0$ give rise to a downfield absorption peak; whereas, the protons that absorb energy at a higher $H_0$ give rise to an upfield absorption peak. The electrons of the compound of a sample influence the field at the nucleus such that it deviates slightly from the applied value. For the case that the chemical environment has no NMR effect, the value of $H_0$ at resonance with the radiofrequency held constant at 60 MHz is $$\frac{2\pi f}{\mu_0 \gamma_p} = \frac{(2\pi)(60 \text{ MHz})}{\mu_0 42.57602 \text{ MHz } T^{-1}} = H_0 \tag{295}$$

In the case that the chemical environment has a NMR effect, a different value of $H_0$ is required for resonance. This chemical shift is proportional to the electronic magnetic flux change at the nucleus due to the applied field which in the case of each dihydrino molecule is a function of its semimajor and semiminor axes as shown infra.

Consider the application of a z-axis-directed uniform external magnetic flux, $B_z$, to a dihydrino molecule comprising prolate spheroidal electron MOs with two spin-paired electrons. In the case of hydrogen-type molecules, the electronic interaction with the nuclei requires that each nuclear magnetic moment is in the direction of the semiminor axis. Thus, the nuclei are NMR active towards $B_z$ when the orientation of the semimajor axis, a, is along the x-axis, and the semiminor axes, b=c, are along the y-axis and z-axis, respectively. The flux is applied over the time interval $\Delta t = t_i - t_f$ such that the field increases at a rate dB/dt. The electric field, E, along a perpendicular elliptic path of the dihydrino MO at the plane z=0 is given by $$\oint E \cdot ds = \int \frac{dB}{dt} \cdot dA \tag{296}$$

The induced electric field must be constant along the path; otherwise, compensating currents would flow until the electric field is constant. Thus, Eq. (296) becomes $$E = \frac{\int \frac{dB}{dt} \cdot dA}{\oint ds} = \frac{\int \frac{dB}{dt} \cdot dA}{4aE(k)} = \frac{\pi ab \frac{dB}{dt}}{4aE(k)} \quad (297)$$

where E(k) is the elliptic integral given by $$E(k) = \int_0^{\frac{\pi}{2}} \sqrt{1 - k\sin^2\phi} \, d\phi = 1.2375 \quad (298)$$

$$k = e = \frac{\sqrt{a^2 - b^2}}{a} = \frac{\sqrt{2}}{2} \quad (299)$$

the area of an ellipse, A, is $$A = \pi ab \quad (300)$$

the perimeter of an ellipse, s, is $$s = 4aE(k) \quad (301)$$

a is the semimajor axis given by Eq. (164), b is the semiminor axis given by Eq. (166), and e is the eccentricity given by Eq. (167). The acceleration along the path, dv/dt, during the application of the flux is determined by the electric force on the charge density of the electrons:

$$m_e \frac{dv}{dt} = eE = \frac{e\pi ab}{4aE(k)} \frac{dB}{dt} \quad (302)$$

Thus, the relationship between the change in velocity, v, and the change in B is $$dv = \frac{e\pi ab}{4aE(k)m_e} dB \quad (303)$$

Let $\Delta v$ represent the net change in v over the time interval $\Delta t = t_i - t_f$ of the application of the flux. Then, $$\Delta v = \int_{v_0}^{v_0 + \Delta v} dv = \frac{e\pi ab}{4aE(k)m_e} \int_0^B dB = \frac{e\pi abB}{4aE(k)m_e} \quad (304)$$

The average current, I, of a charge moving time harmonically along an ellipse is $$I = ef = \frac{ev}{4aE(k)} \quad (305)$$

where f is the frequency. The corresponding magnetic moment is given by $$m = AI = \pi ab I = \frac{\pi abev}{4aE(k)} \quad (306)$$

Thus, from Eqs. (304) and (306), the change in the magnetic moment, $\Delta m$, due to an applied magnetic flux, B, is [86]

$$\Delta m = -\frac{(e\pi ab)^2 B}{(4aE(k))^2 m_e} \quad (307)$$

Next, the contribution from all plane cross sections of the prolate spheroid MO must be integrated along the z-axis. The spheroidal surface is given by $$\frac{x^2}{a^2} + \frac{y^2}{b^2} + \frac{z^2}{b^2} = 1 \quad (308)$$

The intersection of the plane $z=z'$ ($-b \leq z' \leq b$) with the spheroid determines the curve $$\frac{x^2}{a^2} + \frac{y^2}{b^2} = 1 - \frac{z'^2}{b^2} \text{ or} \quad (309)$$

$$\frac{x^2}{a^2\left(1 - \frac{z'^2}{b^2}\right)} + \frac{y^2}{b^2\left(1 - \frac{z'^2}{b^2}\right)} = 1 \quad (310)$$

Eq. (310) is an ellipse with semimajor axis a' and semiminor axis b' given by $$a' = a\sqrt{1 - \frac{z'^2}{b^2}} \quad (311)$$

$$b' = b\sqrt{1 - \frac{z'^2}{b^2}} \quad (312)$$

The eccentricity, e', is given by $$e' = \frac{\sqrt{a^2\left(1 - \frac{z'^2}{b^2}\right) - b^2\left(1 - \frac{z'^2}{b^2}\right)}}{a\sqrt{1 - \frac{z'^2}{b^2}}} = \frac{\sqrt{a^2 - b^2}}{a} = e \quad (313)$$

where e is given by Eq. (299). The area, A', is given by $$A' = \pi a'b' \quad (314)$$

and the perimeter, s', is given by $$s' = 4a'E(k) = 4aE(k)\sqrt{1 - \frac{z'^2}{b^2}} = s\sqrt{1 - \frac{z'^2}{b^2}} \quad (315)$$

where s is given by Eq. (301). The differential magnetic moment change along the z-axis is $$d\Delta m = -\frac{1}{2b}\frac{(e\pi a'b')^2 B}{(4a'E(k))^2 m_e}dz' \qquad (316)$$

Using Eq. (312) for the parameter b', the change in magnetic moment for the dihydrino molecule is given by the integral over $-b \leq b' \leq b$:

$$\Delta m = -\frac{1}{2b}\int_{-b}^{b}\frac{\left(e\pi a'b\sqrt{1-\frac{z'^2}{b^2}}\right)^2 B}{(4a'E(k))^2 m_e}dz' \qquad (317)$$

$$= -C_1 \frac{1}{m_e}\left(\frac{\pi e}{4E(k)}\right)^2$$

Then, integral to correct for the z-dependence of b' is $$C_1 = \frac{\int_{-b}^{b}(b^2 - z^2)dz}{2b} \qquad (318)$$

$$= \frac{2}{3}b^2$$

$$= \frac{a_0^2}{3p}$$

where the semiminor axis, $$b = \frac{a_0}{p\sqrt{2}},$$

given by Eq. (166) was used.

The change in magnetic moment would be given by the substitution of Eq. (318) into Eq. (317), if the charge density were constant along the path of Eqs. (297) and (305), but it is not. The charge density of the MO in rectangular coordinates (Eq. (51)) is $$\sigma = \frac{e}{4\pi abc}\frac{1}{\sqrt{\frac{x^2}{a^4} + \frac{y^2}{b^4} + \frac{z^2}{c^4}}} \qquad (319)$$

(The mass-density function of an MO is equivalent to its charge-density function where m replaces q of Eq. (51)). The equation of the plane tangent to the ellipsoid at the point $x_0$, $y_0$, $z_0$ is $$X\frac{x_0}{a^2} + Y\frac{y_0}{b^2} + Z\frac{z_0}{c^2} = 1 \qquad (320)$$

where X, Y, Z are running coordinates in the plane. After dividing through by the square root of the sum of the squares of the coefficients of X, Y, and Z, the right member is the distance D from the origin to the tangent plane. That is, $$D = \frac{1}{\sqrt{\frac{x^2}{a^4} + \frac{y^2}{b^4} + \frac{z^2}{c^4}}} \qquad (321)$$

so that $$\sigma = \frac{e}{4\pi abc}D \qquad (322)$$

In other words, the surface density at any point on a the ellipsoidal MO is proportional to the perpendicular distance from the center of the ellipsoid to the plane tangent to the ellipsoid at the point. The charge is thus greater on the more sharply rounded ends farther away from the origin. In order to maintain current continuity, the diamagnetic velocity of Eq. (304) must be a constant along any given path integral corresponding to a constant electric field. Consequently, the charge density must be the minimum value of that given by Eq. (319). The minimum corresponds to y=b and x=z=0 such that the charge density is $$\sigma = \frac{e}{4\pi ab^2}\frac{1}{\sqrt{\frac{0^2}{a^4} + \frac{b^2}{b^4} + \frac{0^2}{b^4}}} \qquad (323)$$

$$= \frac{e}{4\pi ab}$$

The MO is an equipotential surface, and the current must be continuous over the two-dimensional surface. Continuity of the surface current density, K, due to the diamagnetic effect of the applied magnetic field on the MO and the equipotential boundary condition require that the current of each elliptical curve determined by the intersection of the plane z=z' ($-b \leq z' \leq b$) with the spheroid be the same. The charge density is spheroidally symmetrical about the semimajor axis. Thus, λ, the charge density per unit length along each elliptic path cross section of Eq. (310) is given by distributing the surface charge density of Eq. (323) uniformly along the z-axis for $-b \leq z' \leq b$. So, λ(z'=0), the linear charge density λ in the plane z'=0 is $$\lambda(z' = 0) = \frac{\sigma}{\frac{1}{2b}} \qquad (324)$$

$$= \frac{e}{4\pi ab}2b$$

$$= \frac{e}{2\pi a}$$

And, the linear charge density must be equally distributed over each elliptical path cross section corresponding to each plane z=z'. The current is independent of z' when the linear charge density, λ(z'), is normalized for the path length:

$$\lambda(z') = \frac{e}{2\pi a} \frac{4aE(k)}{4a'E(k')} \quad (325)$$

$$= \frac{e}{2\pi a'}$$

where the equality of the eccentricities of each elliptical plane cross section given by Eq. (313) was used. Substitution of Eq. (325) for the corresponding charge density, $$\frac{e}{4a'E(k)},$$

of Eq. (317) and using Eq. (318) gives $$\Delta m = \frac{2}{3} \frac{e^2 b^2 B}{4m_e} \quad (326)$$

$$= \frac{e^2 a_0^2 B}{12 p^2 m_e}$$

The two electrons are spin-paired and the velocities are mirror opposites. Thus, the change in velocity of each electron treated individually (Eq. (10.3) of Ref. [5]) due to the applied field would be equal and opposite. However, as shown in the Three Electron Atom section of Ref. [5], the two paired electrons may be treated as one with twice the mass where $m_e$ is replaced by $2m_e$ in Eq. (326). In this case, the paired electrons spin together about the applied field axis, the z-axis, to cause a reduction in the applied field according to Lenz's law. Thus, from Eq. (326), the change in magnetic moment is given by $$\Delta m = \frac{e^2 a_0^2 B}{24 p^2 m_e} \quad (327)$$

The magnetic moment and magnetic field of the ellipsoidal MO is that corresponding to a Bohr magneton wherein the electrons are spin-paired in molecular hydrogen. The magnetic dipole moment, μ, of a current loop is $$\mu = iA \quad (328)$$

The area of an ellipse is given by Eq. (300). For any elliptic orbital due to a central field, the frequency, f, is $$f = \frac{\frac{L}{m}}{2\pi ab} \quad (329)$$

where L is the angular momentum. The current, i, is $$i = ef \quad (330)$$

$$= \frac{\frac{eL}{m_e}}{2\pi ab}$$

where e is the charge. Substitution of Eqs. (330) and (300) into Eq. (328) where L is the angular momentum of the electron, $\hbar$, gives $$\mu = \frac{e\hbar}{2m_e} \quad (331)$$

$$= \mu_B$$

which is the Bohr magneton.

The magnetic field can be solved as a magnetostatic boundary value problem which is equivalent to that of a uniformly magnetized ellipsoid [73]. The magnetic scalar potential inside the ellipsoidal MO, $\phi^-$, is $$\phi^- = \frac{e\hbar}{2m_e} \times \int_0^\infty \frac{ds}{(s+a^2)R_s} \quad (332)$$

The magnetic scalar potential outside of the MO, $\phi^+$, is $$\phi^+ = \frac{e\hbar}{2m_e} \times \int_\xi^\infty \frac{ds}{(s+a^2)R_s} \quad (333)$$

The magnetic field inside the ellipsoidal MO, $H_x^-$, is $$H_x^- = -\frac{\delta \phi^-}{\delta x} \quad (334)$$

$$= \frac{-e\hbar}{2m_e} \int_0^\infty \frac{ds}{(s+a^2)R_s}$$

The magnetic field inside the ellipsoidal MO. is uniform and parallel to the minor axis. The diamagnetic field has the same dependence wherein the diamagnetic moment replaces the Bohr magneton.

The opposing diamagnetic flux is uniform, parallel, and opposite the applied field as given by Stratton [87]. Specifically, the change in magnetic flux, ΔB, at the nucleus due to the change in magnetic moment, Δm, is $$\Delta B = \mu_0 A_2 \Delta m \quad (335)$$

where $\mu_0$ is the permeability of vacuum, $$A_2 = \int_0^\infty \frac{ds}{(s+b^2)R_s} \quad (336)$$

is an elliptic integral of the second kind given by Whittaker and Watson [88], and $$R_s = (s+b^2)\sqrt{(s+a^2)} \quad (337)$$

Substitution of Eq. (337) into Eq. (336) gives $$A_2 = \int_0^\infty \frac{ds}{(s+b^2)^2(s+a^2)^{1/2}} \quad (338)$$

From integral 154 of Lide [89]:

$$A_2 = -\left\{\frac{1}{a^2-b^2}\frac{\sqrt{s+a^2}}{s+b^2}\right\}_0^\infty - \frac{1}{2}\frac{1}{a^2-b^2}\int_0^\infty \frac{ds}{(s+b^2)\sqrt{s+a^2}} \quad (339)$$

The evaluation at the limits of the first integral is $$-\left\{\frac{1}{a^2-b^2}\frac{\sqrt{s+a^2}}{s+b^2}\right\}_0^\infty = \frac{a}{b^2(a^2-b^2)} \quad (340)$$

From integral 147 of Lide [90], the second integral is:

$$-\frac{1}{2}\frac{1}{a^2-b^2}\int_0^\infty \frac{ds}{(s+b^2)\sqrt{s+a^2}} = \quad (341)$$
$$\left\{\frac{1}{2}\frac{1}{(a^2-b^2)^{3/2}}\ln\frac{\sqrt{s+a^2}+\sqrt{a^2-b^2}}{\sqrt{s+a^2}-\sqrt{a^2-b^2}}\right\}_0^\infty$$

Evaluation at the limits of the second integral gives $$-\frac{1}{2}\frac{1}{(a^2-b^2)^{3/2}}\ln\frac{a+\sqrt{a^2-b^2}}{a-\sqrt{a^2-b^2}} \quad (342)$$

Combining Eq. (340) and Eq. (342) gives $$A_2 = \frac{a}{b^2(a^2-b^2)} - \frac{1}{2}\frac{1}{(a^2-b^2)^{3/2}}\ln\frac{a+\sqrt{a^2-b^2}}{a-\sqrt{a^2-b^2}} \quad (343)$$
$$= \frac{p^3 4}{a_0^3} - \frac{p^3\sqrt{2}}{a_0^3}\ln\frac{\sqrt{2}+1}{\sqrt{2}-1}$$

where the semimajor axis, $$a = \frac{a_0}{p},$$

given by Eq. (164) and the semiminor axis, $$b = \frac{a_0}{p\sqrt{2}},$$

given by Eq. (166) were used.
Substitution of Eq. (327) and Eq. (343) into Eq. (335) gives $$\Delta B = -\mu_0\left(\frac{p^3 4}{a_0^3} - \frac{p^3\sqrt{2}}{a_0^3}\ln\frac{\sqrt{2}+1}{\sqrt{2}-1}\right)\frac{a_0^2 e^2 B}{24 p^2 m_e} \quad (344)$$

Additionally, it is found both theoretically and experimentally that the dimensions, $r^2$, of the molecule corresponding to the area in Eqs. (296) and (306) used to derived Eq. (344) must be replaced by an average, $<r^2>$, that takes into account averaging over the orbits isotopically oriented. The correction of 2/3 is given by Purcell [86]. In the case of hydrogen-type molecules, the electronic interaction with the nuclei require that each nuclear magnetic moment is in the direction of the semiminor axis. But free rotation about each of three axes results in an isotropic averaging of 2/3 where the rotational frequencies of hydrogen-type molecules are much greater than the corresponding NMR frequency (e.g. $10^{12}$ Hz versus $10^8$ Hz). Thus, Eq. (344) gives the absolute upfield chemical shift $$\frac{\Delta B}{B}$$

of $H_2$ relative to a bare proton;

$$\frac{\Delta B}{B} = \frac{\Delta B}{B} \quad (345)$$
$$= -\mu_0\left(\frac{p^3 4}{a_0^3} - \frac{p^3\sqrt{2}}{a_0^3}\ln\frac{\sqrt{2}+1}{\sqrt{2}-1}\right)\frac{a_0^2 e^2}{36 p^2 m_e}$$
$$= -\mu_0\left(4 - \sqrt{2}\ln\frac{\sqrt{2}+1}{\sqrt{2}-1}\right)\frac{pe^2}{36 a_0 m_e}$$
$$= -p 28.01 \text{ ppm}$$

where p=1 for $H_2$.

It follows from Eqs. (164) and (345) that the diamagnetic flux (flux opposite to the applied field) at each nucleus is inversely proportional to the semimajor radius, $$a = \frac{a_o}{p}.$$

For resonance to occur, $\Delta H_0$, the change in applied field from that given by Eq. (295), must compensate by an equal and opposite amount as the field due to the electrons of the dihydrino molecule. According to Eq. (164), the ratio of the semimajor axis of the dihydrino molecule $H_2(1/p)$ to that of the hydrogen molecule $H_2$ is the reciprocal of an integer p. Similarly it is shown in the Hydrino Hydride Ion Nuclear Magnetic Resonance Shift section of Ref. [5] and previously [91], that according to Eq. (7.57) of Ref. [5] the ratio of the radius of the hydrino hydride ion $H^-(1/p)$ to that of the hydride ion $H^-(1/1)$ is the reciprocal of an integer p. It follows from Eqs. (7.59–7.65) of Ref. [5] that compared to a proton with no chemical shift, the ratio of $\Delta H_0$ or resonance of the proton of the hydrino hydride ion $H^-(1/p)$ to that of the hydride ion $H^-(1/1)$ is a positive integer. That is, if only the radius is considered, the absorption peak of the hydrino hydride ion occurs at a value of $\Delta H_0$ that is a multiple of p times the value that is resonant for the hydride ion compared to that of a proton with no shift. However, a hydrino hydride ion is equivalent to the ordinary hydride ion except that it is in a lower energy state. The source current of the state must be considered in addition to the reduced radius.

As shown in the Stability of "Ground" and Hydrino States section of Ref. [5], for the below "ground" (fractional quantum number) energy states of the hydrogen atom, $\sigma_{photon}$, the two-dimensional surface charge due to the "trapped photon" at the electron orbitsphere and phase-locked with the electron orbitsphere current, is given by Eqs. (5.13) and (2.11) of Ref. [5].

$$\sigma_{photon} = \frac{e}{4\pi(r_n)^2}\left[Y_0^0(\theta, \phi) - \frac{1}{n}[Y_0^0(\theta, \phi) + \text{Re}\{Y_\ell^m(\theta, \phi)e^{i\omega_n t}\}]\right]\delta(r - r_n) \quad (346)$$

$$n = \frac{1}{p} = 1, \frac{1}{2}, \frac{1}{3}, \frac{1}{4}, \ldots,$$

And, $\sigma_{electron}$, the two-dimensional surface charge of the electron orbitsphere is $$\sigma_{electron} = \frac{-e}{4\pi(r_n)^2}[Y_0^0(\theta, \phi) + \text{Re}\{Y_\ell^m(\theta, \phi)e^{i\omega_n t}\}]\delta(r - r_n) \quad (347)$$

The superposition of $\sigma_{photon}$ (Eq. (346)) and $\sigma_{electron}$, (Eq. (347)) where the spherical harmonic functions satisfy the conditions given in the Angular Function section of Ref. [5] is $$\sigma_{photon} + \sigma_{electron} = \frac{-e}{4\pi(r_n)^2}\left[\frac{1}{n}Y_0^0(\theta, \phi) + \left(1 + \frac{1}{n}\right)\text{Re}\{Y_\ell^m(\theta, \phi)e^{i\omega_n t}\}\right]\delta(r - r_n) \quad (348)$$

$$n = \frac{1}{p} = 1, \frac{1}{2}, \frac{1}{3}, \frac{1}{4}, \ldots,$$

The ratio of the total charge distributed over the surface at the radius of the hydrino hydride ion H⁻(1/p) to that of the hydride ion H⁻(1/1) is an integer p, and the corresponding total source current of the hydrino hydride ion is equivalent to an integer p times that of an electron. The "trapped photon" obeys the phase-matching condition given in Excited States of the One-Electron Atom (Quantization) section of Ref [5], but does not interact with the applied flux directly. Only each electron does; thus, $\Delta v$ of Eq. (304) must be corrected by a factor of 1/p corresponding to the normalization of the electron source current according to the invariance of charge under Gauss' Integral Law. As also shown by Eqs. (7.8–7.14) and (7.57) of Ref. [5], the "trapped photon" gives rise to a correction to the change in magnetic moment due to the interaction of each electron with the applied flux. The correction factor of 1/p consequently cancels the NMR effect of the reduced radius which is consistent with general observations on diamagnetism [92]. It follows that the same result applies in the case of Eq. (345) for $H_2$(1/p) wherein the coordinates are elliptic rather than spherical.

The cancellation of the chemical shift due to the reduced radius or the reduced semiminor and semimajor axes in the case of H⁻(1/p) and $H_2$(1/p), respectively, by the corresponding source current is exact except for an additional relativistic effect. The relativistic effect for H⁻(1/p) arises due to the interaction of the currents corresponding to the angular momenta of the "trapped photon" and the electrons and is analogous to that of the fine structure of the hydrogen atom involving the $^2P_{3/2}$–$^2P_{1/2}$ transition. The derivation follows that of the fine structure given in the Spin-Orbital Coupling section of Ref. [5].

$$\frac{e}{m_e}$$

of the electron, the electron angular momentum of $\hbar$, and the electron magnetic momentum of $\mu_B$ are invariant for any electronic state. The same applies for the paired electrons of hydrino hydride ions. The condition that flux must be linked by the electron in units of the magnetic flux quantum in order to conserve the invariant electron angular momentum of $\hbar$ gives the additional chemical shift due to relativistic effects. Using Eqs. (2.85–2.86) of Ref. [5], Eq. (2.92) [5] may be written as $$E_{s/o} = \frac{\alpha\pi\mu_0 e^2 \hbar^2}{m_e^2 r^3}\sqrt{\frac{3}{4}} \quad (349)$$

$$= \alpha 2\pi 2 \frac{e\hbar}{2m_e} \frac{\mu_0 e\hbar}{2m_e a_0^3}\sqrt{\frac{3}{4}}$$

$$= \alpha 2\pi 2 \mu_B B$$

From Eq. (349) and Eq. (1.194) of Ref. [5], the relativistic stored magnetic energy contributes a factor of $\alpha 2\pi$ In spherical coordinates, the relativistic change in flux, $\Delta B_{SR}$, may be calculated using Eq. (7.64) of Ref. [5] and the relativistic factor of $\gamma_{SR} = 2\pi\alpha$ which is the same as that given by Eq. (1.218) of Ref. [5]:

$$\Delta B_{SR} = -\gamma_{SR}\mu_0 \frac{\Delta m}{r_n^3}(i_r\cos\theta - i_\theta\sin\theta) \quad (350)$$

$$= -2\pi\alpha\mu_0 \frac{\Delta m}{r_n^3}(i_r\cos\theta - i_\theta\sin\theta)$$

for $r < r_n$.

The stored magnetic energy term of the electron g factor of each electron of a dihydrino molecule is the same as that of a hydrogen atom since $$\frac{e}{m_e}$$

is invariant and the invariant angular momentum and magnetic moment of the former are also $\hbar$ and $\mu_B$, respectively, as given supra. Thus, the corresponding correction in elliptic coordinates follows from Eq. (2.92) of Ref. [5] wherein the result of the length contraction for the circular path in spherical coordinates is replaced by that of the elliptic path.

The only position on the elliptical path at which the current is perpendicular to the radial vector defined by the central force of the protons is at the semimajor axis. It was shown in the Special Relativistic Correction to the Ionization Energies section of Ref. [5] that when the condition that the electron's motion is tangential to the radius is met, the radius is Lorentzian invariant. That is, for the case that k is the lightlike $k^0$, with $k=\omega_n/c$, a is invariant. In the case of a spherically symmetrical MO such as the case of the hydrogen atom, it was also shown that this condition determines that the electron's angular momentum of $\hbar$, $$\frac{e}{m_e}$$

of Eq. (1.99) of Ref. [5], and the electron's magnetic moment of a Bohr magneton, $\mu_B$, are invariant. The effect of the relativistic length contraction and time dilation for constant spherical motion is a change in the angle of motion with a corresponding decrease in the electron wavelength. The angular motion becomes projected onto the radial axis which contracts, and the extent of the decrease in the electron wavelength and radius due to the electron motion in the laboratory inertial frame are given by $$\lambda = 2\pi r' \sqrt{1-\left(\frac{v}{c}\right)^2} \sin\left[\frac{\pi}{2}\left(1-\left(\frac{v}{c}\right)^2\right)^{3/2}\right] + r'\cos\left[\frac{\pi}{2}\left(1-\left(\frac{v}{c}\right)^2\right)^{3/2}\right] \quad (351)$$

and $$r = r'\left[\sqrt{1-\left(\frac{v}{c}\right)^2} \sin\left[\frac{\pi}{2}\left(1-\left(\frac{v}{c}\right)^2\right)^{3/2}\right] + \frac{1}{2\pi}\cos\left[\frac{\pi}{2}\left(1-\left(\frac{v}{c}\right)^2\right)^{3/2}\right]\right] \quad (352)$$

respectively. Then, the relativist factor $\gamma^*$ is $$\gamma^* = \frac{2\pi}{2\pi\sqrt{1-\left(\frac{v}{c}\right)^2}\sin\left[\frac{\pi}{2}\left(1-\left(\frac{v}{c}\right)^2\right)^{3/2}\right]+\cos\left[\frac{\pi}{2}\left(1-\left(\frac{v}{c}\right)^2\right)^{3/2}\right]} \quad (353)$$

where the velocity is given by Eq. (1.56) of Ref. [5] with the radius given by Eq. (1.223) [5].

Each point or coordinate position on the continuous two-dimensional electron MO of the dihydrino molecule defines an infinitesimal mass-density element which moves along a geodesic orbit of a spheroidal MO in such a way that its eccentric angle, $\theta$, changes at a constant rate. That is $\theta=\omega t$ at time t where $\omega$ is a constant, and $$r(t)=ia\cos\omega t+jb\sin\omega t \quad (354)$$

is the parametric equation of the ellipse of the geodesic. Next, special relativistic effects on distance and time are considered. The parametric radius, r(t), is a minimum at the position of the semiminor axis of length b, and the motion is transverse to the radial vector. Since the angular momentum of $\hbar$ is constant, the electron wavelength without relativistic correction is given by $$2\pi b = \lambda = \frac{h}{mv} \quad (355)$$

such that the angular momentum, L, is given by $$L=r\times mv=bmv=\hbar \quad (356)$$

The nonradiation and the $\hbar$, $$\frac{e}{m_e},$$

and $\mu_B$ invariance conditions require that the angular frequencies, $\omega_s$ and $\omega_e$, for spherical and ellipsoidal motion, respectively, are $$\omega_s = \frac{\hbar}{m_e r^2} = \frac{\pi L}{\frac{m_e}{A}} \text{ and} \quad (357)$$

$$\omega_e = \frac{\pi\hbar}{m_e A} = \frac{\hbar}{m_e ab} \quad (358)$$

where A is the area of the closed geodesic orbit, the area of an ellipse given by Eq. (300). Since the angular frequency $\omega_e$ has the form as $\omega_s$, the time dilation corrections are equivalent, where the correction for $\omega_s$ is given in the Special Relativistic Correction to the Ionization Energies section of Ref. [5]. Since the semimajor axis, a, is invariant, but b undergoes length contraction, the relationship between the velocity and the electron wavelength at the semiminor axis from Eq. (351) and Eq. (355) is $$\lambda = 2\pi b\sqrt{1-\left(\frac{v}{c}\right)^2}\sin\left[\frac{\pi}{2}\left(1-\left(\frac{v}{c}\right)^2\right)^{3/2}\right]+a\cos\left[\frac{\pi}{2}\left(1-\left(\frac{v}{c}\right)^2\right)^{3/2}\right] \quad (359)$$

where $\lambda\rightarrow a$ as $v\rightarrow c$ replaces the spherical coordinate result of $\lambda\rightarrow r'$ as $v\rightarrow c$. Thus, in the electron frame at rest v=0, and, Eq. (359) becomes $$\lambda'=2\pi b \quad (360)$$

In the laboratory inertial frame for the case that v=c in Eq. (359), $\lambda$ is $$\lambda=a \quad (361)$$

Thus, using Eqs. (360) and (361), the relativistic relativist factor, $\gamma^*$, is $$\gamma^* = \frac{\lambda}{\lambda'} = \frac{a}{2\pi b} \quad (362)$$

From Eqs. (351–353) and Eq. (362), the relativistic diamagnetic effect of the inverse integer radius of $H_2(1/p)$ compared to $H_2$, each with ellipsoidal MOs, is equivalent to the ratio of the semiminor and semimajor axes times the correction for the spherical orbital case given in Eq. (350). From the mass (Eq. (2.91) of Ref. [5]) and radius corrections (Eq. (2.89) [5]) in Eq. (2.92) [5], the relativistic stored magnetic energy contributes a factor $\gamma_{SR}$ of $$\gamma_{SR} = 2\pi\alpha\left(\frac{b}{a}\right)^2 = \pi\alpha \tag{363}$$

Thus, from Eqs. (335), (350), and (363), the relativistic change in flux, $\Delta B_{SR}$, for the dihydrino molecule $H_2(1/p)$ is $$\Delta B_{SR} = -\gamma_{SR}\mu_0 A_2 \Delta m = -\pi\alpha\mu_0 A_2 \Delta m \tag{364}$$

Thus, using Eq. (345) and Eq. (364), the upfield chemical shift, $$\frac{\Delta B_{SR}}{B},$$

due to the relativistic effect of the molecule $H_2(1/p)$ corresponding to the lower-energy state with principal quantum energy state p is given by $$\frac{\Delta B_{SR}}{B} = -\mu_0\pi\alpha\left(4 - \sqrt{2}\ln\frac{\sqrt{2}+1}{\sqrt{2}-1}\right)\frac{pe^2}{36a_0 m_e} \tag{365}$$

The total shift, $$\frac{\Delta B_T}{B},$$

for $H_2(1/p)$ is given by the sum of that of $H_2$ given by Eq. (345) with p=1 plus that given by Eq. (365):

$$\frac{\Delta B_T}{B} = -\mu_0\left(4 - \sqrt{2}\ln\frac{\sqrt{2}+1}{\sqrt{2}-1}\right)\frac{e^2}{36a_0 m_e}(1+\pi\alpha p) \tag{366}$$

$$\frac{\Delta B_T}{B} = -(28.01 + 0.64p)\text{ppm} \tag{367}$$

where p=integer >1.

$H_2$ has been characterized by gas phase $^1$H NMR. The experimental absolute resonance shift of gas-phase TMS relative to the proton's gyromagnetic frequency is −28.5 ppm [83]. $H_2$ was observed at 0.48 ppm compared to gas phase TMS set at 0.00 ppm [84]. Thus, the corresponding absolute $H_2$ gas-phase resonance shift of −28.0 ppm (−28.5+ 0.48) ppm was in excellent agreement with the predicted absolute gas-phase shift of −28.01 ppm given by Eq. (345).

7. The Dihydrino Molecular Ion $H_2[2c'=a_o]^+$

7.A. Force Balance of the Dihydrino Molecular Ion

Force balance between the electric and centrifugal forces of $H_2^+(½)$ is given by Eq. (67) where p=2

$$\frac{\hbar^2}{m_e a^2 b^2}2ab^2 X = \frac{2e^2}{4\pi\varepsilon_o}X \tag{368}$$

which has the parametric solution given by Eq. (61) when $$a = a_o \tag{369}$$

The semimajor axis, a, is also given by Eq. (68) where p=2. The internuclear distance, 2c', which is the distance between the foci is given by Eq. (77) where p=2.

$$2c' = a_o \tag{370}$$

The semiminor axis is given by Eq. (79) where p=2.

$$b = \frac{\sqrt{3}}{2}a_o \tag{371}$$

The eccentricity, e, is given by Eq. (81).

$$e = \frac{1}{2} \tag{372}$$

7.B. Energies of the Dihydrino Molecular Ion

The potential energy, $V_e$, of the electron MO in the field of magnitude twice that of the protons at the foci ($\xi=0$) is given by Eq. (69) where p=2

$$V_e = \frac{-8e^2}{8\pi\varepsilon_o\sqrt{a^2-b^2}}\ln\frac{a+\sqrt{a^2-b^2}}{a-\sqrt{a^2-b^2}} \tag{373}$$

The potential energy, $V_p$, due to proton-proton repulsion in the field of magnitude twice that of the protons at the foci ($\xi=0$) is given by Eq. (82) where p=2

$$V_p = \frac{2e^2}{8\pi\varepsilon_o\sqrt{a^2-b^2}} \tag{374}$$

The kinetic energy, T, of the electron MO is given by Eq. (71) where p=2

$$T = \frac{2\hbar^2}{m_e a\sqrt{a^2-b^2}}\ln\frac{a+\sqrt{a^2-b^2}}{a-\sqrt{a^2-b^2}} \tag{375}$$

Substitution of a and b given by Eqs. (369) and (371), respectively, into Eqs. (373–375) and using Eqs. (153–155) with p=2 gives $$V_e = \frac{-16e^2}{8\pi\varepsilon_o a_o}\ln 3 = -239.16 \text{ eV} \tag{376}$$

$$V_p = \frac{4e^2}{8\pi\varepsilon_o a_o} = 54.42 \text{ eV} \tag{377}$$

$$T = \frac{8e^2}{8\pi\varepsilon_o a_o}\ln 3 = 119.58 \text{ eV} \tag{378}$$

$$E_T = V_e + V_p + T + \overline{E}_{osc} \tag{379}$$

-continued $$E_T = -2^2 \left\{ \left[ \frac{\frac{e^2}{8\pi\varepsilon_o a_H}(4\ln 3 - 1 - 2\ln 3)}{1 + 2\sqrt{\frac{2\hbar\sqrt{\frac{2e^2}{4\pi\varepsilon_o(2a_H)^3}}}{m_e c^2}}} \right] - \frac{1}{2}\hbar\sqrt{\frac{k}{\mu}} \right\} \quad (380)$$

$$= -2^2(16.13392 \text{ eV}) - 2^3(0.118755 \text{ eV})$$

$$= -65.49 \text{ eV}$$

where Eqs. (376–78) are equivalent to Eqs. (84–86) with p=2. The bond dissociation energy, $E_D$, given by Eq. (160) with p=2 is the difference between the total energy of the corresponding hydrino atom and $E_T$ given by Eq. (380):

$$E_D = E_T(H(1/p)) - E_T(H_2^+(1/p)) \quad (381)$$

$$= 2^2(2.535 \text{ eV}) + 2^3(0.118755 \text{ eV})$$

$$= 11.09 \text{ eV}$$

7.C. Vibration of the Dihydrino Molecular Ion

It can be shown that a perturbation of the orbit determined by an inverse-squared force results in simple harmonic oscillatory motion of the orbit [75]. The resonant vibrational frequency for $H_2^+(\frac{1}{2})$ from Eq. (122) is $$\omega(0) = 2^2 \sqrt{\frac{165.51 \text{ Nm}^{-1}}{\mu}} = 1.78 \times 10^{15} \text{ radians/s} \quad (382)$$

wherein p=2. The spring constant, k(0), for $H_2^+(\frac{1}{2})$ from Eq. (124) is $$k(0) = 2^4 165.51 \text{ Nm}^{-1} = 2648 \text{ Nm}^{-1} \quad (383)$$

The amplitude of oscillation from Eq. (126) is $$A(0) = \frac{\sqrt{\hbar}}{2^{3/2}(2^4(165.51)\text{Nm}^{-1}\mu)^{1/4}} \quad (384)$$

$$= \frac{5.952 \times 10^{-12} \text{ m}}{2}$$

$$= \frac{0.1125 a_o}{2}$$

The vibrational energy, $E_{vib}(1)$, for the $\upsilon=1 \rightarrow \upsilon=0$ transition given by Eq. (128) is $$E_{vib}(1) = 2^2(0.270 \text{ eV}) = 1.08 \text{ eV} \quad (385)$$

8. The Dihydrino Molecule $$H_2\left[2c' = \frac{a_0}{\sqrt{2}}\right]$$

8.A. Force Balance of the Dihydrino Molecule

The force balance equation for the dihydrino molecule $H_2(\frac{1}{2})$ is given by Eq. (162) where p=2

$$\frac{\hbar^2}{m_e a^2 b^2} 2ab^2 X = \frac{2e^2}{4\pi\varepsilon_o} X + \frac{\hbar^2}{2m_e a^2 b^2} 2b^2 X \quad (386)$$

which has the parametric solution given by Eq. (61) when $$a = \frac{a_o}{2} \quad (387)$$

The semimajor axis, a, is also given by Eq. (164) where p=2. The internuclear distance, 2c', which is the distance between the foci is given by Eq. (165) where p=2.

$$2c' = \frac{1}{\sqrt{2}} a_o \quad (388)$$

The semiminor axis is given by Eq. (166) where p 2.

$$b = c = \frac{1}{2\sqrt{2}} a_o \quad (389)$$

The eccentricity, e, is given by Eq. (167).

$$e = \frac{1}{\sqrt{2}} \quad (390)$$

8.B. Energies of the Dihydrino Molecule

The energies of the dihydrino molecule $H_2(\frac{1}{2})$ are given by Eqs. (168–171) and Eqs. (200–202) with p=2

$$V_e = \frac{-4e^2}{8\pi\varepsilon_o \sqrt{a^2 - b^2}} \ln\frac{a + \sqrt{a^2 - b^2}}{a - \sqrt{a^2 - b^2}} = -271.34 \text{ eV} \quad (391)$$

$$V_p = \frac{2}{8\pi\varepsilon_o} \frac{e^2}{\sqrt{a^2 - b^2}} = 76.97 \text{ eV} \quad (392)$$

$$T = \frac{\hbar^2}{2m_e a\sqrt{a^2 - b^2}} \ln\frac{a + \sqrt{a^2 - b^2}}{a - \sqrt{a^2 - b^2}} = 135.67 \text{ eV} \quad (393)$$

The energy, $V_m$, of the magnetic force is $$V_m = \frac{-\hbar^2}{4m_e a\sqrt{a^2 - b^2}} \ln\frac{a + \sqrt{a^2 - b^2}}{a - \sqrt{a^2 - b^2}} = -67.84 \text{ eV} \quad (394)$$

$$E_T = V_e + T + V_m + V_p + \overline{E}_{osc} \quad (395)$$

$$E_T = -2^2 \left\{ \frac{\frac{e^2}{8\pi\varepsilon_o a_0}\left[\left(2\sqrt{2} - \sqrt{2} + \frac{\sqrt{2}}{2}\right)\ln\frac{\sqrt{2}+1}{\sqrt{2}-1} - \sqrt{2}\right]}{\left[1 + 2\sqrt{\frac{2\hbar\sqrt{\frac{e^2}{4\pi\varepsilon_o a_0^3}}{m_e}}{m_e c^2}}\right]} - \frac{1}{2}\hbar\sqrt{\frac{k}{\mu}} \right\} \quad (396)$$

$$= -2^2(31.351 \text{ eV}) - 2^3(0.326469 \text{ eV})$$

$$= -128.02 \text{ eV}$$

where Eqs. (391–393) are equivalent to Eqs. (168–171) with p=2. The bond dissociation energy, $E_D$, given by Eq. (213) with p=2 is the difference between the total energy of the corresponding hydrino atoms and $E_T$ given by Eq. (396).

$$E_D = E_T(2H(1/p)) - E_T(H_2(1/p)) \quad (397)$$

$$= 2^2(4.151 \text{ eV}) + 2^3(0.326469 \text{ eV})$$

$$= 19.22 \text{ eV}$$

8.C. Vibration of the Dihydrino Molecule

It can be shown that a perturbation of the orbit determined by an inverse-squared force results in simple harmonic oscillatory motion of the orbit [75]. The resonant vibrational frequency for the $H_2(\frac{1}{2})$ from Eq. (178) is $$\omega(0) = 2^2\sqrt{\frac{k}{\mu}} = 2^2\sqrt{\frac{621.98 \text{ Nm}^{-1}}{\mu}} \, 3.45 \times 10^{15} \text{ radians/s} \quad (398)$$

wherein p=2. The spring constant, k(0), for $H_2(\frac{1}{2})$ from Eq. (180) is $$k(0) = 2^4 621.98 \text{ Nm}^{-1} = 9952 \text{ Nm}^{-1} \quad (399)$$

The amplitude of oscillation from Eq. (182) is $$A(0) = \frac{\sqrt{\hbar}}{2^{3/2}(2^4(621.98) \text{ Nm}^{-1}\mu)^{1/4}} \quad (400)$$

$$= \frac{4.275 \times 10^{-12} \text{ m}}{2}$$

$$= \frac{0.08079 a_o}{2}$$

The vibrational energy, $E_{vib}(1)$, of $H_2(\frac{1}{2})$ from Eq. (184) is $$E_{vib}(1) = 2^2(0.517) \text{ eV} = 2.07 \text{ eV} \quad (401)$$

9. Data Supporting H(1/p), H⁻(1/p), $H_2^+$(1/p), and $H_2$(1/p)

Novel emission lines with energies of q·13.6 eV where q=1,2,3,4,6,7,8,9, or 11 were previously observed by extreme ultraviolet (EUV) spectroscopy recorded on microwave discharges of helium with 2% hydrogen [53–56, 68]. These lines matched H(1/p), fractional Rydberg states of atomic hydrogen wherein $$n = \frac{1}{2}, \frac{1}{3}, \frac{1}{4}, \dots, \frac{1}{p};$$

($p \leq 137$ is an integer) replaces the well known parameter n=integer in the Rydberg equation for hydrogen excited states. A series of unique EUV lines assigned to $H_2(\frac{1}{2})$ were observed as well [54]. Evidence supports that these states are formed by a resonant nonradiative energy transfer to He⁺ acting as a catalyst. Ar⁺ also serves as a catalyst to form H(1/p); whereas, krypton, xenon, and their ions serve as controls. H(1/p) may react with a proton and two H(1/p) may react to form $H_2(1/p)^+$ and $H_2(1/p)$, respectively, that have vibrational and rotational energies that are p² times those of the species comprising uncatalyzed atomic hydrogen. A series of over twenty peaks in the 10–65 nm region emitted from low-pressure helium-hydrogen (90/10%) and argon-hydrogen (90/10%) microwave plasmas matched the energy spacing of 2² times the transition-state vibrational energy of $H_2^+$ with the series ending on the bond energy of $H_2(\frac{1}{4})^+$ [57–58, 67]. Rotational lines were observed in the 145–300 nm region from atmospheric pressure electron-beam excited argon-hydrogen plasmas. The unprecedented energy spacing of 4² times that of hydrogen established the internuclear distance as ¼ that of $H_2$ and identified $H_2$ (¼) [67].

$H_2(1/p)$ gas was isolated by liquefaction at liquid nitrogen temperature and by decomposition of compounds found to contain the corresponding hydride ions H⁻(1/p) [67]. The $H_2(1/p)$ gas was dissolved in $CDCl_3$ and characterized by ¹H NMR. The absolute $H_2$ gas-phase shift was used to determine the solvent shift for $H_2$ dissolved in $CDCl_3$. The correction for the solvent shift was then be applied to other peaks to determine the gas-phase absolute shifts to compare to Eq. (367). The shifts of all of the peaks were relative to liquid-phase TMS which has an experimental absolute resonance shift of −31.5 ppm relative to the proton's gyromagnetic frequency [93–94]. Thus, the experimental shift of $H_2$ in $CDCl_3$ of 4.63 ppm relative to liquid-phase TMS corresponds to an absolute resonance shift of −26.87 ppm (−31.5 ppm+4.63 ppm). Using the absolute $H_2$ gas-phase resonance shift of −28.0 ppm corresponding to 3.5 ppm (−28.0 ppm−31.5 ppm) relative to liquid TMS, the $CDCl_3$ solvent effect is 1.13 ppm (4.63 ppm−3.5 ppm) which is comparable to that of hydrocarbons [95]. The solvent shift of $H_2(1/p)$ was assumed to be the same as the down-field shift for $H_2$; thus, novel peaks were corrected by −1.13 ppm relative to a proton's gyromagnetic frequency to give the absolute gas-phase shifts.

Singlet peaks upfield of $H_2$ with a predicted integer spacing of 0.64 ppm were observed at 3.47, 3.02, 2.18, 1.25, 0.85, 0.21, and −1.8 ppm relative to TMS corresponding to solvent-corrected absolute resonance shifts of −29.16, −29.61, −30.45, −31.38, −31.78, −32.42, and −34.43 ppm, respectively. Using Eq. (367), the data indicates that p=2, 3, 4, 5, 6, 7, and 10, respectively, which matches the series $H_2(\frac{1}{2})$, $H_2(\frac{1}{3})$, $H_2(\frac{1}{4})$, $H_2(\frac{1}{5})$, $H_2(\frac{1}{6})$, $H_2(\frac{1}{7})$, and $H_2(\frac{1}{10})$ [67]. The ¹H NMR spectra of gases from the thermal decomposition of KH*I matched those of LN-condensable hydrogen. This provided strong support that compounds such as KH*I contain hydride ions H⁻(1/p) in the same fractional quantum state p as the corresponding observed $H_2(1/p)$. Observational agreement with predicted positions of upfield-shifted ¹H MAS NMR peaks (Eq. (31)) of Ref.

[67]) of the compounds [69–70, 91, 96], catalyst reactions [59, 65, 91, 97], and spectroscopic data [59] supports this conclusion.

Excess power was absolutely measured from the helium-hydrogen plasma [67–68]. For an input of 41.9 W, the total plasma power of the helium-hydrogen plasma measured by water bath calorimetry was 62.1 W corresponding to 20.2 W of excess power in 3 cm$^3$ plasma volume. The excess power density and energy balance were high, 6.7 W/cm$^3$ and $-5.4 \times 10^4$ kJ/mole H$_2$(280 eV/H atom), respectively. On this basis, and the results of the characterization of the hydride compounds and H$_2$(1/p) gas, possibilities for advanced technologies exist. In addition to power applications, battery and propellant reactions were proposed that may be transformational [67]. The application of the observed excited vibration-rotational levels of H$_2$(¼) as the basis of a UV or EUV laser that could significantly advance photolithography was also discussed previously [67].

10. Systems

Embodiments of the system for performing computing and rendering of the nature of the chemical bond using the physical solutions may comprise a general purpose computer. Such a general purpose computer may have any number of basic configurations. For example, such a general purpose computer may comprise a central processing unit (CPU), one or more specialized processors, system memory, a mass storage device such as a magnetic disk, an optical disk, or other storage device, an input means such as a keyboard or mouse, a display device, and a printer or other output device. A system implementing the present invention can also comprise a special purpose computer or other hardware system and all should be included within its scope.

The display can be static or dynamic such that vibration and rotation can be displayed in an embodiment. The displayed information is useful to anticipate reactivity and physical properties. The insight into the nature of the chemical bond can permit the solution and display of other molecules and provide utility to anticipate their reactivity and physical properties.

Embodiments within the scope of the present invention also include computer program products comprising computer readable medium having embodied therein program code means. Such computer readable media can be any available media which can be accessed by a general purpose or special purpose computer. By way of example, and not limitation, such computer readable media can comprise RAM, ROM, EPROM, CD ROM, DVD or other optical disk storage, magnetic disk storage or other magnetic storage devices, or any other medium which can embody the desired program code means and which can be accessed by a general purpose or special purpose computer. Combinations of the above should also be included within the scope of computer readable media. Program code means comprises, for example, executable instructions and data which cause a general purpose computer or special purpose computer to perform a certain function of a group of functions.

A specific example of the rendering of molecular hydrogen using Mathematica and computed on a PC is shown in FIG. 1A. The algorithm used was ParametricPlot3D[{2*Sqrt[1−z*z]*Cos[u],Sqrt[(1−z*z)]*Sin[u],z},{u,0,2*Pi}, {z,−1, 0.9999}]. The rendering can be viewed from different perspectives. A specific example of the rendering of molecular hydrogen using Mathematica and computed on a PC from different perspectives was achieved with algorithms such as Show[Out[1], ViewPoint->{0,−1,1}] and Show[Out[1], ViewPoint->{−1,1,1}]

In general, the algorithms for viewing from different perspectives comprises
Show[Out[1], ViewPoint->{x,y,z}] where x, y, and z are Cartesian coordinates.

The present invention may be embodied in other specific forms without departing from the spirit or essential attributes thereof and, accordingly, reference should be made to the appended claims, rather than to the foregoing specification, as indicating the scope of the invention.

REFERENCES

1. R. Mills, "The Hydrogen Atom Revisited," Int. J. of Hydrogen Energy, Vol. 25, Issue 12, December, (2000), pp. 1171–1183.
2. R. Mills, The Nature of Free Electrons in Superfluid Helium—a Test of Quantum Mechanics and a Basis to Review its Foundations and Make a Comparison to Classical Theory, Int. J. Hydrogen Energy, Vol. 26, No. 10, (2001), pp. 1059–1096.
3. R. L. Mills, "Classical Quantum Mechanics," Physics Essays, in press, http://www.blacklightpower.com/pdf/CQMTheoryPaperTablesand%20Figures080403.pdf.
4. R. L. Mills, The Fallacy of Feynman's Argument on the Stability of the Hydrogen Atom According to Quantum Mechanics, Foundations of Physics, submitted, http://www.blacklightpower.com/pdf/Feynman%27s%20Argument%20Spec%20UPDATE%20091003.pdf.
5. R. Mills, *The Grand Unified Theory of Classical Quantum Mechanics*, September 2001 Edition, BlackLight Power, Inc., Cranbury, N.J., Distributed by Amazon.com; July 2003 Edition posted at http://www.blacklightpower.com.
6. F. Laloë, Do we really understand quantum mechanics? Strange correlations, paradoxes, and theorems, Am. J. Phys. 69 (6), June 2001, 655–701.
7. D. A. McQuarrie, *Quantum Chemistry*, University Science Books, Mill Valley, Calif., (1983), pp. 160–183.
8. M. Karplus, R. N. Porter, *Atoms and Molecules an Introduction for Students of Physical Chemistry*, The Benjamin/Cummings Publishing Company, Menlo Park, Calif., (1970), pp. 447–484.
9. L. J. Butler, "Chemical reaction dynamics beyond the Born-Oppenheimer approximation," Annu. Rev. Chem., Vol. 49, (1998), pp. 125–171.
10. D. A. McQuarrie, *Quantum Chemistry*, University Science Books, Mill Valley, Calif., (1983), pp. 343–422.
11. P. Pearle, Foundations of Physics, "Absence of radiationless motions of relativistically rigid classical electron," Vol. 7, Nos. 11/12, (1977), pp. 931–945.
12. V. F. Weisskopf, Reviews of Modern Physics, Vol. 21, No. 2, (1949), pp. 305–315.
13. K. R. Lykke, K. K. Murray, W. C. Lineberger, "Threshold photodetachment of H−," Phys. Rev. A, Vol. 43, No. 11, (1991), pp. 6104–6107.
14. C. A. Coulson, Trans. Far. Soc., Vol. 33, (1937), p. 1479.
15. W. Kolos and L. Wolniewicz, J. Chem. Phys., Vol. 41, (1964), p. 3663; Vol. 49, (1968), p. 404.
16. H. M. James, A. S. Coolidge, J. Chem. Phys., Vol. 1, (1933), p. 825.
17. S. C. Wang, Phys. Rev., Vol. 31, (1928), p. 579.
18. E. Purcell, *Electricity and Magnetism*, McGraw-Hill, New York, (1985), pp. 29–31.
19. P. W. Atkins, *Physical Chemistry*, Second Edition, W. H. Freeman, San Francisco, (1982), p. 589.

20. H. Beutler, Z. Physical Chem., "Die dissoziationswarme des wasserstoffmolekuls $H_2$, aus einem neuen ultravioletten resonanzbandenzug bestimmt," Vol. 27B, (1934), pp. 287–302.
21. G. Herzberg, L. L. Howe, "The Lyman bands of molecular hydrogen," Can. J. Phys., Vol. 37, (1959), pp. 636–659.
22. S. Durr, T. Norm, G. Rempe, Nature, September 3, (1998), Vol. 395, pp. 33–37.
23. Science News, "Wave or particle? Heisenberg, take a hike!" Vol. 154, Sep. 5, 1998.
24. R. Mills, *The Grand Unified Theory of Classical Quantum Mechanics*, September 2001 Edition, BlackLight Power, Inc., Cranbury, N.J., Distributed by Amazon.com; July 2003 Edition posted at http://www.blacklightpower.com/bookdownload.shtml, Foreword and Chp 37.
25. D. A. McQuarrie, *Quantum Chemistry*, University Science Books, Mill Valley, Calif., (1983), pp. 135–140.
26. R. Wynar, R. S. Freeland, D. J. Han, C. Ryu, and D. J. Heinzen, "Molecules in a Bose-Einstein Condensate," Science, Vol. 287, February, 11, (2000), pp. 1016–1019.
27. M. Mizushima, *Quantum Mechanics of Atomic Spectra and Atomic Structure*, W. A. Benjamin, Inc., New York, (1970), p. 17.
28. H. A. Haus, "On the radiation from point charges," American Journal of Physics, 54, (1986), pp. 1126–1129.
29. L. A. Curtiss, K. Raghavachari, "Gaussian-3 and related methods for accurate thermochemistry," Theor. Chem. Acc., Vol. 108, (2002), pp. 61–70.
30. L. A. Curtiss, K. Raghavachari, P. C. Redfern, V. Rassolov, J. A. Pople, "Gaussian-3 (G3) theory for molecules containing first and second-row atoms," J. Chem. Phys., Vol. 109, No. 18, (1998), pp. 7764–7776.
31. R. M. Metzger, "INDO and MINDO/3 atom-in-molecule polarizabilities," J. Chem Phys., Vol. 74, No. 6, (1981), pp. 3444–3457.
32. D. Rinaldi, "Versatile techniques for semi-empirical SCF-LCAO calculations including minimization of energy," Comput. Chem., Vol. 1, (1976), pp. 109–114.
33. Z. B. Maksic, D. Kovacek, K. Kovacevic, Z. Medven, "Semiempirical calculations of the ESCA chemical shifts of nitrogen atoms in a chemical environment: failure of the PM3 and AM1 methods," THEOCHEM Vol. 110, No. 2, (1994), pp. 151–161.
34. J. Tyrrell, R. B. Weinstock, F. Weinhold, "Bond-antibond analysis of internal rotation barriers in glyoxal and related molecules: where INDO fails," Int. J. Quantum Chem., Vol. 19, No. 5, (1981), pp. 781–791.
35. P. Birner, H. J. Hofmann, "Quantum chemical calculations for the determination of the molecular structure of conjugated compounds. Part XVII. Critical examination of approximate LCAO MO methods. I. Reasons for the failure of the CNDO and INDO methods in theoretical conformation analysis of conjugated compounds," Int. J. Quantum Chem., Vol. 21, No. 5, (1982), pp. 833–843.
36. W. Klopper, J. Noga, "Accurate quantum-chemical prediction of enthalpies of formation of small molecules in the gas phase," Chem. Phys. Chem., Vol. 4, (2003), pp. 32–48.
37. NIST Atomic Spectra Database, www.physics.nist.gov/cgi-bin/AtData/display.ksh.
38. D. R. Lide, *CRC Handbook of Chemistry and Physics*, 79 the Edition, CRC Press, Boca Raton, Fla., (1998–9), pp. 9–80–9–85.
39. A. Weinstein, Letter to the Editor of Chemical and Engineering News, May 7, 1990.
40. R. Mills, "The Grand Unified Theory of Classical Quantum Mechanics," Int. J. Hydrogen Energy, Vol. 27, No. 5, (2002), pp. 565–590.
41. D. A. McQuarrie, *Quantum Chemistry*, University Science Books, Mill Valley, Calif., (1983), pp. 206–237.
42. W. J. Nellis, "Making Metallic Hydrogen," Scientific American, May, (2000), pp. 84–90.
43. J. A. Stratton, *Electromagnetic Theory*, McGraw-Hill Book Company, (1941), p. 195.
44. J. D. Jackson, Classical Electrodynamics, Second Edition, John Wiley & Sons, New York, (1975), pp. 17–22.
45. H. A. Haus, J. R. Melcher, "Electromagnetic Fields and Energy," Department of Electrical engineering and Computer Science, Massachusetts Institute of Technology, (1985), Sec. 5.3.
46. N. V. Sidgwick, *The Chemical Elements and Their Compounds*, Volume I, Oxford, Clarendon Press, (1950), p. 17.
47. M. D. Lamb, *Luminescence Spectroscopy*, Academic Press, London, (1978), p. 68.
48. D. R. Lide, *CRC Handbook of Chemistry and Physics*, 79 the Edition, CRC Press, Boca Raton, Fla., (1998–9), p. 10–175 to p. 10–177.
49. R. Mills and M. Nansteel, P. Ray, "Argon-Hydrogen-Strontium Discharge Light Source," IEEE Transactions on Plasma Science, Vol. 30, No. 2, (2002), pp. 639–653.
50. R. Mills, M. Nansteel, and P. Ray, "Excessively Bright Hydrogen-Strontium Plasma Light Source Due to Energy Resonance of Strontium with Hydrogen," J. of Plasma Physics, Vol. 69, (2003), pp. 131–158.
51. R. Mills, M. Nansteel, P. Ray, "Bright Hydrogen-Light Source due to a Resonant Energy Transfer with Strontium and Argon Ions," New Journal of Physics, Vol. 4, (2002), pp. 70.1–70.28.
52. R. Mills, J. Dong, Y. Lu, "Observation of Extreme Ultraviolet Hydrogen Emission from Incandescently Heated Hydrogen Gas with Certain Catalysts," Int. J. Hydrogen Energy, Vol. 25, (2000), pp. 919–943.
53. R. L. Mills, P. Ray, B. Dhandapani, J. He, "Extreme Ultraviolet Spectroscopy of Helium-Hydrogen Plasma," J. Phys. D, Applied Physics, Vol. 36, (2003), pp. 1535–1542.
54. R. L. Mills, P. Ray, J. Dong, M. Nansteel, B. Dhandapani, J. He, "Spectral Emission of Fractional-Principal-Quantum-Energy-Level Atomic and Molecular Hydrogen," Vibrational Spectroscopy, Vol. 31, No. 2, (2003), pp. 195–213.
55. R. L. Mills, P. Ray, B. Dhandapani, M. Nansteel, X. Chen, J. He, "New Power Source from Fractional Quantum Energy Levels of Atomic Hydrogen that Surpasses Internal Combustion," J. Mol. Struct., Vol. 643, No. 1–3, (2002), pp. 43–54.
56. R. Mills, P. Ray, "Spectral Emission of Fractional Quantum Energy Levels of Atomic Hydrogen from a Helium-Hydrogen Plasma and the Implications for Dark Matter," Int. J. Hydrogen Energy, Vol. 27, No. 3, pp. 301–322.
57. R. Mills, J. He, A. Echezuria, B Dhandapani, P. Ray, "Comparison of Catalysts and Plasma Sources of Vibrational Spectral Emission of Fractional-Rydberg-State Hydrogen Molecular Ion," European Journal of Physics D, submitted, http://www.blacklightpower.com/pdf/technical/sources 111303textfigs.pdf.?prog=normal&id=JAPIAU000092000012007008000001&idtype=cvips&gifs=Yes.

58. R. Mills, P. Ray, "Vibrational Spectral Emission of Fractional-Principal-Quantum-Energy-Level Hydrogen Molecular Ion," Int. J. Hydrogen Energy, Vol. 27, No. 5, (2002), pp. 533–564.
59. R. L. Mills, P. Ray, "A Comprehensive Study of Spectra of the Bound-Free Hyperfine Levels of Novel Hydride Ion H$^-$(½), Hydrogen, Nitrogen, and Air," Int. J. Hydrogen Energy, Vol. 28, No. 8, (2003), pp. 825–871.
60. R. Mills, "Spectroscopic Identification of a Novel Catalytic Reaction of Atomic Hydrogen and the Hydride Ion Product," Int. J. Hydrogen Energy, Vol. 26, No. 10, (2001), pp. 1041–1058.
61. R. L. Mills, P. Ray, B. Dhandapani, R. M. Mayo, J. He, "Comparison of Excessive Balmer α Line Broadening of Glow Discharge and Microwave Hydrogen Plasmas with Certain Catalysts," J. of Applied Physics, Vol. 92, No. 12, (2002), pp. 7008–7022.
62. R. L. Mills, P. Ray, E. Dayalan, B. Dhandapani, J. He, "Comparison of Excessive Balmer α Line Broadening of Inductively and Capacitively Coupled RF, Microwave, and Glow Discharge Hydrogen Plasmas with Certain Catalysts," IEEE Transactions on Plasma Science, Vol. 31, No. (2003), pp. 338–355.
63. H. Conrads, R. Mills, The. Wrubel, "Emission in the Deep Vacuum Ultraviolet from a Plasma Formed by Incandescently Heating Hydrogen Gas with Trace Amounts of Potassium Carbonate," Plasma Sources Science and Technology, Vol. 12, (3003), pp. 389–395.
64. R. Mills, T. Onuma, and Y. Lu, "Formation of a Hydrogen Plasma from an Incandescently Heated Hydrogen-Catalyst Gas Mixture with an Anomalous Afterglow Duration," Int. J. Hydrogen Energy, Vol. 26, No. 7, July, (2001), pp. 749–762.
65. R. Mills, P. Ray, R. M. Mayo, "CW HI Laser Based on a Stationary Inverted Lyman Population Formed from Incandescently Heated Hydrogen Gas with Certain Group I Catalysts," IEEE Transactions on Plasma Science, Vol. 31, No. 2, (2003), pp. 236–247.
66. R. Mills, P. Ray, R. M. Mayo, "The Potential for a Hydrogen Water-Plasma Laser," Applied Physics Letters, Vol. 82, No. 11, (2003), pp. 1679–1681.
67. R. L. Mills, Y. Lu, J. He, M. Nansteel, P. Ray, X. Chen, A. Voigt, B. Dhandapani, "Spectral Identification of New States of Hydrogen," J. Phys. Chem. B, submitted, http://www.blacklightpower.corn/pdf/technical/EGunNMR%20032604.pdf.
68. R. L. Mills, X. Chen, P. Ray, J. He, B. Dhandapani, "Plasma Power Source Based on a Catalytic Reaction of Atomic Hydrogen Measured by Water Bath Calorimetry," Thermochimica Acta, Vol. 406/1–2, pp. 35–53.
69. R. Mills, B. Dhandapani, M. Nansteel, J. He, T. Shannon, A. Echezuria, "Synthesis and Characterization of Novel Hydride Compounds," Int. J. of Hydrogen Energy, Vol. 26, No. 4, (2001), pp. 339–367.
70. R. Mills, B. Dhandapani, N. Greenig, J. He, "Synthesis and Characterization of Potassium Iodo Hydride," Int. J. of Hydrogen Energy, Vol. 25, Issue 12, December, (2000), pp. 1185–1203.
71. R. L. Mills, B. Dhandapani, J. He, "Highly Stable Amorphous Silicon Hydride," Solar Energy Materials & Solar Cells, Vol. 80, No. 1, pp. 1–20.
72. G. R. Fowles, *Analytical Mechanics*, Third Edition, Holt, Rinehart, and Winston, New York, (1977), pp. 145–158.
73. J. A. Stratton, *Electromagnetic Theory*. McGraw-Hill Book Company, (1941), pp. 38–54; 195–267.
74. Jahnke-Emde, *Tables of Functions*, 2nd ed., Teubner, (1933).
75. G. R. Fowles, *Analytical Mechanics*, Third Edition, Holt, Rinehart, and Winston, New York, (1977), pp. 161–164.
76. G. R. Fowles, *Analytical Mechanics*, Third Edition, Holt, Rinehart, and Winston, New York, (1977), pp. 57–66.
77. J. D. Jackson, *Classical Electrodynamics*, Second Edition, John Wiley & Sons, New York, (1975), p. 659.
78. J. D. Jackson, *Classical Electrodynamics*, Second Edition, John Wiley & Sons, New York, (1975), pp. 780–786.
79. D. A. McQuarrie, *Quantum Chemistry*, University Science Books, Mill Valley, Calif., (1983), p. 172.
80. K. P. Huber, G. Herzberg, *Molecular Spectra and Molecular Structure, IV. Constants of Diatomic Molecules*, Van Nostrand Reinhold Company, New York, (1979).
81. D. R. Lide, *CRC Handbook of Chemistry and Physics*, 79 the Edition, CRC Press, Boca Raton, Fla., (1998–9), p. 10-181.
82. R. Loch, R. Stengler, G. Werth, "Measurement of the electronic g factor of $H_2^+$," Phys. Rev. A, Vol. 38, No. 11, (1988), pp. 5484–5488.
83. C. Suarez, E. J. Nicholas, M. R. Bowman, "Gas-phase dynamic NMR study of the internal rotation in N-trifluoroacetlypyrrolidine," J. Phys. Chem. A, Vol. 107, (2003), pp. 3024–3029.
84. C. Suarez, "Gas-phase NMR spectroscopy," The Chemical Educator, Vol. 3, No. 2, (1998).
85. D. R. Lide, *CRC Handbook of Chemistry and Physics*, 79 th Edition, CRC Press, Boca Raton, Fla., (1998–9), p. 9-82.
86. E. Purcell, *Electricity and Magnetism*, McGraw-Hill, New York, (1965), pp. 370–389.
87. J. A. Stratton, *Electromagnetic Theory*, McGraw-Hill Book Company, (1941), pp. 211–215, 257–258.
88. Whittaker and Watson, *Modern Analysis,* 4th Edition, Cambridge University Press, (1927), pp. 512ff.
89. D. R. Lide, *CRC Handbook of Chemistry and Physics*, 79 th Edition, CRC Press, Boca Raton, Fla., (1998–9), p. A-30.
90. D. R. Lide, *CRC Handbook of Chemistry and Physics*, 79 th Edition, CRC Press, Boca Raton, Fla., (1998–9), p. A-29.
91. R. Mills, P. Ray, B. Dhandapani, W. Good, P. Jansson, M. Nansteel, J. He, A. Voigt, "Spectroscopic and NMR Identification of Novel Hydride Ions in Fractional Quantum Energy States Formed by an Exothermic Reaction of Atomic Hydrogen with Certain Catalysts," European Physical Journal-Applied Physics, submitted, http://www.blacklightpower.com/pdfNMR%20031303.pdf.
92. E. Purcell, *Electricity and Magnetism*, McGraw-Hill, New York, (1985), pp. 417–418.
93. K. K. Baldridge, J. S. Siegel, "Correlation of empirical δ(TMS) and absolute NMR chemical shifts predicted by ab initio computations," J. Phys. Chem. A, Vol. 103, (1999), pp. 4038–4042.
94. J. Mason, Editor, *Multinuclear NMR*, Plenum Press, New York, (1987), Chp. 3.
95. H. E. Gottlieb, V. Kotlyar, A. Nudelman, "NMR chemical shifts of common laboratory solvents as trace impurities," J. Org. Chem., Vol. 62, (1997), pp. 7512–7515.
96. R. Mills, B. Dhandapani, M. Nansteel, J. He, A. Voigt, "Identification of Compounds Containing Novel Hydride Ions by Nuclear Magnetic Resonance Spectroscopy," Int. J. Hydrogen Energy, Vol. 26, No. 9, (2001), pp. 965–979.
97. R. L. Mills, P. Ray, "Stationary Inverted Lyman Population Formed from Incandescently Heated Hydrogen Gas with Certain Catalysts," J. Phys. D, Applied Physics, Vol. 36, (2003), pp. 1504–1509.

98. K. Burke, E. K. U. Gross, "A guided tour of time-dependent density functional theory" in *Density Functionals: Theory and Applications*, D. Joubert, ed. Springer, Berlin, (1998) pp. 116–146.
99. T. Grabo, E. K. U. Gross, M. Luders, "Orbital functionals in density functional theory: the optimized effective potential method" Psi-k Newsletter, Vol. 16, No. 55, (1996), pp. 1–19.
100. K. Capelle, E. K. U. Gross, "Spin-density functionals from current-density functional theory and vice versa: a road towards new approximations," Phys. Rev. Letts., Vol. 78, No. 10, (1997), pp. 1872–1875.

The invention claimed is:

1. A system of computing and rendering a nature of a chemical bond comprising physical, Maxwellian solutions of charge, mass, and current density functions of hydrogen-type molecules and molecular ions, said system comprising:
processing means for processing Maxwellian equations representing charge, mass, and current density functions of hydrogen-type molecules and molecular ions, and;
an output device in communication with the processing means for displaying the nature of the chemical bond comprising physical, Maxwellian solutions of charge, mass, and current density functions of hydrogen-type molecules and molecular ions, wherein the physical, Maxwellian solutions of the charge, mass, and current density functions of hydrogen-type molecules and molecular ions comprises a solution of the classical wave equation $$\left[\nabla^2 - \frac{1}{v^2}\frac{\partial^2}{\partial t^2}\right]\rho(r, \theta, \phi, t) = 0.$$

2. A system of computing and rendering a nature of a chemical bond comprising physical, Maxwellian solutions of charge, mass, and current density functions of hydrogen-type molecules and molecular ions, said system comprising:
processing means for processing Maxwellan equations representing charge, mass, and current density functions of hydrogen-type molecules and molecular ions, and;
an output device in communication with the processing means for displaying the nature of the chemical bond comprising physical, Maxwellian solutions of charge, mass, and current density functions of hydrogen-type molecules and molecular ions, wherein the hydrogen molecular ion charge and current density functions, bond distance, and energies are solved from the Laplacian in ellipsoidal coordinates:

$$(\eta - \zeta)R_\xi \frac{\partial}{\partial \xi}\left(R_\xi \frac{\partial \phi}{\partial \xi}\right) + (\zeta - \xi)R_\eta \frac{\partial}{\partial \eta}\left(R_\eta \frac{\partial \phi}{\partial \eta}\right) + (\xi - \eta)R_\zeta \frac{\partial}{\partial \zeta}\left(R_\zeta \frac{\partial \phi}{\partial \zeta}\right) = 0.$$

3. A system of computing and rendering a nature of a chemical bond comprising physical, Maxwellian solutions of charge, mass, and current density functions of hydroqen-type molecules and molecular ions, said system comprising:
processing means for processing Maxwellian equations representing charge, mass, and current density functions of hydrogen-type molecules and molecular ions, and;
an output device in communication with the processing means for displaying the nature of the chemical bond comprising physical, Maxwellian solutions of charge, mass, and current density functions of hydrogen-type molecules and molecular ions, wherein the hydrogen molecular charge and current density functions, bond distance, and energies are solved from the Laplacian in ellipsoidal coordinates:

$$(\eta - \zeta)R_\xi \frac{\partial}{\partial \xi}\left(R_\xi \frac{\partial \phi}{\partial \xi}\right) + (\zeta - \xi)R_\eta \frac{\partial}{\partial \eta}\left(R_\eta \frac{\partial \phi}{\partial \eta}\right) + (\xi - \eta)R_\zeta \frac{\partial}{\partial \zeta}\left(R_\zeta \frac{\partial \phi}{\partial \zeta}\right) = 0$$

with the constraint of nonradiation.

4. A system of computing and rendering a nature of a chemical bond comprising physical, Maxwellian solutions of charge, mass, and current density functions of hydrogen-type molecules and molecular ions, said system comprising:
processing means for processing Maxwellian equations representing charge, mass, and current density functions of hydrogen-type molecules and molecular ions, and;
an output device in communication with the processing means for displaying the nature of the chemical bond comprising physical, Maxwellian solutions of charge, mass, and current density functions of hydrogen-type molecules and molecular ions, wherein the hydrogen molecular ion charge and current density functions, bond distance, and energies are solved from the Laplacian in ellipsoidal coordinates:

$$(\eta - \zeta)R_\xi \frac{\partial}{\partial \xi}\left(R_\xi \frac{\partial \phi}{\partial \xi}\right) + (\zeta - \xi)R_\eta \frac{\partial}{\partial \eta}\left(R_\eta \frac{\partial \phi}{\partial \eta}\right) + (\xi - \eta)R_\zeta \frac{\partial}{\partial \zeta}\left(R_\zeta \frac{\partial \phi}{\partial \zeta}\right) = 0$$

with the constraint of nonradiation.

5. A system of computing and rendering a nature of a chemical bond comprising physical, Maxwellian solutions of charge, mass, and current density functions of hydrogen-type molecules and molecular ions, said system comprising:
processing means for processing Maxwellian equations representing charge, mass, and current density functions of hydrogen-type molecules and molecular ions, and;
an output device in communication with the processing means for displaying the nature of the chemical bond comprising physical, Maxwellian solutions of charge, mass, and current density functions of hydrogen-type molecules and molecular ions, wherein the hydrogen molecular charge and current density functions, bond distance, and energies are solved from the Laplacian in ellipsoidal coordinates:

$$(\eta - \zeta)R_\xi \frac{\partial}{\partial \xi}\left(R_\xi \frac{\partial \phi}{\partial \xi}\right) + (\zeta - \xi)R_\eta \frac{\partial}{\partial \eta}\left(R_\eta \frac{\partial \phi}{\partial \eta}\right) + (\xi - \eta)R_\zeta \frac{\partial}{\partial \zeta}\left(R_\zeta \frac{\partial \phi}{\partial \zeta}\right) = 0$$

with the constraint of nonradiation.

6. A system of computing and rendering a nature of a chemical bond comprising physical, Maxwellian solutions of charge, mass, and current density functions of hydrogen-type molecules and molecular ions, said system comprising:

processing means for processing Maxwellian equations representing charge, mass, and current density functions of hydrogen-type molecules and molecular ions, and;

an output device in communication with the processing means for displaying the nature of the chemical bond comprising physical, Maxwellian solutions of charge, mass, and current density functions of hydrogen-type molecules and molecular ions, wherein a vibrational energy of hydrogen molecular ion $H_2^+(1/p)$ having a central field of +pe at each focus of the prolate spheroid molecular orbital is $$E_{vib}(1) = p^2 0.270 \text{ eV};$$

and the rotational energy absorbed by a hydrogen-type molecular ion with the transition from the state with the rotational quantum number J to one with the rotational quantum number J+1 is $$\Delta E = E_{J+1} - E_J$$
$$= \frac{p^2 \hbar^2}{m_p 2 a_H^2}[J+1]$$
$$= p^2[J+1]1.186 \times 10^{-21}$$
$$J = p^2[J+1]0.00740 \text{ eV}$$

7. A system of computing and rendering a nature of a chemical bond comprising physical, Maxwellian solutions of charge, mass, and current density functions of hydrogen-type molecules and molecular ions, said system comprising:

processing means for processing Maxwellian equations representing charge, mass, and current density functions of hydrogen-type molecules and molecular ions, and;

an output device in communication with the processing means for displaying the nature of the chemical bond comprising physical, Maxwellian solutions of charge, mass, and current density functions of hydrogen-type molecules and molecular ions, wherein a vibrational energy of hydrogen-type molecule $H_2(1/p)$ having a central field of +pe at each focus of the prolate spheroid molecular orbital is $$E_{vib}(1) = p^2 0.517 \text{ eV};$$

and the rotational energy absorbed by a hydrogen-type molecule with the transition from the state with the rotational quantum number J to one with the rotational quantum number J+1 is $$\Delta E = E_{J+1} - E_J = \frac{p^2 \hbar^2}{m_p a_o^2}[J+1]$$
$$= p^2[J+1]2.37 \times 10^{-21}$$
$$J = p^2[J+1]0.0148 \text{ eV}$$

8. A system of computing and rendering a nature of a chemical bond comprising physical, Maxwellian solutions of charge, mass, and current density functions of hydrogen-type molecules and molecular ions, said system comprising:

processing means for processing Maxwellian equations representing charge, mass, and current density functions of hydrogen-type molecules and molecular ions, and;

an output device in communication with the processing means for displaying the nature of the chemical bond comprising physical, Maxwellian solutions of charge, mass, and current density functions of hydrogen-type molecules and molecular ions, wherein a chemical shift $$\frac{\Delta B}{B}$$

of $H_2$ relative to a bare proton is given by $$\frac{\Delta B}{B} = \frac{\Delta B}{B} = -\mu_0 \left( \frac{p^3 4}{a_0^3} - \frac{p^3 \sqrt{2}}{a_0^3} \ln \frac{\sqrt{2}+1}{\sqrt{2}-1} \right) \frac{a_0^3 e^2}{36 p^2 m_e}$$
$$= -\mu_0 \left( 4 - \sqrt{2} \ln \frac{\sqrt{2}+1}{\sqrt{2}-1} \right) \frac{pe^2}{36 a_0 m_e}$$
$$= -p 28.01 \text{ ppm}$$

where p=1 for $H_2$.

9. A system of computing and rendering a nature of a chemical bond comprising physical, Maxwellian solutions of charge, mass, and current density functions of hydrogen-type molecules and molecular ions, said system comprising:

processing means for processing Maxwellian equations representing charge, mass, and current density functions of hydrogen-type molecules and molecular ions, and;

an output device in communication with the processing means for displaying the nature, of the chemical bond comprising physical, Maxwellian solutions of charge, mass, and current density functions of hvdroaen-type molecules and molecular ions, wherein a total NMR shift $$\frac{\Delta B_T}{B},$$

of the hydrogen molecule $H_2(1/p)$ having a central field of +pe at each focus of the prolate spheroid molecular orbital is given by the sum of that of $H_2$ plus a relativistic component:

$$\frac{\Delta B_T}{B} = -\mu_0 \left( 4 - \sqrt{2} \ln \frac{\sqrt{2}+1}{\sqrt{2}-1} \right) \frac{e^2}{36 a_0 m_e}(1 + \pi \alpha p)$$
$$\frac{\Delta B_T}{B} = -(28.01 + 0.64 \, p) \text{ppm}$$

where p=integer>1.

10. The system of any one of claims 1, 2, 3, 4, 5, and 6–9, wherein the output device is a display that displays at least one of visual or graphical media.

11. The system of claim 10 wherein the display is at least one of static or dynamic.

12. The system of claim 11 wherein at least one of vibration and rotation is be displayed.

13. The system of any one of claims 1, 2, 3, 4, 5, and 6–9, wherein displayed information is used to model reactivity and physical properties.

14. The system of any one of claims 1, 2, 3, 4, 5, and 6–9, wherein the output device is a monitor, video projector, printer, or three-dimensional rendering device.

15. The system of any one of claims 1, 2, 3, 4, 5, and 6–9, wherein displayed information is used to model other molecules and provides utility to anticipate their reactivity and physical properties.

16. The system of any one of claims 1, 2, 3, 4, 5, and 6–9, wherein the processing means is a general purpose computer.

17. The system of claim 16 wherein the general purpose computer comprises a central processing unit (CPU), one or more specialized processors, system memory, a mass storage device such as a magnetic disk, an optical disk, or other storage device, an input means.

18. The system of claim 17, wherein the input means comprises a serial port, usb port, microphone input, camera input, keyboard or mouse.

19. The system of any one of claims 1, 2, 3, 4, 5, and 6–9, wherein the processing means comprises a special purpose computer or other hardware system.

20. The system of any one of claims 1, 2, 3, 4, 5, and 6–9, further comprising computer program products.

21. The system of claim 20 comprising computer readable medium having embodied therein program code means.

22. The system of claim 21 wherein the computer readable media is any available media which can be accessed by a general purpose or special purpose computer.

23. The system of claim 22 wherein the computer readable media comprises at least one of RAM, ROM, EPROM, CD ROM, DVD or other optical disk storage, magnetic disk storage or other magnetic storage devices, or any other medium which can embody the desired program code means and which can be accessed by a general purpose or special purpose computer.

24. The system of claim 23 wherein the program code means comprises executable instructions and data which cause a general purpose computer or special purpose computer to perform a certain function of a group of functions.

25. The system of claim 24 wherein the program code is Mathematica programmed with an algorithm based on the physical solutions, and the computer is a PC.

26. The system of claim 25 wherein the algorithm is ParametricPlot3D[{2*Sqrt[1−z*z]*Cos[u],Sqrt[(1−z*z)]* Sin [u],z}{u,0,2*Pi},{z,−1,9999}], and the rendering is viewed from different perspectives.

27. The system of claim 26 wherein the algorithms for viewing from different perspectives comprises Show[Out [1], ViewPoint-22 {x,y,z}] where x, y, and z are Cartesian coordinates.

28. The system of claim 1 wherein the boundary constraint of the wave equation solution is nonradiation according to Maxwell's equations.

29. The system of claim 28 wherein a boundary condition is met for an ellipsoidal-time harmonic function when $$\omega_n = \frac{\pi \hbar}{m_e A} = \frac{\hbar}{m_e ab}$$

where the area of an ellipse is $$A = \pi ab$$

where 2b is the length of the semiminor axis and 2a is the length of the semimajor axis.

30. The system of claim 2 wherein a force balance equation for the hydrogen molecular ion is $$\frac{\hbar^2}{m_e a^2 b^2} 2ab^2 X = \frac{e^2}{4\pi\varepsilon_o} X$$

where $$X = \frac{1}{\sqrt{\xi+a^2}} \frac{1}{\sqrt{\xi+b^2}} \frac{1}{c} \sqrt{\frac{\xi^2-1}{\xi^2-\eta^2}}.$$

31. The system of claim 30 wherein the force balance equation has the parametric solution $$r(t) = a \cos \omega t + jb \sin \omega t$$

when the semimajor axis, a, is $$a = 2a_o.$$

32. The system of claim 31 wherein an internuclear distance, 2c', which is the distance between the foci is $$2c' = 2a_o;$$

the semiminor axis is $$b\sqrt{3}a_o, \text{ and}$$

the eccentricity, e, is $$e = \frac{1}{2}.$$

33. The system of claim 32 wherein a potential energy of the electron in the central field of the protons at the foci is $$V_e = \frac{-4e^2}{8\pi\varepsilon_0\sqrt{a^2-b^2}} \ln\frac{a+\sqrt{a^2-b^2}}{a-\sqrt{a^2-b^2}} = -59.7575 \text{ eV};$$

The potential energy of the two protons is $$V_p = \frac{e^2}{8\pi\varepsilon_0 a_H} = 13.5984 \text{ eV, and}$$

The kinetic energy of the electron is $$T = \frac{2\hbar^2}{m_e a\sqrt{a^2-b^2}} \ln\frac{a+\sqrt{a^2-b^2}}{a-\sqrt{a^2-b^2}} = 29.8787 \text{ eV}.$$

34. The system of claim 33 wherein during bond formation, the electron undergoes a reentrant oscillatory orbit with vibration of the protons, and the corresponding energy $\overline{E}_{osc}$ is the difference between the Doppler and average vibrational kinetic energies:

$$\overline{E}_{osc} = \overline{E}_D + \overline{E}_{Kvib} = (V_o + T + V_p)\sqrt{\frac{2\overline{E}_K}{Mc^2}} + \frac{1}{2}\hbar\sqrt{\frac{k}{\mu}}, \text{ and}$$

The total energy is $$E_T = V_e + T + V_p + \overline{E}_{osc}$$

$$E_T = -\left\{ \left[ \frac{\frac{e^2}{8\pi e_o a_H}(4\ln 3 - 1 - 2\ln 3)}{1 + \sqrt{\frac{2\hbar\sqrt{\frac{2e^2}{4pe_o(2a_H)^3}}}{m_e c^2}}} \right] - \frac{1}{2}\hbar\sqrt{\frac{k}{m}} \right\}$$

$$= -16.2803 \text{ eV} - 0.118811 \text{ eV} + \frac{1}{2}(0.29282 \text{ eV})$$

$$= -16.2527 \text{ eV}$$

35. The system of claim 34 wherein a bond dissociation energy, $E_D$, is the difference between the total energy of the hydrogen atom and $E_T$:

$$E_D = E(H) - E_T = 2.654 \text{ eV}$$

wherein the total energy of a hydrogen atom is $$E(H) = -13.59844 \text{ eV}.$$

36. The system of claim 3 wherein a force balance equation for the hydrogen molecule is $$\frac{\hbar^2}{m_e a^2 b^2} 2ab^2 X = \frac{e^2}{4\pi\varepsilon_o} X + \frac{\hbar^2}{2m_e a^2 b^2} 2ab^2 X$$

where $$X = \frac{1}{\sqrt{\xi + a^2}} \frac{1}{\sqrt{\xi + b^2}} \frac{1}{c} \sqrt{\frac{\xi^2 - 1}{\xi^2 - \eta^2}}.$$

37. The system of claim 36 wherein the force balance equation has the parametric solution $$r(t) = ia \cos \omega t + jb \sin \omega t$$

when the semimajor axis, a, is $$a = a_o.$$

38. The system of claim 37 wherein an internuclear distance, 2c', which is the distance between the foci is $$2c' = \sqrt{2}a_o;$$

the semiminor axis is $$b = \frac{1}{\sqrt{2}}a_o, \text{ and}$$

the eccentricity, e, is $$e = \frac{1}{\sqrt{2}}.$$

39. The system of claim 38 wherein a potential energy of the two electrons in the central field of the protons at the foci is $$V_e = \frac{-2e^2}{8\pi\varepsilon_o\sqrt{a^2 - b^2}}\ln\frac{a + \sqrt{a^2 - b^2}}{a - \sqrt{a^2 - b^2}} = -67.836 eV;$$

The potential energy of the two protons is $$V_p = \frac{e^2}{8\pi\varepsilon_o\sqrt{a^2 - b^2}} = 19.242 eV;$$

The kinetic energy of the electrons is $$T = \frac{\hbar^2}{2m_e a\sqrt{a^2 - b^2}}\ln\frac{a + \sqrt{a^2 - b^2}}{a - \sqrt{a^2 - b^2}} = 33.918 eV, \text{ and}$$

The energy, $V_m$, of the magnetic force between the electrons is $$V_m = \frac{\hbar^2}{4m_e a\sqrt{a^2 - b^2}}\ln\frac{a + \sqrt{a^2 - b^2}}{a - \sqrt{a^2 - b^2}} = -16.959 eV.$$

40. The system of claim 39 wherein during bond formation, the electrons undergo a reentrant oscillatory orbit with vibration of the protons, and the corresponding energy $\overline{E}_{osc}$ is the difference between the Doppler and average vibrational kinetic energies:

$$\overline{E}_{osc} = \overline{E}_D + \overline{E}_{Kvib} = (V_e + T + V_m + V_p)\sqrt{\frac{2\overline{E}_K}{Mc^2}} + \frac{1}{2}\hbar\sqrt{\frac{k}{\mu}}, \text{ and}$$

The total energy is $$E_T = V_e + T + V_m + V_p + \overline{E}_{osc}$$

$$E_T = -\frac{e^2}{8\pi\varepsilon_o a_0}\left[\left(2\sqrt{2} - \sqrt{2} + \frac{\sqrt{2}}{2}\right)\ln\frac{\sqrt{2} + 1}{\sqrt{2} - 1} - \sqrt{2}\right]$$

$$\left[1 + \sqrt{\frac{2\hbar\sqrt{\frac{e^2}{4\pi\varepsilon_o a_0^3}}}{m_e c^2}}\right].$$

$$-\frac{1}{2}\hbar\sqrt{\frac{k}{\mu}}$$

$$= -31.689 \text{ eV}$$

41. The system of claim 40 wherein a bond dissociation energy, $E_D$, is the difference between the total energy of the hydrogen atoms and $E_T$:

$$E_D = E(2H[a_H]) - E_T = 4.478 \text{ eV}$$

wherein the total energy of two hydrogen atoms is $$E(2H[a_H]) = -1.27.21 \text{ eV}.$$

42. The system of claim 4 wherein a force balance equation the hydrogen molecular ion $H_2^+(1/p)$ having a central field of +pe at each focus of the prolate spheroid molecular orbital is $$\frac{\hbar^2}{m_e a^2 b^2} 2ab^2 X = \frac{pe^2}{4\pi\varepsilon_o} X$$

where $$X = \frac{1}{\sqrt{\xi + a^2}} \frac{1}{\sqrt{\xi + b^2}} \frac{1}{c} \sqrt{\frac{\xi^2 - 1}{\xi^2 - \eta^2}}.$$

43. The system of claim 42 wherein a force balance equation has the parametric solution $$r(t) = ia \cos \omega t + jb \sin \omega t$$

when the semimajor axis, a, is $$a = \frac{2a_0}{p}.$$

44. The system of claim 43 wherein an internuclear distance, 2c', which is the distance between the foci is $$2c' = \frac{2a_0}{p};$$

the semiminor axis is $$b = \frac{\sqrt{3}}{p} a_o, \text{ and}$$

the eccentricity, e, is $$e = \frac{1}{2}.$$

45. The system of claim 44 wherein a potential energy of the electron in the central field of +pe at the foci is $$V_e = \frac{-4p^2 e^2}{8\pi\varepsilon_o a_o} \ln 3;$$

The potential energy of the two protons is $$V_P = \frac{p^2 e^2}{8\pi\varepsilon_o a_o}, \text{ and}$$

The kinetic energy of the electron is $$T = \frac{2p^2 e^2}{8\pi\varepsilon_o a_o} \ln 3.$$

46. The system of claim 45 wherein during bond formation, the electron undergoes a reentrant oscillatory orbit with vibration of the protons, and the corresponding energy $\overline{E}_{osc}$ is the difference between the Doppler and average vibrational kinetic energies:

$$\overline{E}_{osc} = \overline{E}_D + \overline{E}_{Kvib} = (V_c + T + V_P)\sqrt{\frac{2\overline{E}_K}{Mc^2}} + \frac{1}{2}\hbar\sqrt{\frac{k}{\mu}}, \text{ and}$$

The total energy of the hydrogen molecular ion $H_2^+(1/p)$ having a central field of +pe at each focus of the prolate spheroid molecular orbital is $$E_T = V_e + T + V_P + \overline{E}_{osc}$$

$$E_T = -p^2 \left\{ \frac{e^2}{8\pi\varepsilon_o a_H}(4\ln 3 - 1 - 2\ln 3) \right.$$

$$\left. \left[1 + p\sqrt{\frac{2\hbar\sqrt{\frac{2e^2}{4\pi\varepsilon_o(2a_H)^3}}}{m_e c^2}}\right] - \frac{1}{2}\hbar\sqrt{\frac{k}{\mu}} \right\}.$$

$$= -p^2 16.13392 \text{eV} - p^3 0.118755 \text{eV}$$

47. The system of claim 46 wherein a bond dissociation energy, $E_D$, is the difference between the total energy of the hydrogen atom H(1/p) and $E_T$:

$$E_D = -p^2 13.59844 - E_T$$

$$= -p^2 13.59844 - (-p^2 16.13392 \text{ eV} - p^3 0.118755 \text{ eV})$$

$$= p^2 2.535 \text{ eV} + p^3 0.118755 \text{ eV}$$

wherein the total energy of a hydrogen atom H(1/p) is $$E(H(1/p)) = -p^2 13.59844 \text{ eV}.$$

48. The system of claim 5 wherein a force balance equation for the hydrogen molecule $H_2(1/p)$ having a central field of +pe at each focus of the prolate spheroid molecular orbital is $$\frac{\hbar^2}{m_e a^2 b^2} 2ab^2 X = \frac{pe^2}{4\pi\varepsilon_o} X + \frac{\hbar^2}{2m_e a^2 b^2} 2ab^2 X$$

where $$X = \frac{1}{\sqrt{\xi + a^2}} \frac{1}{\sqrt{\xi + b^2}} \frac{1}{c} \sqrt{\frac{\xi^2 - 1}{\xi^2 - \eta^2}}.$$

49. The system of claim 48 wherein the force balance equation has the parametric solution $$r(t) = ia \cos \omega t + jb \sin \omega t$$

when the semimajor axis, a, is $$a = \frac{a_o}{p}.$$

50. The system of claim 49 wherein an internuclear distance, 2c', which is the distance between the foci is $$2c' = \frac{\sqrt{2}}{p} a_o;$$

the semiminor axis is $$b = c' = \frac{1}{p\sqrt{2}} a_o, \text{ and}$$

the eccentricity, e, is $$e = \frac{1}{\sqrt{2}}.$$

51. The system of claim 50 wherein a potential energy of the two electrons in the central field of +pe at the foci is $$V_e = \frac{-2pe^2}{8\pi\varepsilon_o \sqrt{a^2 - b^2}} \ln \frac{a + \sqrt{a^2 - b^2}}{a - \sqrt{a^2 - b^2}};$$

The potential energy of the two protons is $$V_p = \frac{p}{8\pi\varepsilon_o} \frac{e^2}{\sqrt{a^2 - b^2}};$$

The kinetic energy of the electrons is $$T = \frac{\hbar^2}{2m_e a \sqrt{a^2 - b^2}} \ln \frac{a + \sqrt{a^2 - b^2}}{a - \sqrt{a^2 - b^2}}, \text{ and}$$

The energy, $V_m$, of the magnetic force between the electrons is $$V_m = \frac{-\hbar^2}{4m_e a \sqrt{a^2 - b^2}} \ln \frac{a + \sqrt{a^2 - b^2}}{a - \sqrt{a^2 - b^2}}.$$

52. The system of claim 51 wherein during bond formation, the electrons undergo a reentrant oscillatory orbit with vibration of the protons, and the corresponding energy $\overline{E}_{osc}$ is the difference between the Doppler and average vibrational kinetic energies:

$$\overline{E}_{osc} = \overline{E}_D + \overline{E}_{Kvib} = (V_e + T + V_m + V_p)\sqrt{\frac{2\overline{E}_K}{Mc^2}} + \frac{1}{2}\hbar p^2 \sqrt{\frac{k}{\mu}}, \text{ and}$$

$$= -p^3 0.326469 \text{ eV} + \frac{1}{2}p^2(0.56764 \text{ eV})$$

The total energy is $$E_T = V_e + T + V_m + V_P + \overline{E}_{osc}$$

$$E_T = -p^2 \left\{ \frac{e^2}{8\pi\varepsilon_o a_O} \left[ 2\sqrt{2} - \sqrt{2} + \frac{\sqrt{2}}{2} \ln \frac{\sqrt{2}+1}{\sqrt{2}-1} - \sqrt{2} \right] \right.$$

$$\left. \left[ 1 + p \sqrt{\frac{2\hbar \sqrt{\frac{e^2}{4\pi\varepsilon_o a_O^3}}}{m_e c^2}} \right] - \frac{1}{2}\hbar \sqrt{\frac{k}{\mu}} \right\}.$$

$$= -p^2 31.351 \text{eV} - p^3 0.326469 \text{eV}$$

53. The system of claim 52 wherein a bond dissociation energy, $E_D$, is the difference between the total energy of the hydrogen atoms H(1/p) and $E_T$:

$$E_D = E(2H(1/p)) - E_T$$

$$= -p^2 27.20 \text{ eV} - E_T$$

$$= -p^2 27.20 \text{ eV} - (-p^2 31.351 \text{ eV} - p^3 0.326469 \text{ eV})$$

$$= p^2 4.151 \text{ eV} + p^3 0.326469 \text{ eV}$$

wherein the total energy of two hydrogen atoms H(1/p) is $$E(2H(1/p)) = -p^2 27.20 \text{ eV.}$$

* * * * *